(12) United States Patent
Gesley

(10) Patent No.: US 8,913,121 B2
(45) Date of Patent: Dec. 16, 2014

(54) SYSTEM FOR IMAGE RENDERING OR SPECTRAL RECOGNITION

(75) Inventor: Mark Gesley, Oakland, CA (US)

(73) Assignee: Spynsite, LLC, Oakland, CA (US)

( * ) Notice: Subject to any disclaimer, the term of this patent is extended or adjusted under 35 U.S.C. 154(b) by 785 days.

(21) Appl. No.: 13/180,544

(22) Filed: Jul. 11, 2011

(65) Prior Publication Data

US 2012/0069170 A1 Mar. 22, 2012

Related U.S. Application Data

(60) Provisional application No. 61/363,278, filed on Jul. 11, 2010.

(51) Int. Cl.
| | |
|---|---|
| *H04N 7/18* | (2006.01) |
| *G06K 9/00* | (2006.01) |
| *G06T 7/00* | (2006.01) |
| *G06K 9/20* | (2006.01) |
| *G01N 21/65* | (2006.01) |
| *G01N 15/10* | (2006.01) |
| *G01N 21/64* | (2006.01) |

(52) U.S. Cl.
CPC ..... *G06K 9/2036* (2013.01); *G06T 2207/10024* (2013.01); *G06K 9/00523* (2013.01); *G01N 2015/1006* (2013.01); *G01N 2021/6439* (2013.01); *G01N 2021/6423* (2013.01); *G06T 7/0012* (2013.01); *G01N 21/6458* (2013.01); *G06T 2207/20081* (2013.01); *G06T 2207/30024* (2013.01); *G06T 2207/10056* (2013.01); *G01N 21/65* (2013.01)
USPC .......................................................... 348/79

(58) Field of Classification Search
CPC .................. G01N 2015/1006; G01N 21/6458; G01N 21/65; G01N 2021/6423; G01N 2021/6439; G06K 9/00523; G06K 9/2036; G06T 2207/30024; G06T 2207/10024; G06T 2207/10056; G06T 2207/20081; G06T 7/0012
USPC .......................................................... 348/79
See application file for complete search history.

(56) References Cited

U.S. PATENT DOCUMENTS

| | | | | |
|---|---|---|---|---|
| 2009/0279081 A1* | 11/2009 | Urano et al. | ............... | 356/237.5 |
| 2011/0142301 A1* | 6/2011 | Boroczky et al. | ............ | 382/128 |
| 2012/0136259 A1* | 5/2012 | Milner et al. | ............... | 600/478 |

OTHER PUBLICATIONS

Chen, et al, "Microfluidic chip for blood cell separation and collection based on crossflow filtration," www.sciencedirect.com, Aug. 6, 2007, pp. 216-221.
Fisher, "The Use of Multiple Measurments in Taxonomic Problems," Reproduced from "Contributions to Mathematical Statics" (1950) by permission of John Wiley & Sons, Inc., pp. 465-475.
Harris, "Spectral Mapping Tools from the Earth Sciences Applied to Spectral Microscopy Data," International Society for Analytical Cytology, 2006, pp. 872-879.
Sollier, et al, "Passive microfluidic devices for plasma extraction from whole human blood," www.elsevier.com/locate/snb, 2009, pp. 617-624.

(Continued)

*Primary Examiner* — Thai Tran
*Assistant Examiner* — William Tran
(74) *Attorney, Agent, or Firm* — Berkeley Law & Technology Group, LLP

(57) ABSTRACT

Embodiments of a method or a system for rendering images or spectral recognition are described.

18 Claims, 25 Drawing Sheets

(56) References Cited

OTHER PUBLICATIONS

Lim, et al, "Light-scattering spectroscopy differentiates fetal from adult nucleated red blood cells: may lead to noninvasive prenatal diagnosis," May 1, 2009, vol. 34, No. 9, Optics Letters, pp. 1483-1485.
Lee, et al, "Treelets—An Adaptive Multi-Scale Basis for Sparse Unordered Data," The Annals of Applied Statistics, 2008, vol. 2, No. 2, pp. 435-471.
Alfano, "Preface to the Second Edition," The Supercontinuum Laser Source: Fundamentals with Updated References, Springer 2006, 3 pages.
Fianium, "Supercontinuum SC400 and SC450," New Product Datasheet, http://www.fianium.com/pdf/sc-400-450.pdf, Jan. 2010, 2 pages.
Sony, "Diagonal 11mm (Type 2/3) Progressive Scan CCD Image Sensor with Square Pixel for B/W Cameras," http://www.unibrain.com/download/pdfs/ub1394cam/ICX285AL.pdf, pp. 1-21.
Candes, et al, "The Dantzig Selector: Statistical Estimation When p is Much Larger than n1," The Annals of Statistics 2007, vol. 35, No. 6, pp. 1-41.
Ding, et al, "K-Means Clustering via Principal Component Analysis," Proceedings of the 21st International Conference on Machine Learning, Banff, Canada, 2004, pp. 1-9.
Donoho, "Compressed Sensing," Department of Statistics Stanford University, Sep. 14, 2004, pp. 1-34.
Fisher, "The Use of Multiple Measurements in Taxonomic Problems," Annals of Eugenics, v. 7, 1936, pp. 465-475.
Friedman, Regularized Discriminant Analysis,: Department of Statistics & Stanford Linear Accelerator Center, Jul. 1988, pp. 1-32.
Goldberg, "What Every Computer Scientist Should Know about Floating-Point Arithmetic," Copyright 1991, Association for Computing Machinery, Inc., pp. 171-264.
Guo, et al, "A Study of Regularized Gaussian Classifiers in High-Dimension Small Sample Set Case Based on MDL Principle with Application to Spectrum Recognition," Elsevier Ltd., 2008, pp. 2842-2854.
Houle, et al, "Can Shared-Neighbor Distances Defeat the Curse of Dimensionality?," Proceedings of the 22nd International Conference of Scientific and Statistical Database Management, Jun. 31-Jul. 2, 2010, Heidelberg, Germany, 18 pages.
Hughes, "On the Mean Accuracy of Statistical Pattern Recognizers," IEEE, Downloaded Apr. 7, 2010, pp. 55-63.
Lee, et al, "Treelets—An Adaptive Multi-Scale Basis for Sparse Unordered Data," The Annals of Applied Statistics, 2008, vol. 2 No. 2, pp. 435-471.
Saito, et all, "Local Discriminant Bases," SPIE vol. 2303, 1994, pp. 1-13.
Smith, et al, "Integrated Raman and Angular Scattering Microscopy Reveals Chemical and Morphological Differences Between Activated and Nonactivated CD8+ T Lymphocytes," Journal of Biomedical Optics, May/Jun. 2010, vol. 15(3), pp. 1-11.
Tibshirani, "Regression Shrinkage and Selection via the Lasso," Journal of the Royal Statistical Society, Series B (Methodological), vol. 58, Issue 1, 1996, pp. 267-288.
Uzunbajakava, et al, "Nonresonant Raman Imaging of Protein Distribution in Single Human Cells," Biopolymers (Biospectroscopy), vol. 72, 2003, pp. 1-9.
Wu, et al, "Probability Estimates for Multi-class Classification by Pairwise Coupling," Journal of Machine Learning Research 5, 2004, pp. 975-1005.
Saad, et al, "Interative Solution of Linear Systems in the 20th Century," Journal of Computational and Applied Mathematics 123, 2000, pp. 1-33.
Golub, et al, "Eigenvalue Computation in the 20th Century," Journal of Computational and Applied Mathematics 123, 2000, pp. 35-65.
Watkins, "QR-like Algorithms for Eigenvalue Problems," Journal of Computational and Applied Mathematics 123, 2000, pp. 67-83.
Van Loan, "The Ubiquitous Kronecker Product," Journal of Computational and Applied Mathematics 123, 2000, pp. 85-100.
Morgan, "Preconditioning Eigenvalues and Some Comparison of Solvers," Journal of Computational and Applied Mathematics 123, 2000, pp. 101-115.
Parlett, "For Tridiagonals T Replace T with LDLt," Journal of Computational and Applied Mathematics 123, 2000, pp. 117-130.
Ipsen, "An Overview of Relative Sin Theorems for Invariant Subspaces of Complex Matrices," Journal of Computational and Applied Mathematics 123, 2000, pp. 131-153.
Sameh, et al, "The Trace Minimization Method for the Symmetric Generalized Eigenvalue Problem," Journal of Computational and Applied Mathematics 123, 2000, pp. 155-175.
Hadjidimos, "Successive Overrelaxation (SOR) and Related Methods," Journal of Computational and Applied Mathematics 123, 2000, 177-199.
Frommer, et al, "On Asynchronous Iterations," Journal of Computational and Applied Mathematics 123, 2000, pp. 201-216.
Calvetti, et al, "Interative Methods for Large Continuation Problems," Journal of Computational and Applied Mathematics 123, 2000, pp. 217-240.
Brezinski, et al, "The Matrix and Polynomial Approaches to Lanczos-type Algorithms," Journal of Computational and Applied Mathematics 123, 2000, pp. 241-260.
Eiermann, et al, "Analysis of Acceleration Strategies for Restarted Minimal Residual Methods," Journal of Computational and Applied Mathematics 123, 2000, pp. 261-292.
Bridson, et al, "Refining an Approximate Inverse," Journal of Computational and Applied Mathematics 123, 2000, pp. 293-306.
Koning, et al, "Scalable Preconditioned Conjugate Gradient Inversion of Vector Finite Element Mass Matrices," Journal of Computational and Applied Mathematics 123, 2000, pp. 307-321.
Chan, et al, "Robust Multigrid Methods for Nonsmooth Coefficient Elliptic Linear Systems," Journal of Computational and Applied Mathematics 123, 2000, pp. 323-352.
Poole, et al, "The Rook's Pivoting Strategy," Journal of Computational and Applied Mathematics 123, 2000, pp. 353-369.
Mehrmann, et al, "Numerical Methods in Control," Journal of Computational and Applied Mathematics 123, 2000, pp. 371-394.
Freund, "Krylov-subspace Methods for Reduced-Order Modeling in Circuit Simulation," Journal of Computational and Applied Mathematics 123, 2000, pp. 395-421.
Calvetti, et al, "Tikhonov Regularization and the L-curve for Large Discrete Ill-posed Problems," Journal of Computational and Applied Mathematics 123, 2000, pp. 423-446.
O'Leary, "Symbosis Between Linear Algebra and Optimization," Journal of Computational and Applied Mathematics 123, 2000, pp. 447-465.
Plemmons, et al, "Some Computational Problems Arising in Adaptive Optics Imaging Systems," ournal of Computational and Applied Mathematics 123, 2000, pp. 467-487.
Dongarra, et al, "Numerical Linear Algebra Algorithms and Software," Journal of Computational and Applied Mathematics 123, 2000, pp. 489-514.
Duff, "The Impact of High-performance Computing in the Solution of Linear Systems: Trends and Problems," Journal of Computational and Applied Mathematics 123, 2000, pp. 515-530.
Hastie, et al, "Classification by Pairwise Coupling," Department of Statistics, trevor@playfair.stanford.edu, Department of Preventive Medicine and Biostatistics, tibs@utstat.toronto.edu, 1998, 38 pages.
Von Neumann, et al, "Numerical Inverting of Matrices of High Order," Presented to the Society Sep. 5, 1947, pp. 1021-1099.
Moritz, et al, "Evaluation of *Escherichia coli* Cell Response to Antibiotic Treatment Using Laser Tweezers Raman Spectroscopy," Nov. 2010, Journal of Clinical Microbiol 48(11), 13 pages.
Press, et al, "Numerical Receipes: The Art of Scientific Computing," 3rd Addition, Cambridge University Press, Section 11.0.6 and Section 11.1, 2007, pp. 570-572.
Dean, "Elements of Abstract Algebra," Wiley and Sons, Inc. Theorem 16, 1966, p. 299.

(56) References Cited

OTHER PUBLICATIONS

Golub, et al, "Matrix Computations," 3rd Edition, John Hopkins University Press, Singular Value Decomposition, Section 2.5.3, 1996, pp. 70-71, Sensitivity of Square Systems, Section 2.7, pp. 80-82 and Determinants and Nearness to Singularity, Section 2.7.3, pp. 82-83.

Knuth, "The Art of Computer Programming," vol. 2, Seminumerical Algorithms, 3rd Edition, 1998, pp. 229-235, 246-247, 264-265 and 278.

Fukunaga, "Introduction to Statistical Pattern Recognition," 2nd Edition, Academic Press, Chapter 10, 1991, pp. 441-507.

Blanchard, et al, "Mathematical Methods in Physics," 2003, p. 193.

* cited by examiner

|  | Possible states | | | | | | | |
|---|---|---|---|---|---|---|---|---|
|  | 1 | 2 | 3 | 4 | 5 | 6 | 7 | 8 |
| Pair wise classifiers AB | A | A | A | A | B | B | B | B |
| AC | A | A | C | C | A | A | C | C |
| BC | B | C | B | C | B | C | B | C |
| Joint outcomes | A | A | T | C | B | T | B | C |

|  | Possible states | | | | | | | | | | | | | | | | | | | | | | | | | | |
|---|---|---|---|---|---|---|---|---|---|---|---|---|---|---|---|---|---|---|---|---|---|---|---|---|---|---|---|
|  | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 |
| Pair wise classifiers AB | A | A | A | A | A | A | A | A | A | B | B | B | B | B | B | B | B | B | O | O | O | O | O | O | O | O | O |
| AC | A | A | C | C | C | O | O | O | O | A | A | C | C | C | O | O | O | O | A | A | C | C | C | O | O | O | O |
| BC | B | C | O | B | C | O | B | C | O | B | C | O | B | C | O | B | C | O | B | C | O | B | C | O | B | C | O |
| Joint outcomes | A | A | T | C | O | O | O | O | B | T | O | B | C | O | B | C | O | O | O | O | O | O | O | O | O | O | O |

SYSTEM FOR IMAGE RENDERING OR SPECTRAL RECOGNITION

RELATED APPLICATION

This patent application claims priority to U.S. Provisional Patent Application No. 61/363,278, filed on Jul. 11, 2010, by Mark Gesley titled "A SYSTEM FOR IMAGE RENDERING OR SPECTRAL RECOGNITION," which is assigned to the assignee of the currently claimed subject matter. The foregoing provisional patent application is herein incorporated by reference in its entirety.

FIELD

This patent application is related to a system for image rendering or spectral recognition.

BACKGROUND

Reliable detection or isolation of low cell concentrations, such as, for example, for a rare blood disease is desirable, but remains a technical challenge. Due at least in part to relatively low cell concentration, a large number of cells are typically examined. However, examination of a large number of cells may be challenging to accomplish in a reasonable period of time.

Flow cytometers, for example, may be applied to examine cells at rates of up to approximately 7,000 cells/sec. However, in some situations, it may be prudent to examine $5 \times 10^9$ or more cells to identify 5 rare cells, as one simple example. Applying state of the art technology this may involve 200 hours of cell processing. For example, continuing with this simple example, $5 \times 10^9 / 7 \times 10^3 = 7 \times 10^5$ sec=200 hours. This implies that flow cytometry may be too slow for advanced rare cell detection in a reasonable amount of time. To detect 1 part per billion cells in less than one day, for example, may be more desirable as an approach to detection and hopefully treatment.

BRIEF DESCRIPTION OF THE DRAWINGS

Claimed subject matter is particularly pointed out and distinctly claimed in the concluding portion of the specification. However, both as to organization or method of operation, together with objects, features, or advantages thereof, it may best be understood by reference to the following detailed description if read with the accompanying drawings in which:

DETAILED DESCRIPTION

Figure 1:
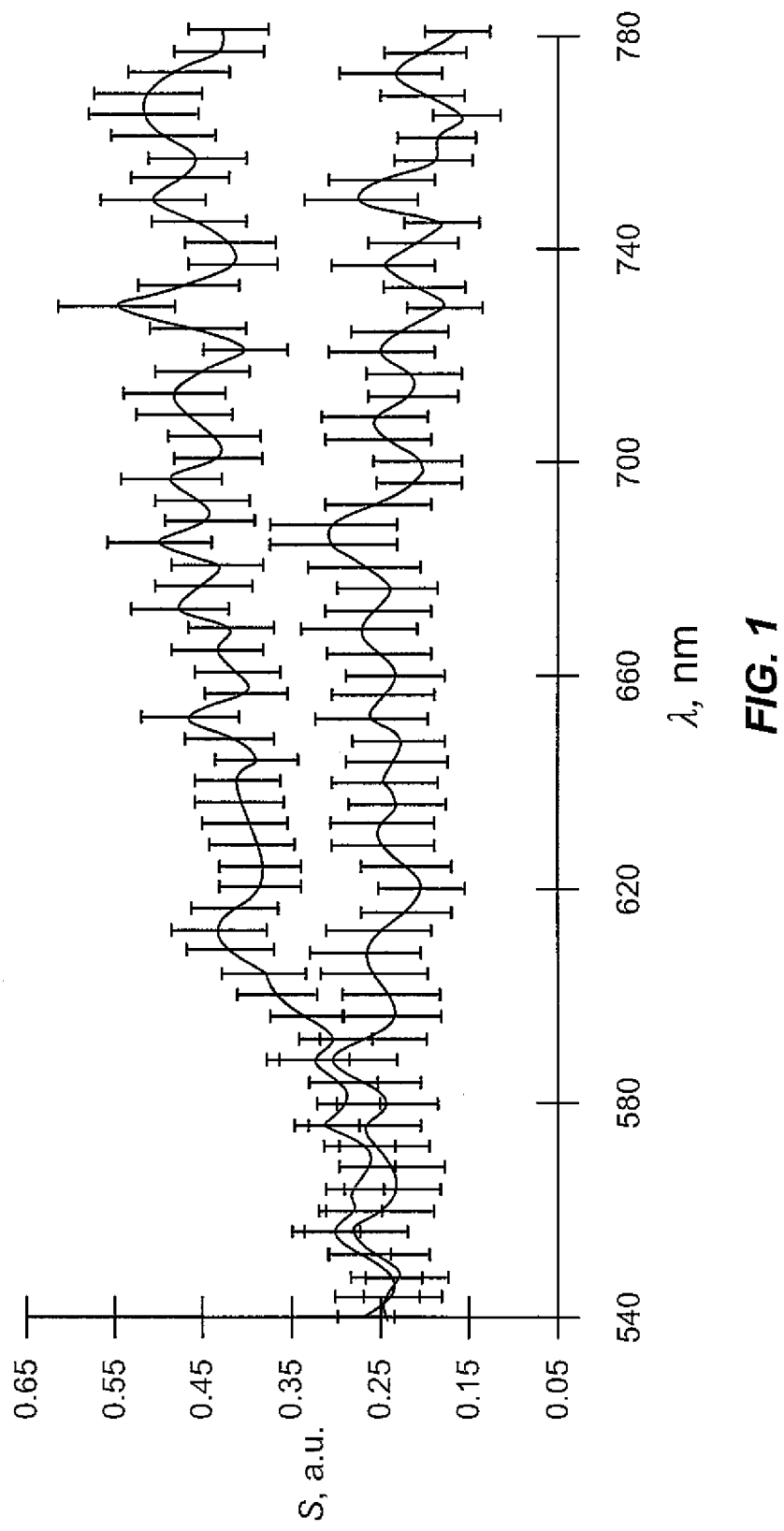
FIG. 1 is a plot showing fetal (fNRBC) and adult aNRBC having different spectra obtained using an embodiment of a non-invasive method; upper and lower curves are spectra for fNRBC and aNRBC respectively.

In the following detailed description, numerous specific details are set forth to provide a thorough understanding of claimed subject matter. However, it will be understood by those skilled in the art that claimed subject matter may be practiced without these specific details. In other instances, methods, apparatuses, or systems that may be known by or to one of ordinary skill have not been described in detail so as not to obscure claimed subject matter.

Reference throughout this specification to "one embodiment" or "an embodiment" is intended to mean that a particular feature, structure, or characteristic described in connection with an embodiment may be included in at least one embodiment of claimed subject matter. Thus, appearances of the phrase "in one embodiment," "an embodiment" or the like in various places throughout this specification are not necessarily all referring to the same embodiment. Furthermore, particular features, structures, or characteristics may be combined in one or more embodiments.

Some portions of the detailed description which follows are presented in terms of algorithms or symbolic representations of operations on binary digital signals stored within a memory of a specific apparatus or special purpose computing device or platform. In the context of this particular specification, the term "specific apparatus" or the like includes a general purpose computer after it is programmed to perform particular functions pursuant to instructions from program software. Algorithmic descriptions or symbolic representations are examples of techniques used by those of ordinary skill in the signal processing or related arts to convey the substance of their work to others skilled in the art. An algorithm is here, and generally, is considered to be a self-consistent sequence of operations or similar signal processing leading to a desired result. In this context, operations or processing may involve physical manipulation of physical quantities. Typically, although not necessarily, quantities may take the form of electrical or magnetic signals capable of being stored, transferred, combined, compared or otherwise manipulated. It has proven convenient at times, principally for reasons of common usage, to refer to signals as bits, data, values, elements, symbols, characters, terms, numbers, numerals or the like. It should be understood, however, that all of these or similar terms are to be associated with appropriate physical quantities and are merely convenient labels. Unless specifically stated otherwise, as apparent from the following discussion, it is appreciated that throughout this specification discussions utilizing terms such as "processing," "computing," "calculating," "determining" or the like refer to actions or processes of a specific apparatus, such as a special purpose computer or a similar special purpose electronic computing device. In the context of this specification, therefore, a special purpose computer or a similar special purpose electronic computing device is capable of manipulating or transforming signals, typically represented as physical electronic or magnetic quantities within memories, registers, or other information storage devices, transmission devices, or display devices of a special purpose computer or similar special purpose electronic computing device.

Figure 2:
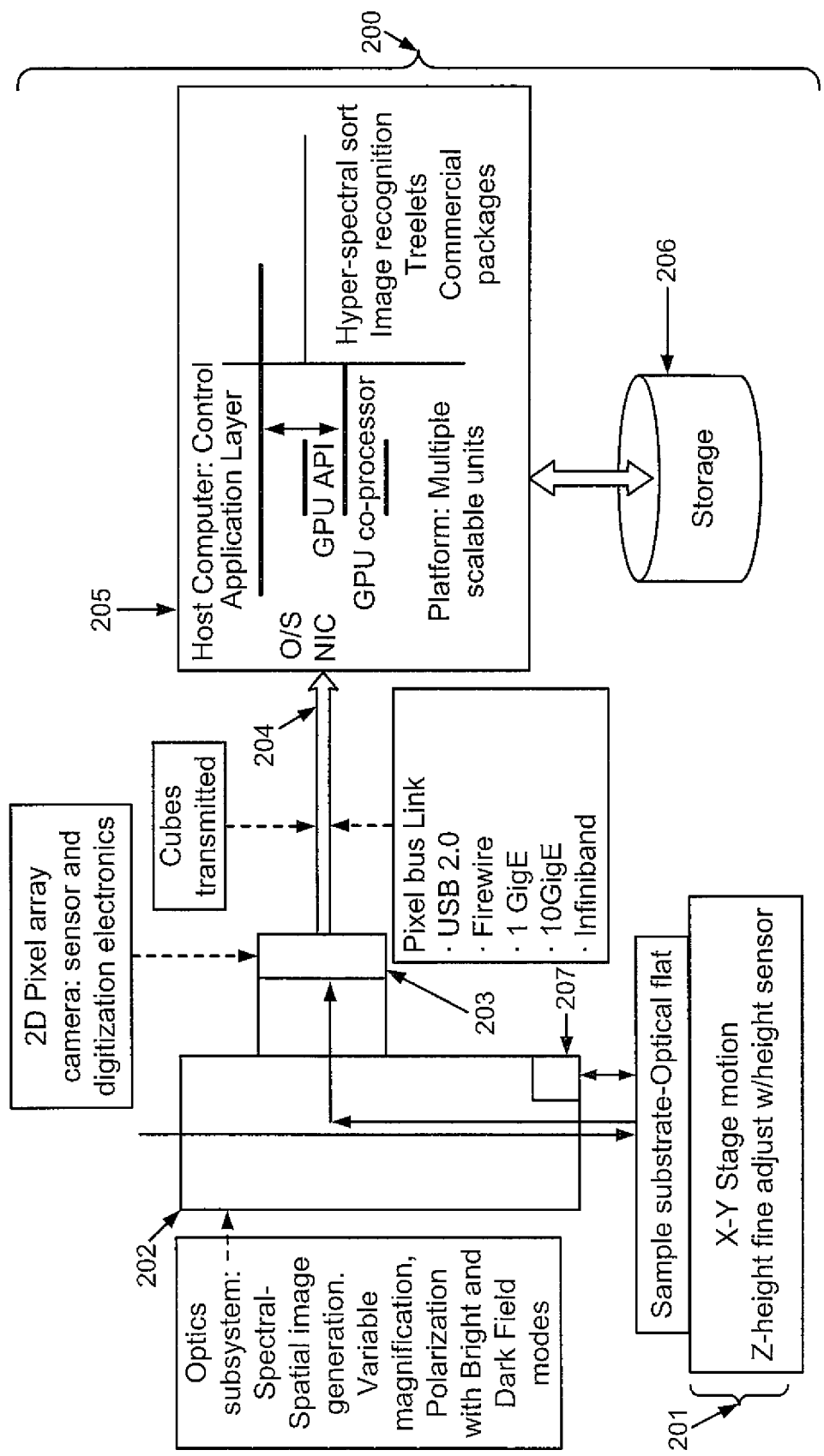
FIG. 2 is a schematic diagram of one possible embodiment of a system, such as a system for image rendering or spectral recognition, in accordance with claimed subject matter.

The term "computing platform" or "computing device" as used herein refers to a system or a device that includes the ability to process or store data in the form of signals. Thus, a computing platform or computing device, in this context, may comprise hardware, software, firmware or any combination thereof. Computing platform 205 as depicted in FIG. 2, is merely one such example, and the scope of claimed subject matter is not limited in these respects. For one or more embodiments, a computing platform or device may comprise any of a wide range of digital electronic devices, including, but not limited to, personal desktop or notebook computers, laptop computers, network devices, cellular telephones, personal digital assistants, and so on. Further, unless specifically stated otherwise, a process as described herein, with reference to flow diagrams or otherwise, may also be executed or controlled, in whole or in part, by a computing platform or device.

The terms, "and," and "or" as used herein may include a variety of meanings that will depend at least in part upon the context in which the terms are used. Typically, "or" if used to associate a list, such as A, B or C, is intended to mean A, B, and C, here used in the inclusive sense, as well as A, B or C, here used in the exclusive sense. Reference throughout this specification to "one example" or "an example" is intended to mean that a particular feature, structure, or characteristic described in connection with the example is included in at least one example of claimed subject matter. Thus, the appearances of the phrase "in one example" or "an example" in various places throughout this specification are not necessarily all referring to the same example. Furthermore, the particular features, structures, or characteristics may be combined in one or more examples. Examples described herein may include machines, devices, engines, or apparatuses that operate using digital signals. Such signals may comprise electronic signals, optical signals, electromagnetic signals, or any form of energy that provides information between locations.

In at least one embodiment, relatively fast spectral detection or relatively accurate recognition methods may be combined using pre-identified categories with an apparatus to support relatively high bandwidth processing, as explained in more detail later. Therefore, at least one embodiment of claimed subject matter may be generally applicable to fields that use flow or laser scanning cytometry to categorize cells, intracellular bio-entities or other populations, for example. To relatively rapidly detect or relatively accurately categorize relatively large microscopic distributions has at times been useful in medicine, biotechnology, or materials science. Methods to identify rare cells in blood or bone marrow may be applied to hopefully improve diagnostic capabilities or medical outcomes for patients.

Detecting circulating tumor cells at low cell concentrations or fetal cells in maternal circulation are two areas of active research. Advanced methods to identify rare cells in blood may hopefully improve diagnostic capabilities or medical outcomes for patients. In some cases, perhaps, even invasive medical procedures may be replaced with peripheral blood tests, which may be more desirable in some circumstances.

Flow cytometry in the past has been a useful tool for studying cell populations or intracellular processes via use of fluorescent tags, for example. Illumination or detection wavelengths have been extended over time to increase range of usable fluorophores. Typically, these tags may attach to cell surfaces and in some cases to intracellular entities.

Detection of cell populations via flow cytometry has improved medical care over time. Detection of residual disease has in some circumstances been a useful predictor of outcome in patients with hematologic (blood) malignancies and is currently being used to tailor therapy for children or adults with acute lymphoblastic leukemia, for example.

Advanced methods to identify rare cells in blood may improve diagnostic capabilities or medical outcomes for patients. One benefit may be, as alluded to, that invasive medical procedures could potentially be replaced with peripheral blood tests.

However, reliable detection or isolation of low cell concentrations for clinical use remains a challenge. Flow cytometers have been employed to accurately examine cells at rates up to approximately 7,000 cells/sec. In some cases, cytometer flow rates may be increased to 35,000 events/sec, but this may result in a 20% loss of sorted subsets due at least in part to event coincidence aborts, for example. Unfortunately, a 1% measuring precision may constrain rates to <10,000 cells/sec with a detection limit of a few hundred fluorescent molecules per cell. Sorting through $5 \times 10^9$ total cells to find 5 rare cells implies a flow cytometer in which $5 \times 10^9 / 7 \times 10^3 = 7 \times 10^5$ sec=200 hours of cell processing takes place. Thus, flow cytometry may be too slow for advanced rare cell detection in a reasonable amount of time, e.g., 1 part per billion in less than one day.

Some limitations might be addressed at least in part by enriching a sample prior to measurement. For example, a Veridex patent e.g., U.S. Pat. No. 6,365,362, issued on Apr. 2, 2002, titled Method and reagent for the rapid and efficient isolation of circulating cancer cells, by Terstappen; Leon W. M. M. (Huntingdon Valley, Pa.), Rao; Galla Chandra (Princeton, N.J.), Uhr; Jonathan W. (Dallas, Tex.), Racila; Emilian V. (Dallas, Tex.), Liberti; Paul A. (Huntingdon Valley, Pa.), assigned to Immunivest Corporation (Wilmington, Del.) Board of Regents, The University of Texas System. (Austin, Tex.), discloses magnetic separation processes for isolation of circulating cancer cells. Laser scanning cytometry may be further enhanced by use of appropriate detector configurations where scatter or absorption images may be combined with fluorescence image data in real time. Likewise, in some systems, cells may be distinguished by morphology, in which laser scanning cytometry or a computer-assisted image recognition method may be applied. However, scanned laser image formation combined with computer-assisted spatial recognition methods may limit processing rate to about 30 cells/sec.

In a typical system, laser scanning may employ deflecting a source across a sample. A stage may be moved in a stepwise fashion and images may be built up or constructed from a raster scan. Scanned multi-beam laser brush optics may be applied to increase rates by exposing more pixels in parallel. However, scanned laser optics and system synchronization may become more complex and expensive.

In one potential embodiment, however, a broad area illumination may be applied to enable high throughput by parallel or highly parallel pixel exposure. By emphasizing spectral recognition over spatial imaging for sensitivity and throughput, effects associated with diffraction may be ameliorated at least partially. Coherence effects in broad area illumination may be enhanced in diffraction-limited imaging systems and may become acute with high brightness sources in a narrow spectral emission range at shorter wavelengths, e.g. laser-based ultraviolet (UV) optical imaging systems. In contrast, use of visible light to limit specimen damage and broad-band illumination to obtain spectra away from the diffraction limit may reduce fringe visibility, speckle, or other coherent effects.

In addition, spatial image recognition methods may be limited in speed at least in part from processing time related to computational complexity. Spectral processing depending at least in part on how employed may provide some benefits in at least one embodiment.

Fluorophores may enhance detectability in flow cytometry or spatial contrast in fluorescence microscopy. Sub-resolution entities may be detected given sufficient signal to noise in various environments. However, it may be desirable to study cell function without use of exogenous labels to reduce or avoid chromatographic damage of cells, loss of genetic material, or otherwise influence cell function. Unfortunately, typically, without use of fluorophores or other exogenous compounds, detection sensitivity is low. Nonetheless, again, in at least one embodiment, spectral imaging methods may be applied with potential benefits whether fluorophores are used or not.

Multispectral microscopy is becoming more available. Apparatus using tunable filters, optics and a digital megapixel camera may, for example, be integrated in a device that mounts on a microscope. Spectral ranges may, for example, be selected to span 420 to 720 nm (visible) or 500 to 950 nm (in-vivo imaging). For example, a system may be used for bright field, non-fluorescence microscopy.

Confocal microscopy refers to an optical imaging technique that may be used to increase contrast by using a spatial pinhole to address out-of-focus light in specimens, which are thicker than the focal plane. Confocal microscopy also may employ some type of scanning to form an image. Stage scanning is possible but may be relatively slow compared to laser scanning. Confocal microscopy has also been employed to reconstruct three-dimensional images Confocal Light Absorption and Scattering Spectroscopic (CLASS) microscopy has been employed for cells having low contrast. CLASS apparatus may be applied to result in non-invasive detection of fetal nucleated red blood cells (fNRBC), which may be distinguished from adult nucleated red blood cells aNRBC by observing differences in spectral characteristics, e.g., in an intensity versus wavelength spectra. Differences in spectral characteristics of cells and sub-cellular organelles have been detected using similar apparatus without tagging, fixation, or risk of cell damage, as illustrated by FIG. 1 (from "Light-scattering spectroscopy differentiates fetal from adult nucleated red blood cells: may lead to non-invasive prenatal diagnosis." K-H. Lim, S. Salahuddin, L. Qiu, H. Fang, E. Vitkin, I. Ghiran, M. Modell, T. Takoudes, I. Itzkan, E. Hanlon, B. Sachs, and L. Perelman; May 1, 2009/ Vol. 34, No. 9/Optics Letters; pp. 1483-1485), for example.

Fetal nucleated red blood cells (fNRBC) make up a small fraction $1:10^9$ of circulating cells during pregnancy. NRBC are therefore rare in normal adult circulation, but during pregnancy maternal, adult nucleated red blood cells (aNRBC) exist and may interfere with detection of fNRBC having similar concentrations 1:1~100 fNRBC to aNRBC. Fetal nucleated red blood cells (fNRBC) may occur with about 1 part per billion in circulation. A 1 mL (milliliter) sample volume may thus capture about five fNRBC. This number of rare cells is consistent with another independent study.

It is noted, however, that for purposes of distinguishing cell type, confocal imaging may not necessarily be required. Spectral characteristics of different rare cell types may be distinguished without requiring optics set at intracellular or submicron resolution in accordance with the Rayleigh diffraction limit, for example. Some research has shown visible light spectra may be used to differentiate untagged cells. However, to be clear, the study did not address the problem of rare cells detection from a peripheral blood test. Instead, fNRBC was obtained from fetal umbilical cord blood and aNRBC from bone marrow.

Confocal Raman microscopy is another available method for studying molecular structure or chemical composition at localized volumes within a sample. Optical trapping with laser tweezers has further refined this method to allow reagentless identification of various bio-entities at relatively high resolution. Feasibility was shown for incorporating this technique in combination with a flow cytometry type scheme in which intrinsic Raman signatures of particles may be used instead of or in addition to fluorescent labels. Raman imaging, however, typically employs a high average incident laser power due at least in part to a small scattering cross section, which may result in relatively long exposure times, such as on the order of minutes/cell, for example.

Higher exposure rates compared to the above-mentioned spontaneous Raman excitations, however, may be achieved using multiphoton vibrational excitations based at least in part on coherent anti-Stokes Raman Scattering (CARS). For example, scanned laser sources may be used with multiplexed CARS micro-spectrometry to reduce sample times, if desired. However, a four-wave mixing process may involve more complex optics to acquire multi-photon vibrational spectroscopic information.

Regardless of particulars, a system may be employed to digitally render images and categorize results using spectral recognition methods. Reasonable or high throughput spectral category recognition is desirable, however, for rare cell detection from peripheral blood samples. To proceed from detection to automated recognition also may involve use of methods by which test samples are to be compared to a standard with differences scored and results categorized to aid in recognition.

Spectral recognition or spatial imaging may typically employ a complex set of methods to achieve reasonably accurate results or reasonable throughput for automated detection/categorization. Different parameters may apply to detection or recognition of spectral characteristics compared to an approach involving spatial imaging, for example. Signal to noise effects on spectral sensitivity may; for example, be a factor, which may be balanced with those affecting spatial point spread functions and contrast via a modulation transfer function to provide desirable results.

A systematic approach to achieve reasonable or high throughput while also providing reasonable accuracy may be handled in one embodiment through application of sub-systems operating in synchrony along with an approach in which work flow is integrated with feature set, as described in more detail below. It may be delicate to successfully achieve reasonable accuracy along with reasonable throughput processing with a set of disparate complex systems interacting through a variety of mechanisms. Hence, accomplishing or maintaining a delicate balance of competing factors involves novel and inventive arrangements.

In general, in at least one embodiment of claimed subject matter, reasonably large populations or distributions may be reasonably rapidly and reasonably accurately measured by a system in which components may include optical elements, stage mechanical elements, signal path components and a host controlling computational/logic device, which may include spectral-spatial recognition processes to be performed in real-time. In at least one embodiment, system throughput or run time may therefore be affected at least in part through coordinated operation, as shall be explained in more detail below. In at least one embodiment, for a system operating in an acceptable manner, a relatively fast sample examination with acceptable recognition accuracy may be accomplished.

In at least one embodiment, a system may be employed to achieve reasonable or high throughput with automated sample detection and provide relatively accurate characterization, independent of, or in conjunction with, a variety of sample preparation techniques. In at least one embodiment, samples may be examined without use of exogenous labels, although use of exogenous labels is not necessarily excluded for other embodiments. Likewise, an embodiment system may also operate with pre-processing in which sample enrichment methods may be applied to further enhance accuracy, throughput, or both. In some cases, enrichment processes may be simplified or omitted, of course. Likewise, a wide variety of fluorophores, magnetic particles, quantum dots or other exogenous tags may be used, although, it is not intended that claimed subject matter be limited in scope in this respect. Likewise, claimed subject matter is not limited in scope with respect to frequency dispersion characteristics of a particular medium or by sensitivity of a particular recognition process to signal to noise distributions. Claimed subject matter is intended to contemplate all possible variations that may provide desirable results.

For purposes of discussion or illustrations, but without intending to limit the scope of claimed subject matter in any way, assume that initially a sample is dispersed as a thin film on a flat substrate and is examined with broadband light. Again, this is provided as an illustration and is not intended as a limiting example in any way. For one embodiment, assume reflective substrate optics with a beam splitter may be used. Likewise, for a second embodiment, assume transmission substrate optics without a beam splitter may be applied.

In at least one embodiment, selected portions of bright broadband visible light may be applied to sequentially expose a sample object field using Kohler illumination, for example. For example, in at least one embodiment, an arc lamp or a super continuum laser may serve as a broadband light source. A liquid crystal or acousto-optic tunable filter may be employed in at least one embodiment to create a sequential series of frequency bands for illumination at selected wavelengths. This may be accomplished using any one of a variety of techniques and claimed subject matter is not limited in scope to any particular approach. It is likewise noted here that in at least one embodiment wide field illumination has benefits including that it may reduce risk of sample damage from high light flux that might otherwise occur since flux would be dispersed over a region. Likewise, in at least one embodiment, visible light optics may reduce risk of destructive observation of a thin film sample which might otherwise occur if ionizing radiation were employed.

In at least one embodiment, if conjugate detection optics is employed, collected light may be transferred to a photoelectric sensor array, which may image a sample-object field. For embodiments employing elastic scattering (e.g., in accordance with Mie Theory) or weak absorption (e.g., in accordance with Beer-Lambert law), additional tunable filtering may be omitted, if desired. However, for an embodiment in which fluorescence detection or other resonant absorption may be employed, such as associated with Raman scattering, a second tunable filter may in some instances may be included, if desired, to potentially improve signal to noise by limiting the range of collected wavelengths, for example. Likewise, in at least one embodiment, transfer optics may be interposed with spatial filters, which may be employed to create bright and dark field imaging or alternate spectral detection modes. It is, of course, understood that these specifics regarding potential optical arrangements are provided merely to be illustrative and claimed subject matter is not limited in scope to employing any particular approach. A range of possible approaches exist and which approach to employ may vary with a variety of factors, such as cost, convenience, performance along particular parameters of interest, etc.

In at least one embodiment, a sensor array along with relatively low noise analog to digital electronics may be employed to generate a pixelized set of frame digital signals corresponding to respective wavelength bands. For example, without limitation, in an embodiment, a charge coupled device (CCD) or a complementary metal-oxide-semiconductor (CMOS) sensor array may be used. Likewise, low noise electronics may digitize the signal and interface to a signal link, as shall be described in more detail below.

A relatively high bandwidth signal link may be employed to transmit frames to a computing device, such as a host computer, for example, which may, in at least one embodiment, be employed to coordinate spectral or spatial recognition processes for fast rendering or categorization of pixelized spectra. Devices for substrate handling or stage motion control may likewise be employed to sequentially position a sample within an optical field of view and to generate image field coordinates to be used in conjunction with image processing. In combination, therefore, in at least one embodiment, a computing device or platform may provide computational and logic services, which may be applied, for example, to synchronize substrate motion with imaging capture to meet or exceed rates of signal processing desired so that rare cells may be detected in a reasonable amount of processing time, e.g., approximately in the range of 8-16 hours or even less, such as 12 hours.

Although claimed subject matter is not limited in scope in this respect, in at least one embodiment, spectral recognition may be employed in a number of approaches. Therefore, it is not intended that claimed subject matter be limited in scope to a particular approach to spectral detection. The following two examples are provided simply for purposes of illustration. Many other spectral or spatial recognition or detection approaches other than these simple examples may be applied and are intended to be included within the scope of claimed subject matter.

For example, in one possible approach, a relatively fast or quick spectral detection may precede a more in-depth spectral or spatial detection. Fast spectral detection may correspond to a low magnification involving relatively speaking larger image pixels and high depth of focus. Spectral recognition may therefore be applied initially to exploit potentially faster and parallel processing, which may be followed by spatial imaging methods. Thus, higher resolution spectral analysis or spatial imaging may be applied in a second pass. Specific fields identified as of interest from a first pass may be revisited using smaller pixels by changing optics magnification. Subsequent second pass examination is feasible if a few fields are of interest even though the time per field is increased. Likewise, or alternatively, image reconstruction may be applied with stored frame signals. Additionally, in an embodiment, spatial recognition processes may also be applied to sorted or identified pixels associated with categories of interest.

In a separate approach involving spectral detection, detection or categorization may be applied during separate or independent phases. For example, offline from a particular scan of a particular sample, for example, a training phase may be conducted in which an expert may be employed to associate a spectral signature with a category of interest. A category of interest, without limitation, may correspond to a cell, intracellular component, or other entity, for example. Various approaches may be employed to deduce or generate a spectral signature to be associated with a category of potential interest. For example, without limitation, simple averages, principal component analysis, treelets, Fisher discriminant scaling, or other known transformations of statistical distributions may be applied. In this manner, a host of possible spectral signatures representing categories of interest may reside in memory.

Likewise, in at least one embodiment, during a scan of a sample, which may take place subsequent to generation of possible spectral signatures, spectra associated with a sample under test may be generated. Sampled signals for the particular sample under test may, therefore, be compared with stored spectral signatures via a scoring metric, for example. A comparison or a scoring calculation may assist in identifying samples under test that may belong to a given category of interest.

Although claimed subject matter is not limited in scope in this respect, in at least one embodiment, reasonable or relatively high throughput with reasonable or relatively high accuracy may be realized than other might be available with other state-of-the-art cytometry methods, as explained in more detail below. For example, in at least one embodiment, automated category recognition of detected sample images may be processed using various spectral or pattern recognition processes. Likewise, in at least one embodiment, relatively low noise spectral library characteristics may be employed using a variety of approaches, such as using treelets or other compressive sensing methods. Spectral recognition from a real-time scan of a sample may also yield spatial images that are able to be associated with predefined categories in some situations. Thus, in at least one embodiment, rare cells may be detected, identified, or categorized with scanned signals of a sample stored for later use.

In what follows, a variety of aspects of at least one embodiment are discussed primarily for purposes of illustration. It is, of course, understood that claimed subject matter is not intended to be limited to this particular embodiment or illustrative example, or to any particular embodiment or illustrative example provided. Many other variations are possible and those other variations are intended to be included within the scope of claimed subject matter. However, it is believed that providing one or more non-limiting illustrative examples will be useful to aid those of ordinary skill to understand to greater depth the larger richness that is present for various inventive aspects of subject matter that is claimed.

FIG. 2 is a schematic diagram illustrating one embodiment 200 of a system in accordance with claimed subject matter. As illustrated, embodiment 200 comprises a variety of components including: a system 201 for mechanical handling of a sample substrate, an optical system 202, which for this particular embodiment includes digital pixel array sensor, associated analog to digital electronics 203, a signal transport or link 204, a computing device or computing platform, such as a host computer 205, with a storage device 206, and a substrate height sensor 207. Of course, this is merely an illustrative embodiment or example and claimed subject matter is not intended to be limited to this example or embodiment. For example and without limitations, other embodiments in accordance with claimed subject matter may include these elements, may include additional elements, may include substitute elements or may omit various elements.

In at least one embodiment, relatively thin films of blood, biological suspensions, or other entities, to provide a few examples out of many possibilities, may be dispersed on or over a substrate that in at least one embodiment may be optically relatively flat. Of course, other types of surfaces are possible. A benefit of dispensing or dispersing a sample over a surface, as discussed in more detail below, is that large populations of cells may be examined in a parallel fashion, thereby improving throughput, if components of a system are appropriately coordinated.

Continuing, in at least one embodiment, cells or other population distributions may be dispensed or dispersed in a form to be examined in more detail using an optically relatively flat surface. Substrates such as a semiconductor wafer, quartz blank, glass slide or other surfaces capable of being optically flat relatively therefore may be used, although many others are also available. For example, a 0.7 ml sample of a substance, such as, for example, blood, may be spread over a 300 mm wafer. In this non-limiting example, therefore, a sample may have an average 10 um film thickness. This is, of course, provided as merely an illustrative example and it is not intended that claimed subject matter be limited in any way to these amounts, volumes, thicknesses, etc. Nonetheless, this simple example corresponds to a potentially workable cell size and a potentially workable depth of focus range.

A variety of approaches to dispensing or dispersing a sample so that it may be suitable for scanning or examination exist and claimed subject matter is not intended to be limited to any particular approach or technique. A few approaches are discussed here as illustrative examples or embodiments, although it is not intended that claimed subject matter is be limited in any way to these few illustrative examples. One example approach or embodiment includes a technique at times referred to as spin coating. Using spin coating, a fluid suspension may be applied to an optical flat so that a sample to be scanned for in-depth image rendering may be dispersed across an optical flat. Spin coating is a well established technology that typically dispenses a sample in liquid form onto a spinning substrate with programmable rotation speeds so that the sample is relatively uniformly dispersed across a substrate area. Although spin-coating has, for example, been employed in other areas, substances involved, such as photoresist, for example, and processing objective, to protect underlying materials from application of caustic substances, such as an acid bath, for example, may imply a different or additional set of considerations, as discussed in more detail below.

Another second approach or embodiment might employ ink jet methods to reasonably or substantially uniformly deposit a sample on a substrate. In this case, a sample may be dispensed as a liquid or aerosol in a substantially uniform rectilinear motion, again with an objective of relatively uniform thin film thickness resulting across a substrate.

Still a third way might use a micro-fluidic technique for sample segregation. In this case fluids may typically be dispensed from a periphery via channels, which may form flow paths across a substrate.

Returning, for example, to spin coating as a potential technique for at least one embodiment, depending at least in part on the particular sample fluid, its viscosity, as well as other properties, may be factors to consider. Using blood as one illustrative example, without intending to limit the scope of claimed subject matter, blood has a viscosity approximately in the range of 1~100 cP. This may be comparable to viscosity of a conventional photoresist, for example. However, being organic, blood, continuing with this simply as one example, may introduce more complex considerations to be addressed.

For example, blood is known to exhibit non-Newtonian behavior. Blood plasma, for example, has a viscosity about 1.8-times the viscosity of water at 37° C., although protein composition of the plasma may affect this as well. Whole blood, on the other hand, has a relative viscosity of 3 to 8 depending at least in part upon percentage of hematocrit and at least in part upon temperature.

It is noted that while more typically spin coating or similar processes may be applied as an operation or sub-operation to result in an inexpensive way to manufacture a part, for example, in this context, by way of contrast, it is desirable to have a capability to examine large populations of cells reasonably rapidly and reasonably accurately. In some cases or embodiments, it may acceptable to use a blood biocompatible solution, such as Dextrans, to modify optical or physical properties (e.g. viscosity, absorption or transparency) to conveniently affect results, typically in the form of signal to noise (s/n) for spectra or contrast for imaging applications. In other cases or embodiments, microfluidic devices may be used to extract or separate components of interest before sample measurement. See, e.g., "Microfluidic chip for blood cell separation and collection based on crossflow filtration" Xing Chen, Da Fu Cui, Chang Chun Liua and Hui Lia; Sensors and Actuators B: Chemical. 130, 216-221, 2008 and "Passive microfluidics devices for plasma extraction from whole human blood" E. Sollier, H. Rostaing, P. Pouteau, Y. Fouillet and J-L. Achard; Sensors and Actuators B: Chemical 141, 617-624, 2009, of course claimed subject matter is not limited to these example approaches or embodiments.

In general, for at least one embodiment, one may assume a full or complete amount of a sample is to be examined during a processing run, unless other knowledge is available about locations of cells or intracellular components of interest within a given sample that may suggest that on a particular region is to be examined rather than a full sample, for example. Assuming that a sample has been reasonably uniformly spread across a substrate, as may be desirable for scanning or examination by a system, a stage 201, for example, in at least one embodiment, may be employed to move a sample-substrate in an X-Y plane as shown, for example, by FIG. 2, as being reasonably perpendicular to and going into the plane of the page, relative to optics 202 which is shown as being reasonably parallel to the plane of the page. A Z-axis, also reasonably parallel to the plane of the page, may likewise define an optical axis. Z-height control of stage 201 may further include various mechanisms so that adequate signal/noise or depth of focus may be achieved during sample processing in at least one embodiment.

For example, in at least on embodiment, a substrate may be held in place with vacuum pin chucks. Likewise, a substrate height sensor 207 may be employed so that a reasonably adequate depth of focus may be maintained during processing. Open or closed loop control systems may be employed in an embodiment, for example, so that variation in height during processing is within tolerable limits to accomplish desired cell examination, such as on the order of the optics depth of focus, e.g. 1~10 microns. Thus, although claimed subject matter is not limited in scope in this respect, for at least one embodiment, depth of focus optics, if desired, may omit complex electro-mechanical operation while an acceptable margin for potential variations in sample thickness is capable of being allotted.

In an embodiment, stage-sample coordinates for any given position may be are read out any one of a number of ways. As examples, an encoder may generate coordinates or a laser interferometer may be used and generate signals to be stored with obtained pixel frame signals so that one may return to image fields of interest for further study. Likewise, computer or computing device 205 may include control software to coordinate stage control with signal acquisition.

In at least one embodiment, stage and substrate may move in synchronized placement, illuminate and detect sets of actions to sequentially place a series of sample object-fields within an optical field of view. Optics to illuminate or detect may be arranged to establish an object-field for a sample substrate. In at least one embodiment, after sample object-field illumination across a band of wavelengths, for example, a stage of a system may subsequently move a sample to a next field location where an illumination, imaging and detection process may be repeated.

Stage throughput may vary in accordance with a variety of parameters. Some parameters that may affect throughput may include "dwell time" per field, which may be affected by photon flux or number of wavelength bands being applied to a sample. Likewise, object-field size or frame rate may also affect throughput. Time for motion between placements likewise may affect throughput. Although claimed subject matter is not limited in scope in this respect, to assist throughput, it may be desirable to arrange a system so that time for motion between placements may be less than around 10% of the total time to illuminate and collect signals for a single placement location, including illumination across multiple bands of wavelengths.

Figure 3:
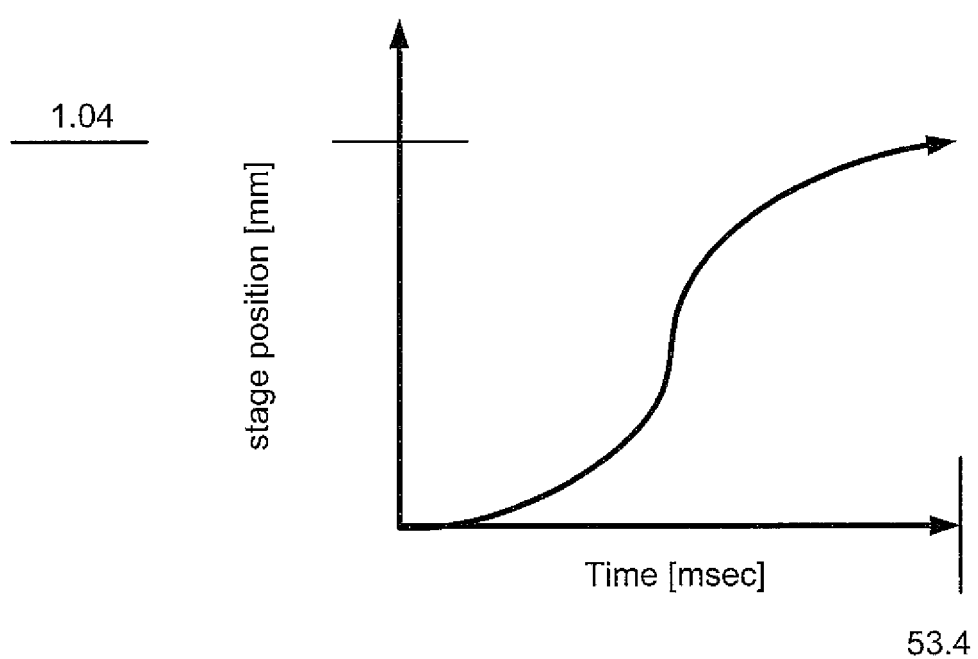
FIG. 3 is an example plot showing for one potential embodiment stage position versus time.

FIG. 3 is a plot showing example stage motion for a possible system. FIG. 3 suggests that in at least one embodiment a capability of 750 mg acceleration and 400 mm/sec velocity may be workable from the discussion above. For example, FIG. 3 illustrates that a stage may be halted for at least 534 msec for 8 exposures at 66.7 msec/exposure for a 15.1 frame/sec camera rate. Likewise, the plot illustrates 53.4 msec may be budgeted for stage motion to a next image field 1.04 mm away. By accelerating to 150 mg and reaching midway at 0.52 mm, a stage may then decelerate to a next image field, for a 1 um image-field pixel size. Of course, this is merely one illustrative example and claimed subject matter is not limited in scope to this example. This information is provided merely to illustrate an approach that may be implementable; nonetheless, may other implementable approaches are possible and it is intended that they be included within claimed subject matter as well.

Figure 4:
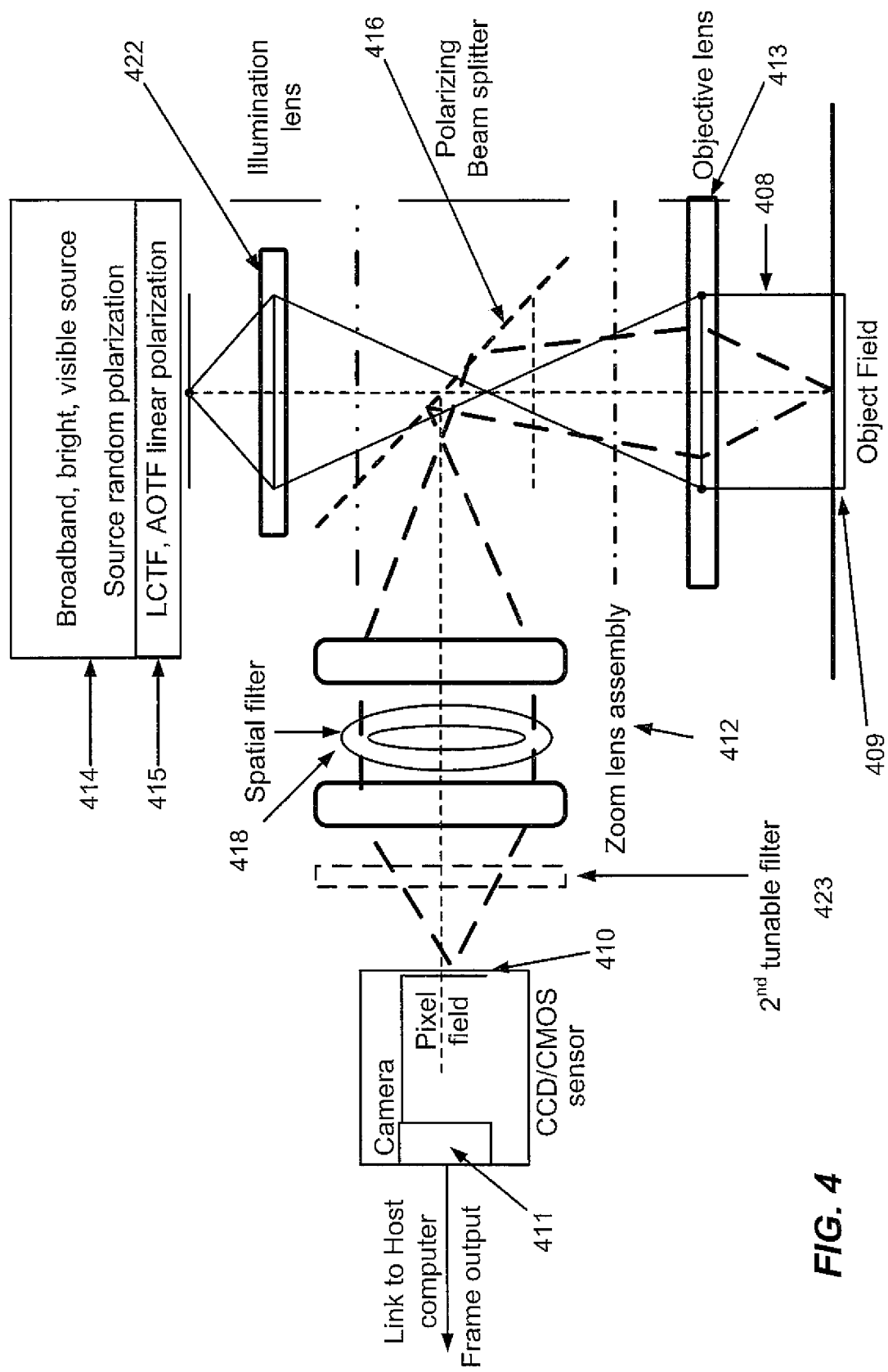
FIG. 4 is a schematic diagram showing an embodiment of optics system 202 of FIG. 2 in greater detail.

FIG. 4 is a schematic diagram showing an embodiment of optics system 202 in greater detail. Embodiment 202 may, for example, employ Kohler illumination 408 (e.g., solid lines) to nearly uniformly expose a sample object-field 409. A collection optics branch (e.g., dashed lines) may be arranged in a manner so that illumination of an object-field may be transferred to a pixel array sensor 410. In at least one embodiment, a sensor array may be combined with electronics for low noise, for high frame rate output digitization or both, illustrated by 411; although, of course, claimed subject matter is not limited in scope in this respect. In an embodiment, a ratio of object-field to camera sensor-pixel size may be set by zoom lens assembly 412 and objective lens 413 magnifications. Sensor pixel array 410 may in at least one embodiment be optically conjugate to sample object-field 409, if desired. Effective pixel size at a sample object-field may therefore be determined at least in part from sensor pixel size and lens magnifications for an embodiment.

As suggested previously, in at least one embodiment, sample object-field 409 may be nearly uniformly illuminated with a source 414. In at least one embodiment, a source may emit light in approximately a visible wavelength range, such as around 400~800 nm, although, of course, claimed subject matter matter is not limited in scope to employing only visible light.

Bright broadband light illumination may be employed for spectral detection in at least one embodiment, although, again claimed subject matter is not necessarily limited in this respect. One example embodiment may use a Supercontinuum laser. This type of laser may include a capability to generate a relatively wide range of frequencies over a visible spectrum with acceptable or high spectral density by generating pico-second pulses. For example the results provided below use the specifications of the following supercontinuum laser product reference: Fianium New product data sheet January 2010. http://www.fianium.com/pdf/sc-400-450.pdf. A more general description of principles of operation may be found in *The Supercontinuum Laser Source: Fundamentals with Updated References*, ed. by R. R. Alfano. Springer 2006. Of course, claimed subject matter is not limited in scope to using a Supercontinuum laser or the foregoing product.

In an alternate embodiment, an array of laser diodes may be coupled with an optical multiplexor used as a pump module to drive a fiber laser. Fianium Corporation comprises one example of a commercial vendor for equipment. Available specifications for Fianium equipment have been used at times herein to calculate an estimate of performance, although, of course, claimed subject matter is not limited to these illustrative calculations or to use of Fianium equipment. In an embodiment, a 500-700 nm spectral bandwidth may be generated from a 100 psec master pulse having a 1 MHz repetition rate. In an example, a spectral density of 1 nJ/nm (2 W power output) or 3 nJ/nm (6 W power output for model SC450-6) may result. For randomly polarized light, power output may be around 1 mW/nm or 3 mW/nm, respectively. Again, these are illustrative examples.

In at least one embodiment, a light source, such as a broadband laser, for example, may be coupled with a liquid crystal tunable or acousto-optic tunable filter (AOTF) 415, which may be employed to select bands of wavelengths, such as bands of visible wavelengths, for example, over a time interval. In at least one embodiment, filters may provide relatively fast wavelength multiplexing generated from a broadband source. Number of bands may vary with a variety of factors; however, a typical range for at least one embodiment may be from 8 to 28 separate bands, for example. Therefore, in at least one embodiment, a broadband source with tunable filters may be employed to provide desired multi-spectral sample illumination for generation of spectra.

It may be convenient to place a tunable filter near a source so that illumination by unused wavelengths is less likely to occur, for example; however, in an alternate embodiment, it may be desirable to locate a second tunable filter after a sample near a camera or similar device to capture or collect light, for example, as a technique to detect inelastic processes or further subdivide bands of light, if desired. Again, these are simply examples without limitation and are not therefore intended to limit the scope of claimed subject matter.

Object-field 409 on or over a planar sample-substrate may be sequentially illuminated over a range of wavelengths generated by a light source and a tunable filter 415, for example. As laser light, for example, in an embodiment employing a laser, is randomly polarized and filtered light from a tunable filter is linearly polarized, approximately a 50% loss in power may occur.

In at least one embodiment, a polarizing beam splitter 416 may be used to separate generation from collection, as previously suggested above, for example. This relates to the dashed versus solid lines mentioned above. Of course, again, this is merely an example, so it is understood that claimed subject matter is not limited in scope to this particular example implementation. However, in at least one embodiment, light from two optical branches may be propagating across overlapping areas of space. It therefore would be useful to be able to direct them to appropriate locations. In this example, a polarizing beam splitter is useful therefore. A range of s-polarized light may be transmitted out of tuned filter 415, and a range of p-polarized light may be transmitted to a pixel sensor array. The particular amount depends at least in part on dispersion at a sample in object field 409.

As an example, filter 415 may be set to pass a $\Delta\lambda.=20$ nm band. Benefits of a tunable filter may include a faster response time to handle frequency ranges, for example. Transmission efficiency, as mentioned, may be about 50% due at least in part to passing one type of polarized light (e.g., s-type or p-type). Of course, this is only one particular embodiment and claimed subject matter is not limited in scope to this particular feature, as mentioned. That is, a variety of features is possible and is intended to be included within the scope of claimed subject matter. However, combined assembly as just described is expected to produce polarized light with 10 mW to 30 mW per band if source laser power output corresponds to 2 W or 6 W, respectively.

Typically, reflection efficiency, dispersion, or polarization may depend at least in part on the particular sample being examined or scanned. To provide an illustrative quantitative example, not intended to limit the scope of claimed subject matter, the following may be assumed for illustrative purposes. Assume 10% of s-polarized light impinging on a sample may be reflected as p-polarized light, which may then be reflected by a beam splitter and transmitted to a pixel array. Under these example conditions, 1 mW may be transmitted to a sensor if a laser provides 2 W of power.

In at least one embodiment, a large axial focus tolerance (e.g., a relatively large depth of field) may result from use of a relatively low magnification spectral detection optic, which may allow light captured from a sample sufficient depth within an object-field pixel. For example, in at least one embodiment, 6× magnification for optics collecting light may correspond to a 1 μm sample object-field pixel imaged to a 6 μm sensor pixel with about 10 μm depth of field.

In a case or embodiment where illumination wavelength differs from that detected, e.g. inelastic processes are measured, e.g. fluorescence excitation or Raman scattering, use of a second tunable filter 423 may improve signal to noise. Without its use, for example, a CCD array may collect a range of wavelengths including those of the source. A second tunable filter may assist as a type of notch filter or as a filter applied across a band including inelastic source illumination to block light having a wavelength that is not of particular interest.

Various commercially available low noise sensor arrays are available, such as from Kodak or Sony, for example, to provide only a few examples of possible sources. To provide estimates of performance, for example, specifications from a Sony ICX285 front-illuminated CCD are used, although, again, claimed subject matter is not limited to these illustrative examples, to employing a Sony product or to employing a product by any particular manufacturer. By sequentially tuning filter 415 and exposing sensor 410, signals for images may be acquired at desired wavelengths, band by band, for example.

As an example, a sample object-field may be successively illuminated using light at eight wavelengths respectively. A frame of 1.45 Mpixels may be generated for a wavelength. A succession of eight frames of signals captured in this manner, for example, may comprise a imaging or image signal "cube" for a given image field.

Figure 5:
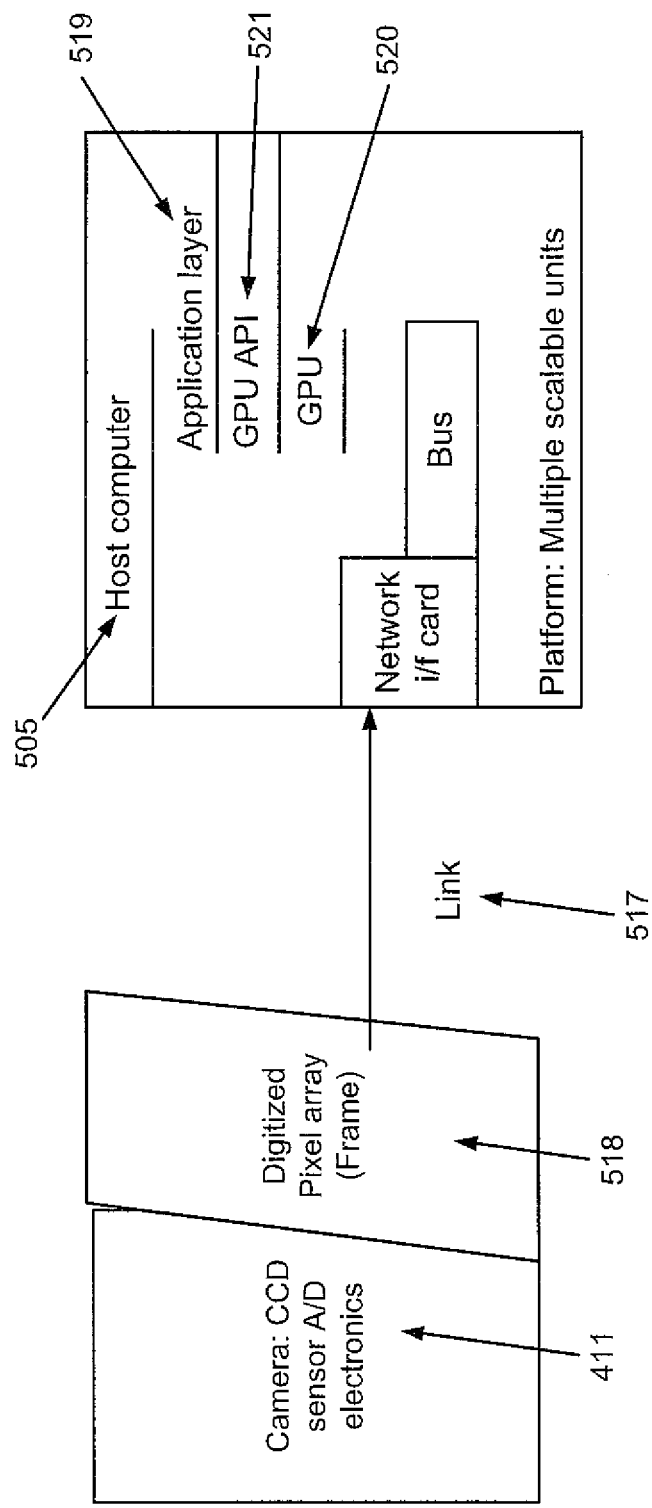
FIG. 5 is a schematic diagram showing an embodiment of host computer 505, signal link 517 and other components of FIG. 2 in greater detail.

In at least one embodiment, a digital CCD image capture device or camera may include analog to digital electronics 411 to operate at, for example, 15 frames per second, although claimed subject matter is not limited in scope to this example. Referring to FIG. 5, using 15 frames per second as an example, the frame rate may deliver a 14 bit/pixel digital output signal at a 30 MHz read rate, for example. In this illustrative example, a pixel rate may therefore be $2.2 \times 10^7$ pixel/sec where 15.1 frame/sec is provided with 1.45 Mpixels/frame. A signal link, such as 517, to communicate signals for one or more captured images, therefore, with bandwidth of 48 Mbytes/sec, or 380 Mbit/sec would be equivalent to 14 bit/pixel×$2.2\times10^7$ pixel/sec and would accommodate this amount of information. Commercially available signal links such as USB 2.0, Firewire, 1 Gig Ethernet, 10 Gig Ethernet, or Infiniband are capable of sustaining 50 MB/sec rates or greater, for example.

In an embodiment, detection sensitivity may be related to photon emission from a bright, broadband visible source, as well as sensor array and analog to digital noise characteristics. In an embodiment, source brightness and acceptance angle may at least in part affect number of photons/unit area that may illuminate a sample surface. Laser power, sample characteristics, or optics transmission efficiency may also at least in part affect quantity of photons impinging on a sensor array in an embodiment. Sensor quantum efficiency and analog-digital (A/D) electronics may affect at least in part detected signal to noise delivered in a form of frame image signals 518 to be transported via signal link 517 in at least one embodiment.

For at least one embodiment, to estimate photon emissions, assume their number is roughly constant over a visible range as given at a wavelength of about 500 nm, which has energy 2.5 eV=$4\times10^{-19}$ J. With these assumptions, photons may arrive at a rate of 1 mW/$4\times10^{-19}$J=$2\times10^{15}$ photons/sec. For a 50% quantum efficiency over 450-750 nm visible band, this example yields $1\times10^{15}$ electrons/sec. Therefore, with this assumptions, photoelectron current/pixel is $7\times10^8$ electrons/sec/pixel ($1.43\times10^6$ pixels/sensor)=$1\times10^{-10}$ amps/pixel. For an embodiment, employing Sony provided CCD sensor noise specifications for the ICX285 front-end illuminated CCD provides: full well=$1.8\times10^4$ e$^-$ (1×1 binning); read noise=12.3 electrons (per pixel at 30 MHz read rate) and dark current=0.015 electron/sec/pixel. For this example, a 30 MHz read or CCD refresh rate may yield 33.3 nsec collection time intervals. So signal (S) generated per pixel may be:

$$S = 7\times10^8 [e^-/sec*pixel] \cdot 3.3\times10^{-8} [sec] = 23.[e^-/pixel]$$

Under these conditions, for this example, dark current may be negligible for a 66.7 msec/frame duration. This may result in a dark noise level of $$N_{dark\ noise} = 7\times10^{-3}[e^-/sec*pixel] \cdot 6.7\times10^{-2} [sec] = 10^{-3} [e^-/pixel].$$

Under these assumptions, for at least one embodiment, signal to noise (S/N) may primarily be determined by read noise $$S/N_{read} = \frac{23}{12.3} = 1.9.$$

In an embodiment, if a higher power SC450-6 Supercontinuum model were used, which may deliver 3 mW/nm spectral power density, S/N of the system may increase $$S/N_{read} = \frac{69}{12.3} = 5.7.$$

Read noise may potentially be further reduced in an embodiment by running at 10 MHz read rate. This may reduce read noise to:

$$S/N_{read} = \frac{69}{5.5} = 12.7.$$

However, in the latter case, for an embodiment, frame rate may drop from 15.1 to 5.9 frame/sec, which may result in a 2.6× decrease in throughput. Test time may remain constant, however, if pixel size were to be increased. The device specified dynamic range 1463:1 at 30 MHz and 1×1 binning is actually slightly less than the specified 14 bits available since;

Dynamic range=Full well/Read noise=1463<$2^{11}$=2048 which instead implies an 11 bit effective resolution for this particular example embodiment.

It is noted that the calculations above are simply illustrative. In actual use, a variety of factors may affect performance. For example, signal or noise distributions combined with process categorization methods employed may at least in part affect practical pixel size or sampling speed for adequate spectral recognition or categorization.

Again, the calculations above employ specifications taken from the Sony sensor ICX285 front-illuminated, interline CCD. Of course, therefore, these calculations are to provide an illustrative example. Claimed subject matter is not limited in scope to these specifications or to employing a Sony sensor, for example.

For an embodiment, if object-field to camera-pixel array optics were set at a 6× magnification, this may result in a 1 µm diameter sample region comprising a 6.45 µm CCD-pixel in a sensor. A tunable filter may have 25 usec to 50 msec response, which may vary based on a variety of factors, include liquid crystal versus acousto-optic implementation. This may, in turn, drive a camera at 15 frames/see rate with full 1×1 bin resolution, potentially delivering 14 bits at 30 MHz. An object-field area corresponding to a 1 µm pixel may comprise 1.392 mm×1.04 mm=1.44 mm². A 300 mm diameter substrate may therefore cover $7 \times 10^4$ mm²/1.44 mm²=$4.8 \times 10^4$ fields in an embodiment.

For spectral detection using 8 wavelength bands, as one example, a sample field may be exposed for 534 msec=8 exposures×66.7 msec/exposure for a 15.1 frame/sec camera rate. An additional 10% of this time=53.4 msec may in an embodiment be budgeted for stage motion to a next image field 1.04 mm away. Thus, for at least one embodiment, a total time dedicated per field may be 588 msec; or equivalently 1.7 fields/sec. Thus, for at least one embodiment, as an example, a first pass throughput, may provide $4.8 \times 10^4$ fields/1.7 image-fields/sec resulting in a 8.0 hour throughput. Working with this example, but, instead, doubling pixel size may reduce throughput to 2.0 hours. Of course, throughput increased by larger pixel sizes may be balanced by spectral recognition accuracy. For an embodiment, run time throughput includes time for sample detection and stage travel time, as previously discussed.

In at least one embodiment, a low magnification optic may be employed so that relatively large pixels result. One potential benefit may be to produce a higher bandwidth stream of image signal cubes. For an embodiment, effective pixel size at a sample object-field may be affected by a variety of factors, including collection optics magnification or physical size of sensor array. While effective pixel sizes may result in faster operation in terms of higher bandwidth, for an embodiment, it may also affect s/n or categorization accuracy. Acceptable confidence levels may, thus, be determined at least in part by a particular use to which a system embodiment may be applied.

In at least one embodiment, FIG. 5 illustrates, for a camera or capture device, such as 411, a frame or digitized pixel array of signals, such as 518, may be transmitted or delivered to a host computer or other computing device, such as 505 via a link 517 with sufficient bandwidth. A host computer or similar computing device may coordinate or provide control among various subsystems to reduce potential bottlenecks at any particular point in an overall system embodiment. Real time signal acquisition, processing and storage may, for example, occur in a multi-threaded, multi-core processor environment, although claimed subject matter is of course not limited in this respect. For an embodiment, run time categorization or signal storage may write to a storage device 206 as shown in FIG. 2.

In an embodiment, a computing architecture may comprise commercially available multiple scalable units, if desired. Units may comprise, for example, multi-core processors, an operating environment, a file system and storage. Multi-core processors may comprise central processing units (CPU's). In one embodiment, processing may be accelerated in conjunction with a graphics processing unit (GPU), if desired, for fast parallel processing of pixel array signals. An operating environment may comprise an operating system, job scheduler and compiler. Of course, this is intended merely as an illustrative example. Many other types of architectures are possible and are intended to be included within the scope of claimed subject matter.

Long term storage of raw frame or processed signals is available from various commercial database vendors. It may be desirable to have a capability in at least one embodiment to handle 1.6 Terabytes of raw or unprocessed signals per sample at a steady state rate of 50 MB per sec. Typical individual disks may handle a sustained write of 20 MB/sec or a sustained read of 40 MB/sec. Therefore, in at least one embodiment, a multiple disk system may be desirable to support 50 MB/sec. Again, claimed subject matter is not limited in scope in this respect.

Spectral-image processes may reside in application layer software 519 on a host computer 505 or similar computing device, such as shown in FIG. 5. Received captured signals may be compared to category libraries that may be stored. Pixelized spectral signals may be rendered from image signal cubes into categories using processes, including some described below.

In at least one embodiment, spectral recognition that is capable of being relatively fast and relatively accurate is desirable. In at least one embodiment, one approach may comprise employing parallel processing supported by the manner in what images are captured, as described in more detail below. In at least one embodiment, multi-core CPU's and graphics processing units (GPU) that are commercially available may be employed to handle computation complexity and desired bandwidth for reasonable or high throughput operation.

Below, one possible approach is provided, although claimed subject matter is not limited in scope in this respect. Again, this example is provided primarily for purposes of illustration. For at least one embodiment, a spectral recognition process may compare a sample 8-wavelength vector per pixel to a single category using floating point operations. It is noted that for this particular embodiment, an image signal cube, as previously described, for example, may be arranged or structured so that for a pixel of a sample, eight vectors at respective wavelengths are present. A comparison calculation may involve, for example, for sum of components squared type comparison, 8 subtractions, 8 multiplies, and 8 additions. In this non-limiting example, therefore, 24 operations may be performed. For a sensor array which may yield 1.5 M pixel/frame, as an example, also using 24 operations/pixel may provide 37.5 M operations/frame. For this example, if we again assume 15 frames per sec, this implies 562.5 M operations/sec for this example. If we desire to perform calculations for 8 categories in parallel then this example leads to approximately 4.5 GFlop/sec with a 50 MByte/sec bandwidth. Again, this is merely an example calculation and is not meant to limit the scope of claimed subject matter. For at least one embodiment, a process may be multithreaded and an application layer may reside on a multi-core CPU. An Intel Xeon Nehalem dual quad core achieves 4 flops per cycle×2.8 GHz=11.2 GFlops. Therefore, several multi-cores working together may be able to achieve desired performance in this example.

In another embodiment, frame processing may be accelerated by graphics processing unit(s) 520. For example, in at least one embodiment, recognition processes resident in an application layer may interact with a GPU via an application program interface (API) 521. GPU's are generally suited for pixel array processing and associated matrix operations. One example may use the NVidia Fermi GPU and CUDA application layer programming interface (API); although claimed subject matter is not limited in scope in this respect. For example, the CUDA API supports a selected set of function calls to make use of parallelism of a GPU. 100 GFlops has been achieved with 20 GBytes/sec bandwidth.

In at least one embodiment, one advantage of an automated reasonably high throughput system applying spectral recognition includes a technique for reasonably fast sample area capture to effectively process relatively large sample sets for rare cell detection. In at least one embodiment, signals may be processed using recognition approaches potentially accelerated by high performance processing units, as described below. Spectral recognition methods may be enhanced by providing category tags to individual pixels, which, in an embodiment, may be used by sorting or correlation operations in conjunction with subsequent spatial image recognition, as described in more detail below. In this context, a category or class refers to an identifiable spectral signature of a signal characteristic that may be associated with cells or sub-cellular level entities, e.g. an organelle, nucleus, nuclear domain, or cytoplasm. These cellular or sub-cellular entities are further associated with various types of tissue or blood, which may be normal or affected by disease.

Figure 6:
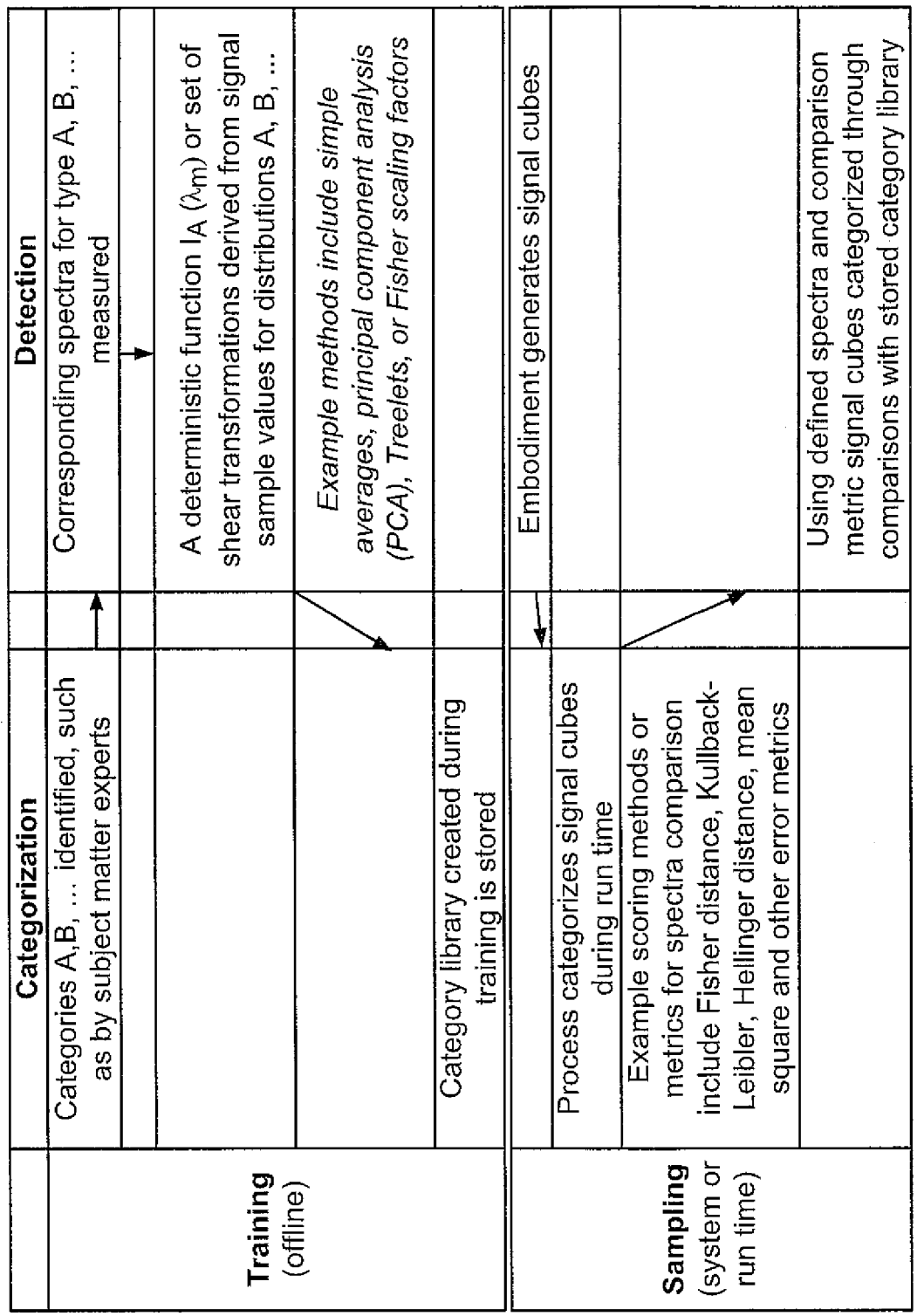
FIG. 6 is a schematic diagram showing an embodiment or implementation of a process for spectral recognition, including offline training, in accordance with claimed subject matter.

In at least one embodiment, spectral recognition may comprise detection or categorization methods. For a possible embodiment, FIG. 6 is a schematic depiction of an approach to training or sampling to support detection or categorization. Of course, this example is provided for purposes of illustration and claimed subject matter is not limited in scope to this example embodiment.

In at least one embodiment, spectral imaging may be employed to associate spectra with spatial information. In at least one embodiment, sample object-field may, for example, be illuminated with light, such as visible light, at a series of wavelengths $(\lambda_m)$. At a wavelength, in an embodiment, a digital camera CCD or CMOS sensor, for example, may generate a two dimensional array of pixels or pixel signals to produce a frame. In at least one embodiment, mage frames may be transported, processed or stored by a computing device, such as a computing platform or a host computer. A special purpose or specific computing device or computing platform may include capability to execute signal processing, such as processing as described in more detail later; however, claimed subject matter is not intended to be limited in scope in this respect.

In this context, a signal cube, such as an image or imaging signal cube, for example, may comprise a collection of frames, one per wavelength, for a given sample object field. Of course, in other embodiments, a signal cube may correspond to other logical configurations of pixels at a given wavelength, which might be affected by various signal transformations occurring within or being executed by associated hardware or software. Regardless, in this particular example implementation, a series of exposures may create a signal cube for a given image field. For example, a pixel or pixel signal may be associated with a spectral or signal characteristic $I(\lambda_N)$, which may, for at least one embodiment, be described as a vector-valued intensity, e.g. an array of scalar intensities with a scalar being an intensity value at a given wavelength. For a given wavelength, a specified scalar value per pixel, for example, may be combined, associated, represented or collected as a frame, e.g., a two dimensional pixel array, representing an image field exposed at that wavelength in at least one embodiment A signal cube may thus comprise a three dimensional object associated with an array of pixels and their intensity vectors, in at least one embodiment. In at least one embodiment, a spectral recognition method may categorize an intensity vector on a per pixel basis, although claimed subject matter is not limited in scope in this respect.

Figure 7:
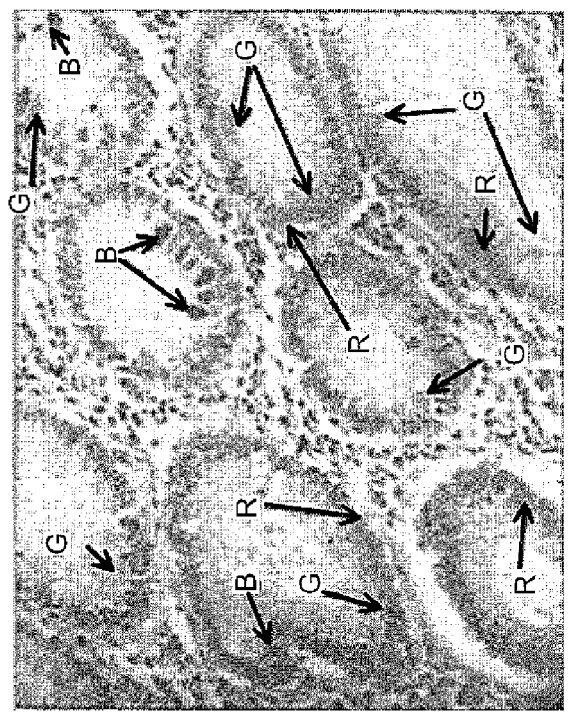
FIG. 7 is an example of a micrograph showing tissue type categories along with corresponding spectral characteristics.
Figure 7:
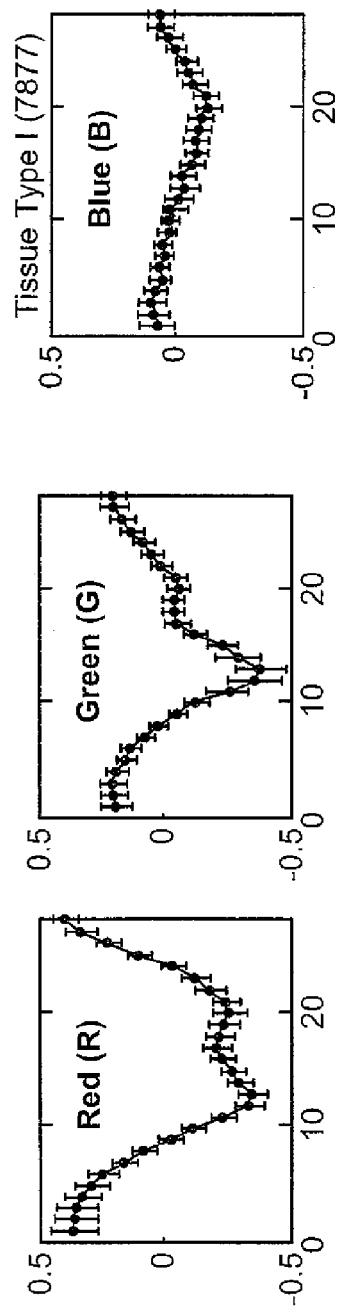

In at least one embodiment, a representative sample set of a category, such as a category A, may be identified. For example, from direct observation of a micrograph depicting cells or intracellular entities, a representative sample set may be selected or identified for a particular category of cells or intracellular entities by a subject matter expert. Likewise, multiple categories A, B . . . may be established or identified, such as within an image, for example. Any particular category may comprise selected sample sets of pixels associated with a region of interest. FIG. 7 (reference "Treelets—An adaptive multi-scale basis for sparse unordered data." A. Lee, B. Nadler, and L. Wasserman. Annals of Applied Statistics, 2008, Vol. 2, No. 2, 435-471), for example, shows an illustration of cells distinguished by spectra for three tissue categories A, B, and C. Although claimed subject matter is not limited in scope to this example.

In at least one embodiment, measurement of corresponding intensity-wavelength spectra $I_A(\lambda_m)$, for type or category A, for example, may be made at m wavelengths. A log-transmission or other normalization may be applied to intensity magnitudes in an embodiment. A top hat on an intensity, such as Ĩ, is employed here to indicate that in an embodiment a spectrum may represent or include a random distribution for a given category. By this, it is meant that a collection of pixels may be associated with a given class or category in an embodiment. A pixel, thus, may comprise a vector-valued member of a class. A set of pixel vectors may correspond to intensities having a distribution of scalar values in an embodiment. Graphically, this is shown by example in FIG. 7 as error bars at each wavelength for the three spectra associated with the three tissue type categories. For example, in one particular example or embodiment, 60,000 sample pixel signals or signal sample values may be applied for training to produce a distribution function for category A. In an implementation, a similar approach or process may be applied for various categories of interest.

In at least one embodiment, a linear discriminant function or other deterministic function $I_A(\lambda_m)$, may be derived from noisy pixel signals, or their transformed distributions. One embodiment or implementation method for the latter may involve training sample signal values comprising m-component vector of intensities $I_A[\lambda_j]$ per pixel for category A, for example. In alternative embodiments, as described in more detail below, linear transformations or other discriminant methods may be applied to category distributions. In at least one embodiment, for example, classes may be associated with cells, organelles or other sub-cellular structures, or tissue types. Raw or unprocessed pixel signal samples of spectra may be processed in a manner to be associated with a particular class or category in at least one embodiment.

Likewise, in at least one embodiment, category or class separability in a supervised learning environment may be implemented by applying linear discriminants combined with Treelet-Jacobi rotations. We demonstrate one embodiment using an example or implementation applied to three species of the Iris flower; signal samples from a paper by Fischer are employed see "The use of multiple measurements in taxonomic problems", R. A. Fisher, Annals of Eugenics, v. 7, p. 179-188 (1936). In an implementation or embodiment, for example, a sample distribution may be represented as a vector of distributions "training signal"] for a class or category, such as A, for example, by $$X_A^{(0)} = [x_1^{(0)}, \ldots, x_m^{(0)}]_A = |x^{(0)}\rangle_A = [s_1, \ldots, s_m] = \hat{l}_A$$
$$(\lambda_1), \ldots \hat{l}_A(\lambda_m)]$$

Spectral intensity signals to be processed for cells may be utilized in accordance with this relationship in at least one embodiment or implementation. Below, a signal representation as follows $$X_A^{(0)} = [x_1^{(0)}, \ldots, x_m^{(0)}]_A = |x^{(0)}\rangle_A$$

maybe employed for convenience.

A variety of approaches are available to process signals in order to distinguish associated distributions. In at least one embodiment, a library of categories or classes of signal samples may be generated using training signal samples for matching or scoring with signals or signal samples produced from platform or system operation.

For one or more embodiments, literature on robust classification of signals may be applied for generation of spectral categories from training signal samples, see e.g. chapters 14-16, "Numerical Recipes" of *The Art of Scientific Computing*, 3$^{rd}$ Edition Press, Teukolsky, Vetterling, Flannery. Likewise, a wide array of spectral mapping tools is also commercially available. See, e.g., Harris, "Spectral mapping tools from the earth sciences applied to spectral microscopy data" appearing in Cytometry, Part A, 69A:872-879 (2006).

In at least one embodiment, for example, a shear linear discriminant approach (SLD) for separating two categories or classes may be applied, although claimed subject matter is not limited in scope to applying this particular approach. For example, in an alternative embodiment, Fisher's linear discriminant (FLD) approach, a treelet approach, or an approach employing principal component analysis (PCA), may be applied.

In an embodiment employing an FLD, for example, a ratio of a difference between specific means (D) to a standard deviation $S^{1/2}$ within categories may be employed in accordance with this relationship $$D_{AB} = D/2S^{1/2}$$

where $D_{AB}$ comprises the Fisher distance between distributions A and B. By way of comparison, a related approach, referred to as Linear Discriminant Analysis (LDA), exists and may be employed in a particular embodiment, however, LDA may perform calculations using various assumptions that are not necessary to obtain desirable results in accordance with claimed subject matter.

Various other methods have also been proposed to classify high dimensional, unordered, noisy signals or signal samples that may be employed in an embodiment and are intended to be included within the scope of claimed subject matter; however, it is not necessary that all such methods be discussed in detail. However, for purposes of illustration, without intending to limit the scope of claimed subject matter, an embodiment applying a Treelet method in combination with linear discriminant scaling is provided below.

In at least one particular embodiment, a Treelet implementation or approach may improve on a PCA implementation or approach by using or applying local transforms, e.g., two-variable rotations as a possible example, instead of global transformations employing linear combinations of all axes, for example. Therefore, a treelet approach applied to a multi-dimensional set of parameters may employ transforms that treat two parameters at a time out of group or set of parameters to separate distributions in a manner that may increase distance between the two parameters treated or handled; however, this two parameter at a time approach in one possible embodiment may be applied to all combinations of two parameters at a time for parameters out of the group. Instead, by contrast, a PCA approach may treat all parameters of the group at once to increase separation between all parameters of the group. Therefore, for an embodiment, a treelet approach may result in improved separation over a PCA approach, although may have increased computation complexity to implement. For an embodiment, a treelet method also appears to have some computational benefit in stopping short of complete diagonalization as done by a Jacobi transformation of a symmetric matrix. That is, a treelet approach may recognize that diminishing returns of some form may set in and once sufficient separation maybe realized may omit completion of processing additional pairs of parameters in order to conserve computational resources.

For convenience and purposes of illustration, below a shear, shear-type or shear-like transformation approach as may be employed in an embodiment shall be demonstrated through application to signal information provided by Fisher's paper. In this manner, for at least one embodiment, improvement available through application of a shear, shear-like or shear-type transformation over an approach employing an FLD approach will be readily apparent. Interestingly, we find that complete diagonalization of applicable covariance matrices does necessarily not lead to further improvement of results beyond that of a Treelet method. However, likewise, we also find that Treelet rotations alone in some situations may not be sufficient to generate sufficient separation of distributions representing different classes or categories. Therefore, for at least one embodiment, a shear, shear-like or shear-type transformation approach may to provide unexpected improvement over either approach in terms of increasing separation between distributions in a manner that is quantifiable and, likewise, as a result demonstrable, as shown below. It is noted here that terminology or wording, such as "type" or "like" used, for example, as follows: "shear-type," "rotation-type," "scale-type," "shear-like," "rotation-like," or "scale-like" in conjunction with terminology or wording, such as "transformation," for example, is intended to be at least partially limiting by referring to a transformation sufficiently like or sufficiently similar in type to a more conventionally referenced transformation so that minor variations or differences from the more conventionally referenced transformation for the particular transformation permit the particular transformation to be associated with or treated as a species of the more conventionally referenced transformation. Likewise, it shall be understood that throughout this document, if a more conventional transformation, such as, to provide a specific example, a shear, a rotation or a scaling transformation, for example, is referenced, it should be understood that the reference is also intended to include other related transformations, such as, corresponding to the specific example, shear-like or shear-type transformations, rotation-like or rotation-type transformations or scaling-like or scaling-type transformations, respectively.

An embodiment employing a shear transformation may therefore provide a beneficial approach to separating distributions or increasing distance between two classes or categories and provide unexpected benefits or improvements over existing state-of-the art approaches, as discussed in more detail below. For an embodiment, in the context of an overall system or platform to process samples, application of a shear or shear-like transformation, for example, may offer an opportunity to achieve or realize a probability of misclassification on the order of one part per billion or better, as is desired to meet goals of sufficient sample processing within acceptable time frames to be useful in actual practice, as suggested earlier. Of course, other approaches may also realize a probability of misclassification of one part per billion or better and it is intended that claimed subject matter include those approaches as well. For example, as mentioned previously and described below, it may be possible to apply approaches including FLD, treeless or PCA.

As illustrated in more detail below, combinations of scaling and rotation are not commutative operations in general. Therefore, in at least one embodiment, an approach to increase separation may involve varying order of applying operations or transformations to obtain improved separation of distributions for at least some situations. Thus, algebraic manipulation including affine transformations may provide an area in which for other embodiments in accordance with claimed subject matter greater improvements in precision, accuracy, sensitivity, or selectivity may be possible. Likewise, the foregoing approaches focus primarily on linear signal processing; however, non-linear approaches also may be employed in some embodiments to provide opportunities for additional improvement in precision, if desired. For example, and without limitation, one potential example of a possible embodiment may include application of genetic processes to seek improvement in discriminants through non-linear processing or transformations. However, regardless, as mentioned, in at least one embodiment, a feasible approach of creating category training distributions, which may realize one part per billion precision is discussed. It is intended that claimed subject matter include all modifications or variations thereof, including those modifications or variations mentioned above.

Fischer describes 4 characteristics. Therefore, in this example implementation, m=4 characters, which are measurement variables for three classes or categories of the Iris flower: $A_0$ (setosa), $A_1$ (versicolor), $A_2$ (virginica). Fischer's example employs 50 samples per category (raw measurement signal sample information is provided for ease of comparison in Table I).

TABLE I

| Iris setosa (raw data) | | | | Iris versicolor (raw data) | | | | Iris virginica | | | |
|---|---|---|---|---|---|---|---|---|---|---|---|
| Sepal length | Sepal width | Petal length | Petal width | Sepal length | Sepal width | Petal length | Petal width | Sepal length | Sepal width | Petal length | Petal width |
| 5.1 | 3.5 | 1.4 | 0.2 | 7 | 3.2 | 4.7 | 1.4 | 6.3 | 3.3 | 6 | 2.5 |
| 4.9 | 3 | 1.4 | 0.2 | 6.4 | 3.2 | 4.5 | 1.5 | 5.8 | 2.7 | 5.1 | 1.9 |
| 4.7 | 3.2 | 1.3 | 0.2 | 6.9 | 3.1 | 4.9 | 1.5 | 7.1 | 3 | 5.9 | 2.1 |
| 4.6 | 3.1 | 1.5 | 0.2 | 5.5 | 2.3 | 4 | 1.3 | 6.3 | 2.9 | 5.6 | 1.8 |
| 5.0 | 3.6 | 1.4 | 0.2 | 6.5 | 2.8 | 4.6 | 1.5 | 6.5 | 3 | 5.8 | 2.2 |
| 5.4 | 3.9 | 1.7 | 0.4 | 5.7 | 2.8 | 4.5 | 1.3 | 7.6 | 3 | 6.6 | 2.1 |
| 4.6 | 3.4 | 1.4 | 0.3 | 6.3 | 3.3 | 4.7 | 1.6 | 4.9 | 2.5 | 4.5 | 1.7 |
| 5.0 | 3.4 | 1.5 | 0.2 | 4.9 | 2.4 | 3.3 | 1 | 7.3 | 2.9 | 6.3 | 1.8 |
| 4.4 | 2.9 | 1.4 | 0.2 | 6.6 | 2.9 | 4.6 | 1.3 | 6.7 | 2.5 | 5.8 | 1.8 |
| 4.9 | 3.1 | 1.5 | 0.1 | 5.2 | 2.7 | 3.9 | 1.4 | 7.2 | 3.6 | 6.1 | 2.5 |
| 5.4 | 3.7 | 1.5 | 0.2 | 5 | 2 | 3.5 | 1 | 6.5 | 3.2 | 5.1 | 2 |
| 4.8 | 3.4 | 1.6 | 0.2 | 5.9 | 3 | 4.2 | 1.5 | 6.4 | 2.7 | 5.3 | 1.9 |
| 4.8 | 3 | 1.4 | 0.1 | 6 | 2.2 | 4 | 1 | 6.8 | 3 | 5.5 | 2.1 |
| 4.3 | 3 | 1.1 | 0.1 | 6.1 | 2.9 | 4.7 | 1.4 | 5.7 | 2.5 | 5 | 2 |
| 5.8 | 4 | 1.2 | 0.2 | 5.6 | 2.9 | 3.6 | 1.3 | 5.8 | 2.8 | 5.1 | 2.4 |
| 5.7 | 4.4 | 1.5 | 0.4 | 6.7 | 3.1 | 4.4 | 1.4 | 6.4 | 3.2 | 5.3 | 2.3 |
| 5.4 | 3.9 | 1.3 | 0.4 | 5.6 | 3 | 4.5 | 1.5 | 6.5 | 3 | 5.5 | 1.8 |
| 5.1 | 3.5 | 1.4 | 0.3 | 5.8 | 2.7 | 4.1 | 1 | 7.7 | 3.8 | 6.7 | 2.2 |
| 5.7 | 3.8 | 1.7 | 0.3 | 6.2 | 2.2 | 4.5 | 1.5 | 7.7 | 2.6 | 6.9 | 2.3 |
| 5.1 | 3.8 | 1.5 | 0.3 | 5.6 | 2.5 | 3.9 | 1.1 | 6 | 2.2 | 5 | 1.5 |
| 5.4 | 3.4 | 1.7 | 0.2 | 5.9 | 3.2 | 4.8 | 1.8 | 6.9 | 3.2 | 5.7 | 2.3 |
| 5.1 | 3.7 | 1.5 | 0.4 | 6.1 | 2.8 | 4 | 1.3 | 5.6 | 2.8 | 4.9 | 2 |
| 4.6 | 3.6 | 1 | 0.2 | 6.3 | 2.5 | 4.9 | 1.5 | 7.7 | 2.8 | 6.7 | 2 |
| 5.1 | 3.3 | 1.7 | 0.5 | 6.1 | 2.8 | 4.7 | 1.2 | 6.3 | 2.7 | 4.9 | 1.8 |
| 4.8 | 3.4 | 1.9 | 0.2 | 6.4 | 2.9 | 4.3 | 1.3 | 6.7 | 3.3 | 5.7 | 2.1 |
| 5.0 | 3 | 1.6 | 0.2 | 6.6 | 3 | 4.4 | 1.4 | 7.2 | 3.2 | 6 | 1.8 |
| 5.0 | 3.4 | 1.6 | 0.4 | 6.8 | 2.8 | 4.8 | 1.4 | 6.2 | 2.8 | 4.8 | 1.8 |
| 5.2 | 3.5 | 1.5 | 0.2 | 6.7 | 3 | 5 | 1.7 | 6.1 | 3 | 4.9 | 1.8 |
| 5.2 | 3.4 | 1.4 | 0.2 | 6 | 2.9 | 4.5 | 1.5 | 6.4 | 2.8 | 5.6 | 2.1 |
| 4.7 | 3.2 | 1.6 | 0.2 | 5.7 | 2.6 | 3.5 | 1 | 7.2 | 3 | 5.8 | 1.6 |
| 4.8 | 3.1 | 1.6 | 0.2 | 5.5 | 2.4 | 3.8 | 1.1 | 7.4 | 2.8 | 6.1 | 1.9 |
| 5.4 | 3.4 | 1.5 | 0.4 | 5.5 | 2.4 | 3.7 | 1 | 7.9 | 3.8 | 6.4 | 2 |
| 5.2 | 4.1 | 1.5 | 0.1 | 5.8 | 2.7 | 3.9 | 1.2 | 6.4 | 2.8 | 5.6 | 2.2 |
| 5.5 | 4.2 | 1.4 | 0.2 | 6 | 2.7 | 5.1 | 1.6 | 6.3 | 2.8 | 5.1 | 1.5 |
| 4.9 | 3.1 | 1.5 | 0.2 | 5.4 | 3 | 4.5 | 1.5 | 6.1 | 2.6 | 5.6 | 1.4 |
| 5.0 | 3.2 | 1.2 | 0.2 | 6 | 3.4 | 4.5 | 1.6 | 7.7 | 3 | 6.1 | 2.3 |
| 5.5 | 3.5 | 1.3 | 0.2 | 6.7 | 3.1 | 4.7 | 1.5 | 6.3 | 3.4 | 5.6 | 2.4 |
| 4.9 | 3.6 | 1.4 | 0.1 | 6.3 | 2.3 | 4.4 | 1.3 | 6.4 | 3.1 | 5.5 | 1.8 |
| 4.4 | 3 | 1.3 | 0.2 | 5.6 | 3 | 4.1 | 1.3 | 6 | 3 | 4.8 | 1.8 |
| 5.1 | 3.4 | 1.5 | 0.2 | 5.5 | 2.5 | 4 | 1.3 | 6.9 | 3.1 | 5.4 | 2.1 |
| 5.0 | 3.5 | 1.3 | 0.3 | 5.5 | 2.6 | 4.4 | 1.2 | 6.7 | 3.1 | 5.6 | 2.4 |
| 4.5 | 2.3 | 1.3 | 0.3 | 6.1 | 3 | 4.6 | 1.4 | 6.9 | 3.1 | 5.1 | 2.3 |
| 4.4 | 3.2 | 1.3 | 0.2 | 5.8 | 2.6 | 4 | 1.2 | 5.8 | 2.7 | 5.1 | 1.9 |
| 5.0 | 3.5 | 1.6 | 0.6 | 5 | 2.3 | 3.3 | 1 | 6.8 | 3.2 | 5.9 | 2.3 |
| 5.1 | 3.8 | 1.9 | 0.4 | 5.6 | 2.7 | 4.2 | 1.3 | 6.7 | 3.3 | 5.7 | 2.5 |
| 4.8 | 3 | 1.4 | 0.3 | 5.7 | 3 | 4.2 | 1.2 | 6.7 | 3 | 5.2 | 2.3 |
| 5.1 | 3.8 | 1.6 | 0.2 | 5.7 | 2.9 | 4.2 | 1.3 | 6.3 | 2.5 | 5 | 1.9 |

TABLE I-continued

| Iris setosa (raw data) | | | | Iris versicolor (raw data) | | | | Iris virginica | | | |
|---|---|---|---|---|---|---|---|---|---|---|---|
| Sepal length | Sepal width | Petal length | Petal width | Sepal length | Sepal width | Petal length | Petal width | Sepal length | Sepal width | Petal length | Petal width |
| 4.6 | 3.2 | 1.4 | 0.2 | 6.2 | 2.9 | 4.3 | 1.3 | 6.5 | 3 | 5.2 | 2 |
| 5.3 | 3.7 | 1.5 | 0.2 | 5.1 | 2.5 | 3 | 1.1 | 6.2 | 3.4 | 5.4 | 2.3 |
| 5.0 | 3.3 | 1.4 | 0.2 | 5.7 | 2.8 | 4.1 | 1.3 | 5.9 | 3 | 5.1 | 1.8 |

Notation employed below allows a connection between a specific example as outlined, and a more general approach, that may likewise be applied to or employed with other cases or embodiments, e.g. use for rare cell identification by spectral recognition. For an embodiment, a sample distribution may be represented as a vector of distributions (e.g., "training signal") for class or category A by $$X_A^{(0)} = [x_1^{(0)}, \ldots, x_m^{(0)}]_A = |x^{(0)}\rangle_A = [s_1, \ldots, s_m] = [\hat{I}_A(\lambda_1), \ldots \hat{I}_A(\lambda_m)].$$

A component $$x_j^{(0)}$$

signal or signal sample may comprise a random variable (character) from a signal sample set used to characterize a training category A signal distribution in at least one embodiment. A (0) superscript may be employed to indicate raw or unprocessed signal samples for an embodiment. Nonzero superscripts may be employed to represent signal sample transformations for an embodiment. A symmetric m×m correlation matrix may be represented as follows:

$$\mathbb{R} = |x^{(a)}\rangle_{A'A} \langle x^{(a)}| = [R_{jk}] = [\langle x_j \cdot x_k \rangle]$$

where $R_{kj} = R_{jk}$ and $1 \leq j, k \leq m$.

A linear function, such as a scaling operation, in an embodiment may be employed to discriminate populations among a signal sample set for category A:

$$X_A = \Sigma \lambda_j x_j = \vec{\lambda} \cdot \vec{x}$$

A scaling function or operation, such as above, for example, may be employed to score a signal sample comprising, in this particular example, four possible or discernible measurements $$x_j (j=1,4).$$

A scaled vector may, for example, in an embodiment reference a reciprocal space with units of inverse length $$\vec{\lambda} \, [\text{length}^{-1}].$$

Applying this approach for this particular example, a difference between two scaled means of X in two classes or categories A and B may be determined as follows:

$$D_{AB} = \Sigma \lambda_j \langle d_j \rangle_{AB} = \vec{\lambda} \cdot \langle \vec{d} \rangle_{AB}$$

where $\langle d_j \rangle_{AB} = \langle x_j \rangle_A - \langle x_j \rangle_B$, e.g., a difference in means of two classes A and B, shown, for example, in Table II.

TABLE II

| Iris setosa (raw data) | | | | Iris versicolor (raw data) | | | | Iris virginica | | | |
|---|---|---|---|---|---|---|---|---|---|---|---|
| Mean values | | | | | | | | | | | |
| $\langle x1 \rangle$ | $\langle x2 \rangle$ | $\langle x3 \rangle$ | $\langle x4 \rangle$ | $\langle x1 \rangle$ | $\langle x2 \rangle$ | $\langle x3 \rangle$ | $\langle x4 \rangle$ | x1 | x2 | x3 | x4 |
| 5.01 | 3.43 | 1.46 | 0.25 | 5.94 | 2.77 | 4.26 | 1.33 | 6.588 | 2.974 | 5.552 | 2.026 |

| | |
|---|---|
| d1 | 0.930 |
| d2 | −0.658 |
| d3 | 2.798 |
| d4 | 1.080 |

A covariance matrix may be represented or described as follows:

$$C = [S_{jk}] = |\delta x\rangle \langle \delta x| = [\langle \delta x_j \cdot \delta x_k \rangle] = \left\langle \begin{bmatrix} \delta x_1 \\ \cdots \\ \delta x_m \end{bmatrix} * [\delta x_1 \ldots \delta x_m] \right\rangle.$$

In at least one embodiment, a correlation coefficient, such as follows, for example:

$$\gamma_{jk} = S_{jk} / (s_{jj} \cdot s_{kk})^{0.5}$$

may be employed to measure similarity of pairs of variables. Likewise, a variance of X "within species" may be employed in an embodiment as follows, for example:

$$S_{AB} = \Sigma_{p,q=1}^{4} \lambda_p \lambda_q S_{pq}$$

where $S_{pq} = \langle \delta x_p \delta x_q \rangle_{A+B}$ and an A+B average may indicate that "the within species" covariance may be, in this particular example, averaged over a 100 signal sample set comprising two populations or classes A and B. Of course, this is merely an illustrative example and claimed subject matter is not limited in scope in this respect.

Table III shows signal sample values for $S_{pq}$.

TABLE III

| | Covariance "within species" | | | |
|---|---|---|---|---|
| $S_{pq}$ | x1 | x2 | x3 | x4 |
| x1 | 19.1434 | 9.0356 | 9.7634 | 3.2394 |
| x2 | 9.0356 | 11.8658 | 4.6232 | 2.4746 |
| x3 | 9.7634 | 4.6232 | 12.2978 | 3.8794 |
| x4 | 3.2394 | 2.4746 | 3.8794 | 2.4604 |

One possible approach in one possible embodiment, without limitation, to discriminate between two species A and B may involve calculating a ratio as follows $$(D_{AB})^2/S$$

and taking its derivative with respect to $$\lambda_j$$

Applying the derivative produces the following:

$$\frac{1}{2}\frac{\partial S}{\partial \lambda} = \frac{S}{D}\frac{\partial D}{\partial \lambda}$$

The above relationship above may be written as follows:

$$\frac{\partial \ln S}{\partial \lambda} = \frac{\partial \ln D^2}{\partial \lambda}.$$

The relationship immediately above comprises a non-linear relation. Therefore, for a variety of embodiments, a number of approaches may exist to produce values that satisfy the relationship. It is noted that claimed subject matter is not intended to be limited to solving this relationship or to applying any particular approach to solving this relationship; however, approaches to obtaining values that satisfy this relationship are intended to be included within the scope of claimed subject matter. For example, genetic processes may be applied to provide insight to possible solutions.

However, for this particular illustrative example, without intending to limit the scope of claimed subject matter, Fisher's linear discriminant method may be employed. Fisher, for example, was able to simplify the non-linear relation above by employing the following additional relation:

$$\frac{S}{D} = \text{constant}$$

which may permit a linear discriminant solution having the following form:

$$[S_{pq}]\cdot \vec{\lambda} = \vec{d}$$

where $\vec{\lambda}=[\lambda_1;\lambda_2;\lambda_3;\lambda_4]$. An matrix inverse $$[S_{pq}]^{-1}$$

for this particular example component signal values may be computed as given in Table IV below.

TABLE IV

| Matrix inverse of Table III Fishers paper $S_{pq}$ | | | |
|---|---|---|---|
| 0.11872 | −0.06687 | −0.08162 | 0.03964 |
| −0.06687 | 0.14527 | 0.03341 | −0.11075 |
| −0.08162 | 0.03341 | 0.21936 | −0.27202 |
| 0.03964 | −0.11075 | −0.27202 | 0.89455 |

The relation immediately above may be rewritten as:

$$\vec{\lambda} = [S_{qp}]^{-1}\vec{d}.$$

Signal values for $$\lambda_j$$

may be obtained by multiplying columns of $$[S_{pj}]^{-1}$$

by observed differences $$\vec{d} = [d_1;d_2;d_3;d_4]$$

yielding:

| Fisher's scaled results | |
|---|---|
| $\lambda_1$ | −0.031 |
| $\lambda_2$ | −0.184 |
| $\lambda_3$ | 0.222 |
| $\lambda_4$ | 0.315 |

For convenience, in this particular example, signal values may be scaled. An asterisk is employed to indicate relative scaling of signal values.

| $\lambda_1^{-1}$ −32.102 | |
|---|---|
| $\lambda 1^*$ | 1.000 |
| $\lambda 2^*$ | 5.904 |
| $\lambda 3^*$ | −7.130 |
| $\lambda 4^*$ | −10.104 |

A mean value for Setosa may be derived from the above signal values and those of Table II as follows:

$$\langle X\rangle_S = \Sigma \lambda_j^* \langle x_j\rangle_S = 12.335 \text{ cm}.$$

Similarly, a mean value for Versicolor likewise may be computed as follows:

$$\langle X\rangle_V = \Sigma \lambda_j^* \langle x_j\rangle_V = -21.482 \text{ cm}.$$

A difference in mean values for this example therefore may be computed as:

$$D_{SV} = \Sigma \lambda_j \langle d_j\rangle = \langle X\rangle_S - \langle X\rangle_V = 33.82 \text{ cm}.$$

TABLE V

| $\lambda_q^* \lambda_p^* S_{pq}$ | | | Fisher's result | |
|---|---|---|---|
| 19.143 | 53.344 | −69.613 | −32.730 |
| 53.344 | 413.581 | −194.609 | −147.610 |
| −69.613 | −194.609 | 625.179 | 279.468 |
| −32.730 | −147.610 | 279.468 | 251.168 |

Table V above provides a scaled covariance matrix which may be computed from Table III and the values for $$\lambda_j^*.$$

A variance of X within species may be computed as follows for this example:

$$S = \Sigma_{p,q=1}^{4} \lambda_p^* \lambda_q^* S_{pq} = 1085.6 \text{ cm}^2.$$

To determine variance per plant, in this example, we may divide by degrees of freedom, which may be provided as sample size minus two means (for Setosa and Versicolor, respectively) minus three for three second order statistics, which may provide the result:

$$100-2-3=95.$$

Average variance of two species with respect to a compound measurement in this particular example may be computed as:

$$1085.6/95=11.42=S_{SV}.$$

Average standard deviation "within species" may therefore be computed as:

$$S_{SV}^{1/2}=3.4.$$

A Fisher distance or metric between distributions Setosa and Versicolor in this example may be computed:

$$F_{SV} \equiv \frac{1}{2} D_{SV} / S_{SV}^{1/2} = 5.0.$$

One may interpret these results in terms of probability of misclassification. Assuming, for example, without loss of generality, that a training distribution comprises a Normal distribution with mean $$m = \frac{1}{2} D_{SV}$$

and variance $$\sigma^2 = S_{SV},$$

probability of misclassification for this example may be computed as:

$$Prob\{\hat{X} \geq x\} = 1 - P\left(\frac{x-m}{\sigma}\right) = 1 - \frac{1}{\sqrt{2\pi}} \int_{-\infty}^{(x-m)/\sigma} e^{-t^2/2} dt.$$

Again, assuming a Normal distribution above, a training frequency of misclassification for two species of Iris in this example may then be $1-P(5.0)=1-0.9999997133=2.867E-07$, which is about 0.29 per million. A risk of misclassification therefore appears to be reduced to 1 part per billion if a Fisher distance of F=6 is present, again, employing similar assumptions as previously.

In any particular embodiment, estimates of misclassification precision, of course, relate at least in part to the underlying distribution. From an operational perspective, in an embodiment, if there are errors in detected samples, these may be captured, reclassified and a score may be recalculated, this being one approach to improve class separability or reduce probability of misclassification. This may also tend to improve sensitivity, selectivity, accuracy or precision.

A comparison of individual variances of Setosa and Versicolor to their specific averages may be made for this particular example using corresponding covariances calculated from unprocessed signals or signal samples, such as shown in Table VI below.

TABLE VI

| (*Satosa* only) | | Covariance matrix | | | (*Versicolor* only) | | Covariance matrix | | |
|---|---|---|---|---|---|---|---|---|---|
| $S_{pq}$ | x1 | x2 | x3 | x4 | $S_{pq}$ | x1 | x2 | x3 | x4 |
| x1 | 6.0882 | 4.8616 | 0.8014 | 0.5062 | x1 | 13.055 | 4.174 | 8.962 | 2.733 |
| x2 | 4.8616 | 7.0408 | 0.5732 | 0.4556 | x2 | 4.174 | 4.825 | 4.050 | 2.019 |
| x3 | 0.8014 | 0.5732 | 1.4778 | 0.2974 | x3 | 8.962 | 4.050 | 10.820 | 3.582 |
| x4 | 0.5062 | 0.4556 | 0.2974 | 0.5442 | x4 | 2.733 | 2.019 | 3.582 | 1.916 |

Using the previously calculated $\lambda_j^*$ yields Table VII below.

TABLE VII

| 358.16 | $\lambda_q^* \lambda_p^* S_{pq}$ | 7.31 | 2.70 | *Satosa* only | 727.41 | $\lambda_q^* \lambda_p^* S_{pq}$ | 14.85 | 3.85 | *Versicolor* only |
|---|---|---|---|---|---|---|---|---|---|
| 23.96 | 6.09 | 28.70 | −5.71 | −5.11 | −53.82 | 13.06 | 24.64 | −63.90 | −27.62 |
| 222.80 | 28.70 | 245.41 | −24.13 | −27.18 | −98.10 | 24.64 | 168.17 | −170.48 | −120.43 |
| 66.71 | −5.71 | −24.13 | 75.13 | 21.42 | 573.72 | −63.90 | −170.48 | 550.05 | 258.04 |
| 44.69 | −5.11 | −27.18 | 21.42 | 55.55 | 305.61 | −27.62 | −120.43 | 258.04 | 195.61 |

Individual variances, for this example, may be calculated from scaled covariance matrices of Table VII by summing matrix elements and dividing by degrees of freedom to obtain per sample variances. Degrees of freedom are 50 samples −1 mean or 49 in this particular instance. Results expressed as standard deviations may be computed respectively:

$$\sigma_S = 2.70 \text{ cm}$$

$$\sigma_V = 3.85 \text{ cm}$$

Figure 8:
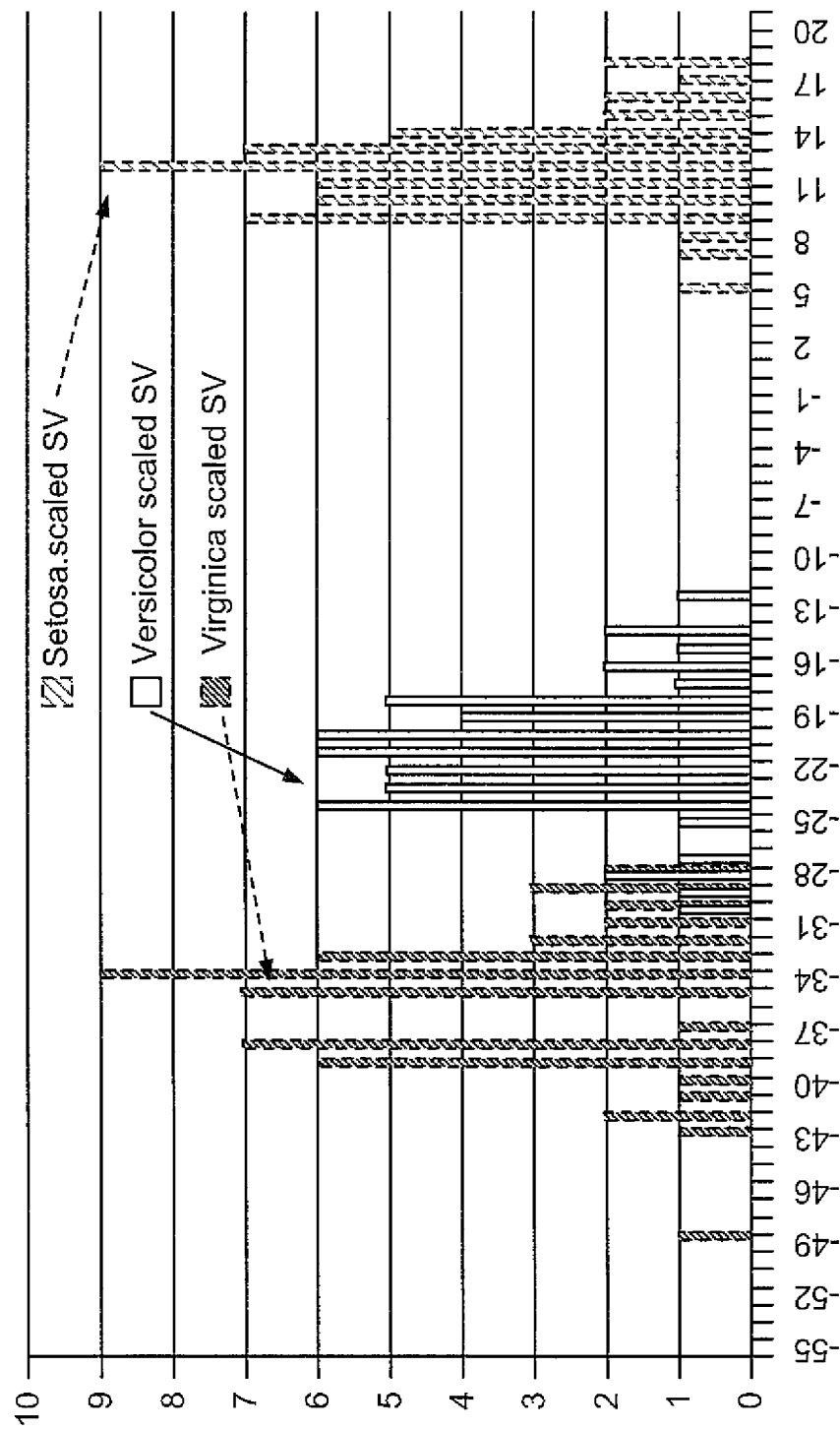
FIG. 8 is a plot illustrating a scaled transformation of discriminating sample distributions for three species.

The average appears to be near the above in-species calculation of $S_{SV}^{1/2}=3.4$. FIG. 8 is a plot illustrating scaled versions of discriminating sample distributions for three iris species using signal sample values or measurements provided previously in Table I.

For an embodiment, a Fisher distance-metric may be applied to transformations for separating classes or categories of distributions. This approach, in effect, may impose a linear scale within a multi-dimensional space, such as, for example, as part of a general linear shear transformation comprising a 4-dimensional scale transformation combined with rotations within that space, as to be described shortly in detail. For at least one embodiment, employing a general linear shear-type transformation comprising, for example, a combination of a Jacobi-Treelet-type rotation transformation and a scale-type transformation may be utilized to, in an unexpected manner, increase separation between differing distributions for differing classes or categories so that a separation results greater than may result from a sum of separations resulting from applying either transformation individually. It is, again, noted here that terminology or wording, such as "type" or "like" used, for example, as follows: "shear-type," "rotation-type," "scale-type," "shear-like," "rotation-like," or "scale-like", in conjunction with terminology or wording, such as "transformation," for example, is intended to refer to a transformation sufficiently like or sufficiently similar in type to a more conventionally referenced transformation so that minor variations or differences from the more conventionally referenced transformation are intended to be included as part of the transformation.

Additionally, these individual transformations are not commutative; therefore, in at least one embodiment, it may be prudent to apply transformations in different orders and assess separation performance with respect to the particular distributions. Of course, as previously indicated, claimed subject matter is not limited in scope to applying a shear-type transformation to signal samples. As discussed, a scale-type transformation or a rotation-type transformation may be applied and provide satisfactory results depending on a host of factors, including, for example, the particular distribution of signal samples in the particular instance. Furthermore, claimed subject matter is not limited to applying transformations at all, or to applying any particular transformation or any particular combination of transformations, linear or otherwise.

Nonetheless, at times, for an embodiment, it may be desirable to have a mechanism to increase separation of two distributions through application of linear or linear-type transformations. Coordinate rotations may offer one approach to reduce correlations, for example, and thereby increase separation of distributions. Principal component analysis (PCA) has been the traditional method for correlation reduction by transforming linear combinations of parameters or variables. Additionally, improvements on PCA may be obtained by transforming parameters or variables in pairs using rotations or rotation-type transformations.

A Jacobi method comprises a sequence of orthogonal similarity transformations, which, in effect, may be viewed as progressively diagonalizing a covariance matrix $$\mathbb{C}^{(1)} = \mathbb{J}^T_{pq} \mathbb{C}^{(0)} \mathbb{J}_{pq} = \mathbb{J}^T_{pq} \cdot |\delta x^{(0)}\rangle_A \cdot \langle \delta x^{(0)}| \cdot \mathbb{J}_{pq} = \|\delta x^{(1)}\rangle_{A \cdot A} \langle \delta x^{(1)}\|$$

In an embodiment, pairwise, $x_p, x_q$ variable transformations via Jacobi rotations may be employed to reduce or even eliminate corresponding off-diagonal covariance matrix elements, such as $$C_{pq} = \langle \delta x_p \cdot \delta x_q \rangle.$$

A Jacobi rotation matrix may be provided as:

$$\mathbb{J}_{pq} = \begin{bmatrix} 1 & & & & & & \\ & 1 & & 0 & & 0 & \\ & & \begin{bmatrix} c & \cdots & s \\ \vdots & 1 & \vdots \\ -s & \cdots & c \end{bmatrix} & & & & \\ & 0 & & & & 0 & \\ & & & & & 1 & \\ & 0 & & 0 & & & 1 \end{bmatrix}$$

with $c = \cos \phi_{pq}$ and $s = \sin \phi_{pq}$ appearing in the $p^{th}$ and $q^{th}$ rows and columns and whose argument, which may be computed as $$\phi_{pq} + k\pi = \frac{1}{2} \tan^{-1} \frac{2 C_{pq}}{(C_{qq} - C_{pp})}$$

may be derived from covariance matrix elements. One convention may set k=0, which may result in $-\pi/4 \leq \phi_{pq} \leq \pi/4$ for an embodiment. Components of a covariance matrix, from the relation above, for an embodiment, may include the following:

$$C^{(1)}_{rp} = c \cdot C^{(0)}_{rp} - s \cdot C^{(0)}_{rq}$$

$$C^{(1)}_{rq} = c \cdot C^{(0)}_{rq} + s \cdot C^{(0)}_{rp}$$

These hold for $r \neq p$, $r \neq q$, otherwise:

$$C^{(1)}_{pp} = c^2 \cdot C^{(0)}_{pp} + s^2 \cdot C^{(0)}_{qq} - 2 \cdot s \cdot c \cdot C^{(0)}_{pq}$$

$$C^{(1)}_{qq} = s^2 \cdot C^{(0)}_{pp} + c^2 \cdot C^{(0)}_{qq} + 2 \cdot s \cdot c \cdot C^{(0)}_{pq}$$

$$C^{(1)}_{qq} = (c^2 - s^2) C^{(0)}_{pq} + sc(C^{(0)}_{pp} - C^{(0)}_{qq})$$

Other matrix elements may remain unchanged for an embodiment.

For an embodiment, a rotation transformation or rotation-type transformation may comprise a rotation in an $x_p, x_q$ plane and a change of basis in accordance with the following:

$$\langle \delta x^{(0)}| \cdot \mathbb{J}_{pp} = [\delta x; \ldots; \delta x_{p-1}; (c \cdot \delta x_p - s \cdot \delta x_q); \delta x_{p+1}; \ldots \delta x_{q-1}; (s \cdot \delta x_p + c \cdot \delta x_q); \delta x_{q+1}; \ldots \delta x_0] = \langle \delta x^{(0)}| \mathbb{J}_0.$$

$$\mathbb{B}_{pq} = \langle \delta x^{(0)}| \mathbb{B}_1 = \langle \delta x^{(1)}\|$$

where $\mathbb{B}_0$ comprises the identity matrix and where $\mathbb{B}_{l-1} \cdot \mathbb{J}_{k(l)j(l)} = \mathbb{B}_l$ results in a change of basis with new coordinates $\langle \delta x^{(1)}|$. For an embodiment, a subsequent iteration may therefore produce a new basis vector as follows:

$$C^{(l)} = \mathbb{J}^T C^{(l-1)} \mathbb{J} = \mathbb{J}^T \cdot |\delta x^{(l-1)}\rangle_A \cdot \langle \delta x^{(l-1)}| \cdot \mathbb{J}.$$

This result, for an embodiment, may be viewed as similar to diagonalization of a covariance matrix, but with a new pair of axes k(l), j(l) determined from the largest correlation coefficient among covariance matrix elements for example.

The previously cited article by Lee applies rotations to pairs of variables in a manner as discussed or suggested previously. This may be viewed, for an embodiment, as a localized Treelet approach using similarity or rotation transformations operating on a covariance matrix, much like a Jacobi rotation method, described above. A Treelet approach is named for a hierarchical method of axes transformation by applying successive operations to reduce cross correlations among signal samples. In at least one embodiment, order of transformation of variables may be applied in accordance with particular values of respective correlation coefficients. In at least one embodiment, variables or parameters more highly correlated may be rotated earlier than ones less highly correlated. For example, for an embodiment, a large off diagonal covariance element $C_{ij}$ may be selected, which may be related mathematically to a distance value $$d_{ij} = (1 - \eta_{ij})/2.$$

We note here that, as employed in an embodiment, a Treelet process is generally or typically designed to terminate after p−1 rotations, where p represents dimensionality of measurements. For example, as an illustration, for the Fisher iris example, provided previously, p is 4. In contrast, for a Jacobi method, rotations continue until off diagonal elements of a covariance matrix are effectively zeroed or nearly so. Viewed in this matter, for an embodiment, a Treelet method may be considered more practical by setting a limit or point beyond which further improvement in essence may not necessarily occur with respect to reducing a Fisher distance through application of subsequent or additional similarity transformations.

At times, for an embodiment, it may be that a Treelet rotation or rotation-type transformation may not be sufficient alone to achieve a desired amount of class or category separability. As an example, a Treelet transformation may be applied to signal samples provided in Table I and compared with prior results in which a scaling transformation had been applied.

Table VIII below provides correlation coefficients for Satosa and Versicolor in this example. Similar to selection in a Treelet approach above, two coordinates to be rotated may be determined in accordance with particular correlation coefficient values. Relatively high values may indicate similarity. For this example, values are highlighted in the following table.

TABLE VIII

| corr.coeff(*Satosa* only) | raw data | max rij selects 1st rotation | | corr.coeff(*Versicolor* only) | | max rij selects 1st rotation | |
|---|---|---|---|---|---|---|---|
| $r_{pq}^{(0)}$ | x1 | x2 | x3 | x4 | $r_{pq}^{(0)}$ | x1 | x2 | x3 | x4 |
| x1 | 1.000 | 0.743 | 0.267 | 0.278 | x1 | 1.000 | 0.526 | 0.754 | 0.546 |
| x2 | 0.743 | 1.000 | 0.178 | 0.233 | x2 | 0.526 | 1.000 | 0.561 | 0.664 |
| x3 | 0.267 | 0.178 | 1.000 | 0.332 | x3 | 0.754 | 0.561 | 1.000 | 0.787 |
| x4 | 0.278 | 0.233 | 0.332 | 1.000 | x4 | 0.546 | 0.664 | 0.787 | 1.000 |

These values may also be associated with the covariance matrices of Table VII. Using the previously provided relation above, for this particular example, the following two rotation angles are found using the identified correlation coefficients:

| 0.737 | Rot angle [rad] | 42.20 | Rot ang [deg] | $\phi_{12}$ *Setosa* | −0.339 | Rot angle [rad] | −19.4 | Rot ang [deg] | $\phi_{34}$ *Versicolor* |
|---|---|---|---|---|---|---|---|---|---|

The result for this example of a first rotation may be computed and provided in Table IX below.

TABLE IX

| Covar matrix(*Satosa* only) | | 1st rotation | | | Covar matrix(*Versicolor* only) | | 1st rotation | | |
|---|---|---|---|---|---|---|---|---|---|
| $S_{pq}^{(1)}$ | x1 | x2 | x3 | x4 | $S_{pq}^{(1)}$ | x1 | x2 | x3 | x4 |
| x1 | 1.6796 | 0.0000 | 0.2086 | 0.0689 | x1 | 13.0552 | 4.1740 | 9.3610 | −0.4005 |
| x2 | 0.0000 | 11.4494 | 0.9630 | 0.6775 | x2 | 4.1740 | 4.8250 | 4.4908 | 0.5583 |
| x3 | 0.2086 | 0.9630 | 1.4778 | 0.2974 | x3 | 9.3610 | 4.4908 | 12.0821 | 0.0000 |
| x4 | 0.0689 | 0.6775 | 0.2974 | 0.5442 | x4 | −0.4005 | 0.5583 | 0.0000 | 0.6541 |

Table IX may be calculated by two alternate techniques. A first approach may employ results of a similarity transformation, previously described. A second approach may calculate results from a basis transformation, as also previously described. A similar approach in which correlation coefficients are employed to select a second rotation may be illustrated by Table X. Bold type indicates selected parameters or variables for rotation in this example.

TABLE X

| Corr.coeff(*Satosa* only) | | max rij selects 2nd rotation | | | Corr.coeff(*Versicolor*) | | max rij selects 2nd rotation | | |
|---|---|---|---|---|---|---|---|---|---|
| $r_{pq}^{(1)}$ | x1 | x2 | x3 | x4 | $r_{pq}^{(1)}$ | x1 | x2 | x3 | x4 |
| x1 | 1.0000 | 0.0000 | 0.1324 | 0.0721 | x1 | 1.0000 | 0.5259 | 0.7453 | −0.1370 |
| x2 | 0.0000 | 1.0000 | 0.2341 | 0.2714 | x2 | 0.5259 | 1.0000 | 0.5882 | 0.3143 |
| x3 | 0.1324 | 0.2341 | 1.0000 | 0.3316 | x3 | 0.7453 | 0.5882 | 1.0000 | 0.0000 |
| x4 | 0.0721 | 0.2714 | 0.3316 | 1.0000 | x4 | −0.1370 | 0.3143 | 0.0000 | 1.0000 |

Table XI below provides results for this example after a second rotation is applied. Note that several elements are zeroed as a result.

−0.284  Rot angle [rad]  −16.25  Rot ang [deg]  $\phi_{34}$ Setosa  −0.759  Rot angle [rad]  −43.51 Rot ang [deg]  $\phi_{13}$ Versicolor

TABLE XI

| Covar matrix(Satosa only) | 2nd rotation | | | Covar matrix(Versicolor) | 2nd rotation | | | |
|---|---|---|---|---|---|---|---|---|
| $S_{pq}^{(2)}$ | x1 | x2 | x3 | x4 | $S_{pq}^{(2)}$ | x1 | x2 | x3 | x4 |
| x1 | 1.6796 | 0.0000 | 0.2196 | 0.0078 | x1 | 21.9423 | 6.1190 | 0.0000 | −0.2904 |
| x2 | 0.0000 | 11.4494 | 1.1141 | 0.3810 | x2 | 6.1190 | 4.8250 | 0.3830 | −0.5583 |
| x3 | 0.2196 | 1.1141 | 1.5645 | 0.0000 | x3 | 0.0000 | 0.3830 | 3.1951 | 0.2757 |
| x4 | 0.0078 | 0.3810 | 0.0000 | 0.4575 | x4 | −0.2904 | 0.5583 | 0.2757 | 0.6541 |

Tables XII, XIII, and XIV below provide corresponding results as above for yet a third rotation transformation applied in this example.

TABLE XII

| Corr.coeff(Satosa only) | max rij selects 3rd rotation | | | Corr.coeff(Versicolor) | max rij selects 3rd rotation | | | |
|---|---|---|---|---|---|---|---|---|
| $r_{pq}^{(2)}$ | x1 | x2 | x3 | x4 | $r_{pq}^{(2)}$ | x1 | x2 | x3 | x4 |
| x1 | 1.0000 | 0.0000 | 0.1354 | 0.0089 | x1 | 1.0000 | 0.5947 | 0.0000 | −0.0767 |
| x2 | 0.0000 | 1.0000 | 0.2632 | 0.1665 | x2 | 0.5947 | 1.0000 | 0.0975 | 0.3143 |
| x3 | 0.1354 | 0.2632 | 1.0000 | 0.0000 | x3 | 0.0000 | 0.0975 | 1.0000 | 0.1907 |
| x4 | 0.0089 | 0.1665 | 0.0000 | 1.0000 | x4 | −0.0767 | 0.3143 | 0.1907 | 1.0000 |

TABLE XIII

−0.111  Rot angle [rad]  −6.35  Rot ang [deg]  $\phi_{23}$ Setosa  −0.310  Rot angle [rad]  −17.78  Rot ang [deg]  $\phi_{12}$ Versicolor

TABLE XIV

| Covar matrix(Satosa only) | 3rd rot | | | Covar matrix(Versicolor) | 3rd rot | | | |
|---|---|---|---|---|---|---|---|---|
| $S_{pq}^{(3)}$ | x1 | x2 | x3 | x4 | $S_{pq}^{(3)}$ | x1 | x2 | x3 | x4 |
| x1 | 1.6796 | 0.0243 | 0.2182 | 0.0078 | x1 | 23.9047 | 0.0000 | 0.1170 | −0.1060 |
| x2 | 0.0243 | 11.5734 | 0.0000 | 0.3787 | x2 | 0.0000 | 2.8626 | 0.3647 | 0.6203 |
| x3 | 0.2182 | 0.0000 | 1.4405 | −0.0421 | x3 | 0.1170 | 0.3647 | 3.1951 | 0.2757 |
| x4 | 0.0078 | 0.3787 | −0.0421 | 0.4575 | x4 | −0.1060 | 0.6203 | 0.2757 | 0.6541 |

Treelet rotation or rotation-type transformations have been completed for this particular example. A Jacobi method may continue in order to zero out off diagonal elements, but, as mentioned previously, this typically may not lead to further increase in Fisher distance.

TABLE XV

Figure 9:
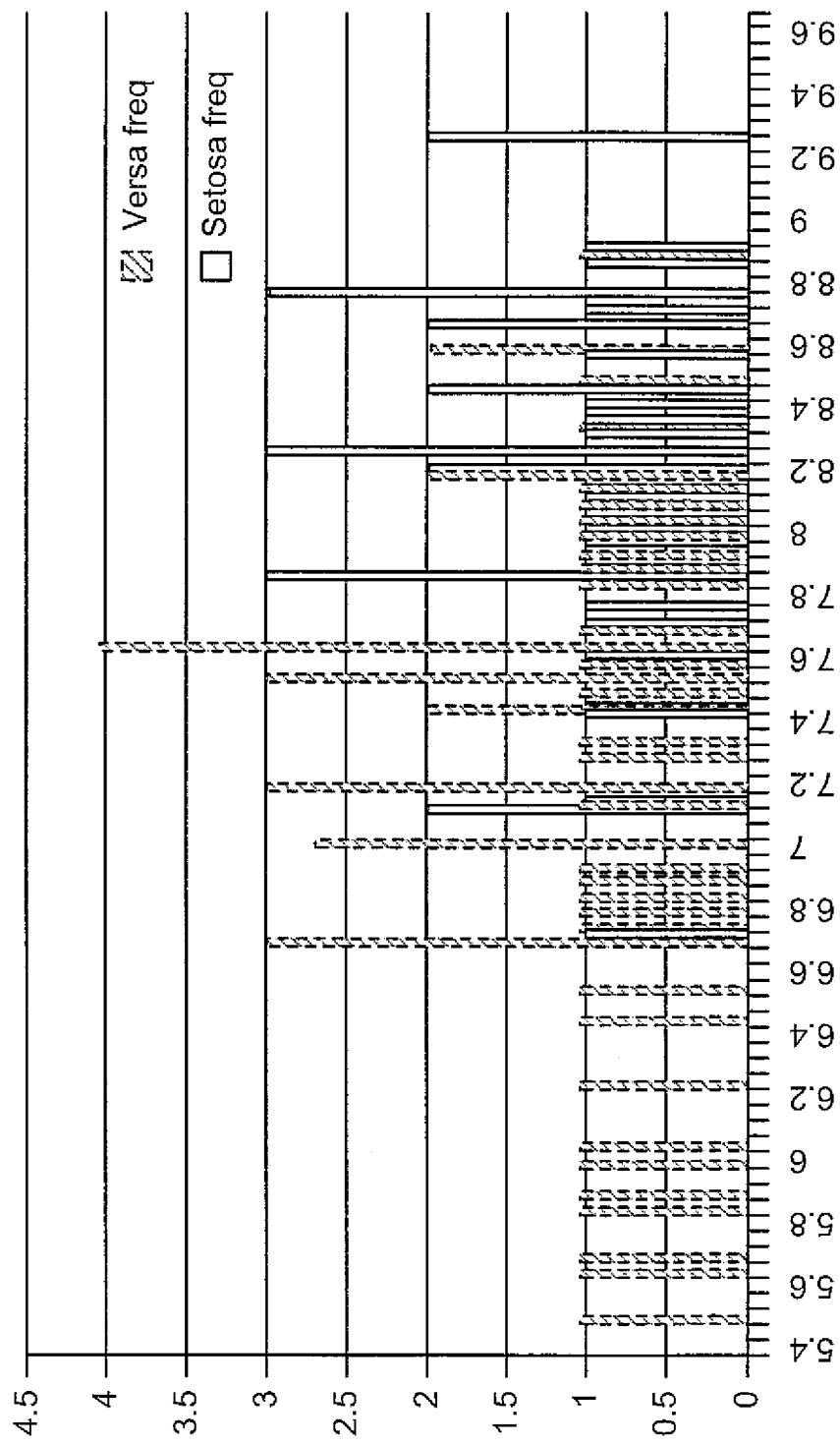
FIG. 9 is a plot illustrating a resulting frequency histogram of Treelet-transformed Setosa and Versicolor distributions.

| Iris setosa (Treelet Rotations of raw data) | | | | | | Iris versicolor (Rotations of raw data: Treelet) | | | | | |
|---|---|---|---|---|---|---|---|---|---|---|---|
| $X_1^{(1)}$ | $x_2^{(1)}$ | $x_3^{(2)}$ | $X_4^{(2)}$ | $X_2^{(3)}$ | $X_3^{(3)}$ | $x_3^{(1)}$ | $X_4^{(1)}$ | $x_1^{(2)}$ | $X_3^{(2)}$ | $X_1^{(3)}$ | $X_2^{(3)}$ | implement or apply these coordinate transformations to the set of training signal samples for this example. Resulting frequency distributions for Setosa and Versicolor are illustrated by FIG. 9. A Fisher score for Treelet transformed signal samples, as shown in FIG. 9, is provided as follows:

$X_{Setosa} = x_1^{(1)} + x_2^{(3)} + x_3^{(3)} + x_4^{(2)}$ $X_{Versicolor} = x_1^{(3)} + x_2^{(3)} + x_3^{(2)} + x_4^{(1)}$ Distribution of Treelet-rotated signal samples may now be calculated. In this particular example, a set of progressive coordinate transformations were identified above. Alternatively, a series of basis transformations may be applied to the previously provided training signal sample set of Table I to with a particular Treelet transformation indicated by a superscripted ( ) index. As seen in FIG. 9, for this particular example at least, Treelet rotational transformations alone do not appear to provide a disjoint class separation. The mean value for Setosa is $<X>_S = 8.07$ cm.

The mean value for Versicolor is $<X>_V = 7.24$ cm.

The difference in mean values of Treelet-transformed signal samples using transformations, as in this example, therefore may be a relatively small, $D_{SV} = 0.84$ cm.

Respective variances are $S_{Setosa}=0.33$ and $S_{Versicolor}=0.67$, which leads to an estimated average $S_{SV}=0.5$. Therefore, the Fisher distance for this case, after applying a Treelet approach, matches our intuition from viewing FIG. 9. The two categories or classes in this particular case do not appear to sufficiently separated:

$$F_{SV} \equiv \frac{1}{2} D_{SV} / S_{SV}^{1/2} = 0.83.$$

Of course, in other embodiments involving other sets of signal samples or signal sample values, it may be possible for application of rotational or rotational-type transformations to result in sufficient or adequate separation of category or class distributions; therefore, it is intended that claimed subject matter include embodiments that may employ rotational or rotational-type transformations, such as for a PCA or Treelet approach.

In contrast, however, continuing with this example, below illustrations of two possible shear or shear-type transformations are provided. Of course, these calculations are provided for purposes of illustration and it is not intended that claimed subject matter be limited in scope to these example calculations or to the particular transformations illustrated. Nonetheless, continuing with this example, to illustrate a first sample transformation, Treelet-rotations may be applied to linearly scaled, but otherwise unprocessed signal sample values. In this first sample transformation, for this example, we may begin with distribution vectors for scale-transformed categories:

$X_A^{(0)} = [\lambda_1 * x_1, \ldots, \lambda_2 * x_m]_A = |\lambda * x|_A$

Figure 10:
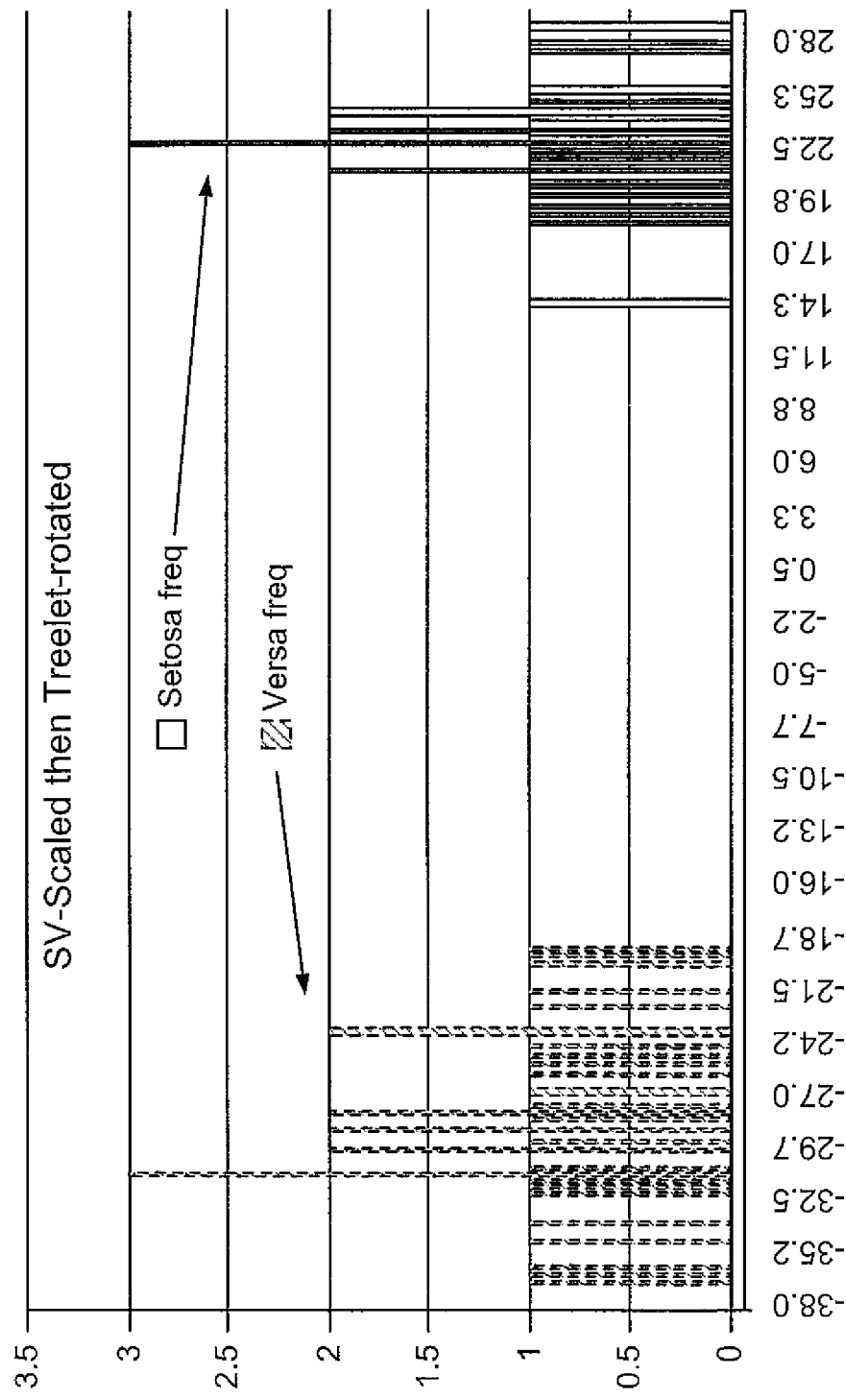
FIG. 10 is a plot illustrating a resulting frequency histogram of Setosa and Versicolor distributions applying a first shear transformation.

A sequence of Treelet-Jacobi rotations may be applied, as before, but, in this first sample transformation, after a scaling transformation has been applied. Resulting transformations may yield the following:

$X_{Setosa} = \lambda^*_1 x_1^{(1)} + \lambda^*_2 x_2^{(3)} + \lambda^*_3 x_3^{(3)} + \lambda^*_4 x_4^{(2)}$ $X_{Versicolor} = \lambda^*_1 x_1^{(3)} + \lambda^*_2 x_2^{(3)} + \lambda^*_3 x_3^{(2)} + \lambda^*_4 x_4^{(1)}$ FIG. 10 is a plot illustrating a resulting frequency histogram of shear-transformed Setosa and Versicolor distributions. This particular first sample shear transform comprises a linear scaling transformation followed by a Treelet-rotation transformation.

The mean value for Setosa is:

$<X>_S = 22.9$ cm.

The mean value for Versicolor is:

$<X>_V = -27.8$ cm.

The difference in mean values of Treelet-transformed measurements or signal sample values may be computed to be:

$D_{SV} = 50.7$ cm.

Respective variances of individual species are:

$S_{Setosa} = 2.69$ and $S_{Versicolor} = 4.30$, which leads to $S_{SV} = 3.49$

Fisher distance for this case may therefore be computed to be:

$$F_{SV} \equiv \frac{1}{2} D_{SV} / S_{SV}^{1/2} = 7.3.$$

Likewise, inspection of FIG. 10 indicates that a reasonable separation between distributions as a result of the applied transformation(s) appear to occur.

Figure 11:
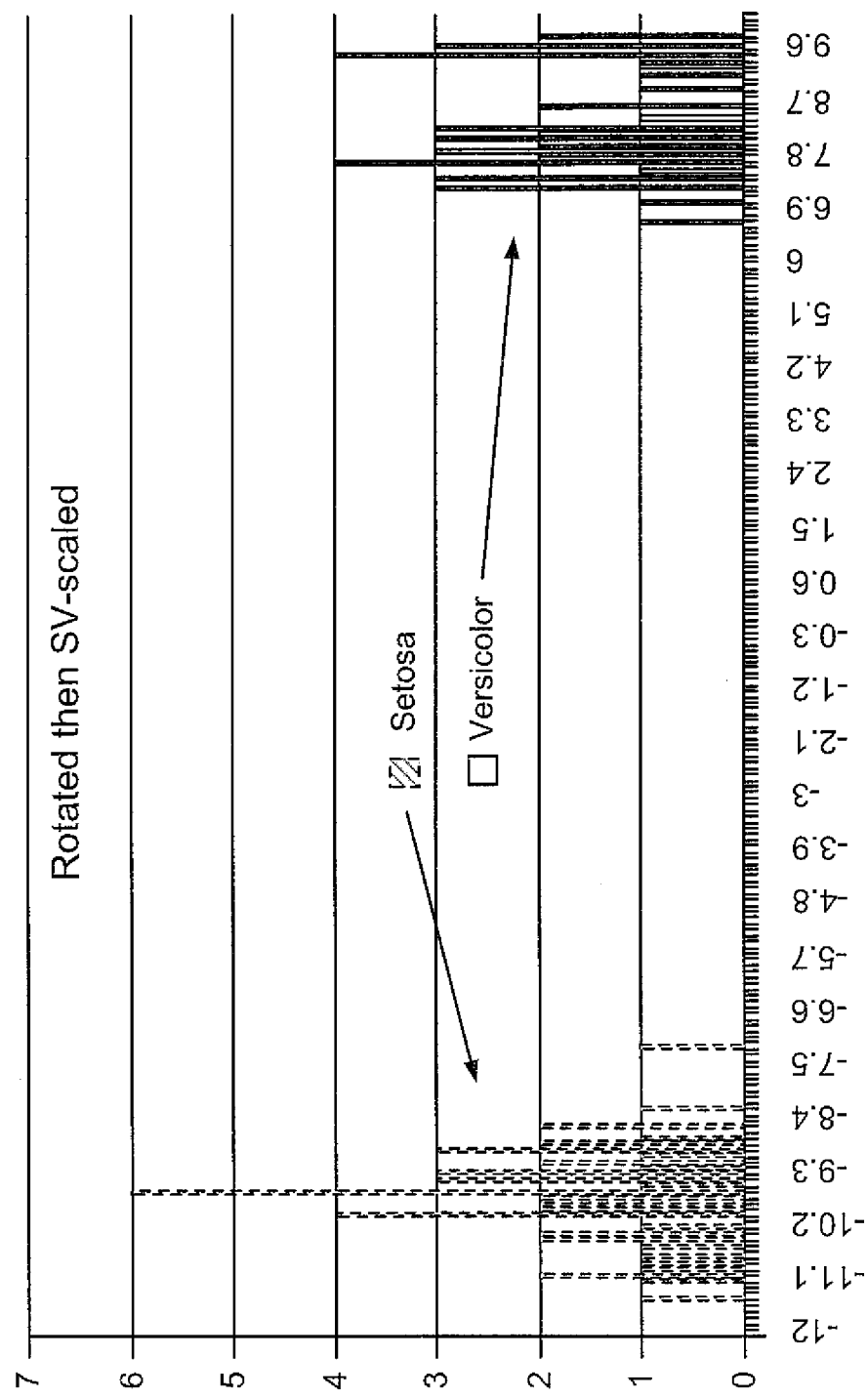
FIG. 11 is a plot illustrating a resulting frequency histogram of Setosa and Versicolor distributions applying a second shear transformation.

Next, instead, continuing with this example, for a second sample transformation, we may apply Fisher's linear discriminant method of transformation to Treelet rotated signal sample values to see if an improvement in class separability occurs. This second sample transformation, a combination of operations or transformations, comprising a Treelet-rotation transformation followed by a Fisher-scaling transformation, may be equivalent to a linear shear transformation. We start with:

$X_{Setosa} = \lambda_1 x_1^{(1)} + \lambda_2 x_2^{(3)} + \lambda_3 x_3^{(3)} + \lambda_4 x_4^{(2)}$ $X_{Versicolor} = \lambda_1 x_1^{(3)} + \lambda_2 x_2^{(3)} + \lambda_3 x_3^{(2)} + \lambda_4 x_4^{(1)}$ and may solve for $\lambda_j$ as described above. Leaving out details as the calculations are otherwise similar to previous calculations, FIG. 11 is a plot of a frequency histogram of shear-transformed Setosa and Versicolor distributions. The shear transform in this second example transformation comprises SV-scaling of previously rotation transformed training signal sample values.

The mean value for Setosa is:

$<X>_S = -9.71$ cm.

The mean value for Versicolor is:

$<X>_V = 8.16$ cm.

The difference in mean values is:

$D_{SV} = 17.9$ cm

Average variance is $S_{SV} = 0.85$.

Fisher distance for this case may then be computed to be:

$$F_{SV} \equiv \frac{1}{2} D_{SV} / S_{SV}^{1/2} = 10.7.$$

We note that this separation appears to be greater than the separation that resulted from the previous or first sample shear transformation. These two sample transformations applied to sample values from Table I appears to demonstrate that a shear or shear-type transformation comprising rotation and scaling operations or transformations is not commutative. That is, depending at least in part upon order of application of rotation and scaling transformations, different separations between distributions may be produced. In an embodiment, choice of which operation or transformation to apply first may depend at least in part on the nature of the particular set of distributions involved. Therefore, for an embodiment, for example, empirically it may be desirable to compute or apply a shear or shear-type transformation using differing orders of rotation or rotation-type and scaling or scaling-type transformations to see which order produces a larger separation of distributions.

TABLE XVI

| SV-scaling used | Mean separation D | std. dev. $S^{1/2}$ | Fisher distance $D/(2\, S^{1/2})$ |
| --- | --- | --- | --- |
| Fisher's scaling | 33.8 | 3.4 | 5.0 |
| Treelet rotation | 0.84 | 0.5 | 0.8 |
| Treelet rotation of scaled data | 50.7 | 3.5 | 7.2 |
| Scaling of rotated data | 17.9 | 0.85 | 10.7 |

Table XVI above compares Fisher distances produced by applying varying transformations to sample values from Table I. As Table XVI indicates for these example sample values, the second sample shear transformation appears to double the Fisher distance between classes Setosa and Versicolor, that is, applying scaling produces a distance of 5, whereas the second sample shear transformation produces a distance of 10.7. As indicated previously, for an embodiment, increasing Fisher distance may result in a reduction of misclassification probability, assuming, for example, Normally distributed signal samples. Therefore, while, as previously indicated, claimed subject matter is not limited in scope to applying a shear or shear-type transformation to training signal samples or training signal sample values, in at least one embodiment, a shear or shear-type transformation may be employed so that distributions may be sufficiently separated so that a satisfactorily low probability of misclassification may be realized.

The particular illustrative examples or embodiments described above address situations involving separation of two classes or categories through application of a shear or shear-type transformation, although claimed subject matter is not limited in scope in this respect. For purposes of illustration, additional embodiments are described below which may address a wide range of potential situations in which the number of classes or categories may exceed two classes or categories.

For example, in at least one embodiment, there may be a single particular category $A_0$ of primary interest. For example, $A_0$ might represent a rare cell type, which may be found or categorized, and categorization of other classes that may be present may not viewed as necessarily being as desirable. In at least one embodiment, therefore, the other remaining categories that may be present may be treated as belonging to a class set $\{B_k\}$ where $k \geq 1$ and where increasing separation of the $\{B_k\}$ categories relative to one another is not necessarily a signal processing goal for this particular example embodiment.

In at least one embodiment, for example, calculations may be performed to obtain scores for a scale transformation $\vec{\lambda}_{A_0 B_1}$ obtained from comparing $(A_0, B_1)$. In general, for an embodiment employing this or a similar approach, $A_0$ and $\{B_k\}$ may be considered as already having rotation transformations applied to them prior to applying a scale transformation, as previously described. Likewise, calculations may be performed to obtain scores using $\vec{\lambda}_{A_0 B_1}$ as a scale transformation applied to all other or remaining classes, e.g. by calculating $$X_{B_k} = \Sigma \lambda_j x_j.$$

The above procedure was, for example, used previously to derive scores for Versicolor, as shown in FIG. 8.

In an embodiment that may employ this or a similar approach, one may then proceed to calculate some, or all other, pair wise scale transformations as above involving $A_0$. Hence, $\vec{\lambda}_{A_0 B_k}$ and associated scores may be derived for $B_k$ in an embodiment.

For other embodiments, of course, other prioritizations may be used, of course, for selecting a particular order for $B_k$. For example, for an embodiment, after performing initial calculations, a category $B_p$ closest to $A_0$ as indicated by Fisher distance may be selected. For a particular selected category, $B_p$, a shear or shear-type transformation may be found which may produce a sufficient separation from $A_0$ in accordance with Fisher distance $F_{A_0 B_p}$. Therefore, for an embodiment employing this or a similar approach, adequate separation of $A_0$ from class or category $B_p$, which was found to be the closest distribution, may result. As before, for an embodiment, scores may then be derived. In this manner, for an embodiment, a sequence of $\vec{\lambda}_{A_0 B_k}$ and associated scores may be derived so that members $B_p$ from the set $\{B_k\}$ may be employed to determine a scale vector in conjunction with $A_0$.

In another potential embodiment, there may be no preferred class or category. In effect, classes or categories may be considered of equal relative interest. Assume that there are n elements or categories in $\{A_k\}$ then the total number of 2-element subsets may be given by $\binom{n}{2} = n!/2!(n-2)!$.

Once again, in general, for an embodiment employing this or a similar to approach, members of the set $\{A_k\}$ may be considered as already having rotation transformations applied prior to applying a scale transformation, as previously described. Likewise, calculations may be performed to obtain scores for members of the set using a particular $\vec{\lambda}_{A_k A_j}$ scale transformation.

In an embodiment, one may then proceed to calculate some, or all other, pair wise scale transformations $\vec{\lambda}_{A_p A_q}$ and associated scores. As before, various prioritizations may be employed for determining an order of subsequent scaling calculations. One example of an approach to prioritize calculation of pair wise scale factors for an embodiment may involve scaling calculations for 2-element subsets, which may already have a shear or shear-type transformation calculated for that particular class pair if different transformation orders of rotation and scaling had been employed to identify which order produces a wider separation or greater Fisher distance.

In an embodiment, the class that is most near using Fisher distance $F_{A_j A_k}$ may be identified. The resulting transformation may then be applied to all category pairs for an embodiment. Likewise, an embodiment may apply iterations to achieve a desired class separation or until no further substantial improvement appears to be obtained among the set.

Continuing or extending approaches alluded to above, in at least one particular embodiment, an approach may be employed to provide or produce an extended multidimensional distance by employing pair-wise scaling calculations to specify relations among distributions. Likewise, distributions may then be further separated, as is desired. An example case of three distributions is provided in detail below as an illustration. Again, although specific embodiments are illustrated using signal sample values provided by Table I, claimed subject matter is not limited in scope to these particular illustrations. Many other approaches are possible and are intended to be included within the scope of claimed subject matter. However, larger numbers of categories may be processed in a similar manner as is illustrated below for three categories, although, as noted above, the number of combinations of pair categories for scaling appears to grow as $$\binom{n}{2}.$$

For this particular embodiment, we apply rotation transformations for distributions S, V, Va and may then proceed to apply scaling transformations $$\binom{3}{2} = 3!/2!(3-2)! = 3 \text{ ways;}$$

e.g., SV-scaled, VVa-scaled, SVa-scaled, by treating the three categories in pairs in this example. Table XVII below displays the first of these three cases: SV-scaling, which was previously described in detail, see, e.g., Table XVI and associated results.

TABLE XVII

SV-scaling of rotated measurement signal

| SV | VVa | SVa | Distribution pair |
|---|---|---|---|
| 10.7 | 0.8 | 8.2 | Fisher distance |
| 17.9 | 1.6 | 16.3 | Mean separation |

| | $<X>_A$ | $S_{SV}^{1/2}$ | | $\sigma^2$ | $\sigma$ |
|---|---|---|---|---|---|
| Virginica (Va) | 6.6 | | 0.98* | 0.97* | 1.23 | 1.11 |
| Versicolor (V) | 8.2 | 0.85 | | | 0.73 | 0.85 |
| Setosa (S) | −9.7 | | | | 0.68 | 0.82 |

Table XVII provides first and second order statistics for SV-scaling of signal sample values that were previously rotation transformed for the three categories for this example. Parenthesis ( ) indicates an average of two individual categories statistics were used, no parenthesis indicates variance within species.

Likewise, for this example, Table XVIII and Table XIX provides similar calculations for corresponding other situations, VaV-scaling of rotation transformed signal sample values and VaS-scaling of rotation transformed signal sample values, respectively.

TABLE XVIII

VaV-scaling of rotated measurement signal

| SV | VVa | SVa | Distribution pair |
|---|---|---|---|
| 7.6 | 3.9 | 4.2 | Fisher distance |
| 584 | 268 | 316 | Mean separation |

| | $<X>_A$ | $S_{SV}^{1/2}$ | | $\sigma^2$ | $\sigma$ |
|---|---|---|---|---|---|
| Virginica (Va) | 218 | | 34.7 | 37.7* | 1108 | 33.3 |
| Versicolor (V) | −50 | 38.6* | | | 1231 | 35.1 |
| Setosa (S) | 534 | | | | 1773 | 42.1 |

TABLE XIX

SVa-scaling of rotated measurement signal

| SV | VVa | SVa | Distribution pair |
|---|---|---|---|
| 10.4 | 0.9 | 8.4 | Fisher distance |
| 15.0 | 1.6 | 13.4 | Mean separation |

TABLE XIX-continued

SVa-scaling of rotated measurement signal

| | $<X>_A$ | $S_{SV}^{1/2}$ | | $\sigma^2$ | $\sigma$ |
|---|---|---|---|---|---|
| Virginica (Va) | 6.7 | | 0.85* | 0.80 | 0.80 | 0.89 |
| Versicolor (V) | 8.3 | 0.72* | | | 0.65 | 0.81 |
| Setosa (S) | −6.7 | | | | 0.38 | 0.62 |

In an embodiment, a three-dimensional metric may be employed, such as for this case of three classes, a metric for this example may be component-wise based on the previously discussed Fisher-metric. The three dimensions may correspond to three scaling measures between class pairs. As noted, in an embodiment applying a similar approach, but with additional dimensions, for example, as dimensionality grows, likewise computation complexity appears to grow as, $$\binom{n}{2} = n!/2!(n-2)!$$

where n equals the number of categories for pair wise scaling. Vectors in this example may be expressed in terms of a relation between a class pair from the set {A, B, C}, as shown below:

$$\vec{A} \cdot \vec{B} = [F_{AB}(\lambda_{AB}), F_{AB}(\lambda_{BC}), F_{AB}(\lambda_{CA})]$$

where $\lambda_{AB}$ denotes a scale factor derived from pair A,B and $F_{AB}$ comprises the Fisher distance between the respective two distributions.

Lengths of these vectors may be computed as:

$$\|\vec{S} \cdot \vec{V}\| = \sqrt{10.7^2 + 7.6^2 + 10.4^2} = 16.7$$

$$\|\vec{S} \cdot \vec{Va}\| = \sqrt{8.2^2 + 4.2^2 + 8.4^2} = 12.4$$

$$\|\vec{Va} \cdot \vec{V}\| = \sqrt{0.8^2 + 3.9^2 + 0.9^2} = 4.1$$

A vector's components may be derived from respective Fisher distances. Note also that the three vectors lengths are additive in this example:

$$\|\vec{S} \cdot \vec{Va}\| + \|\vec{Va} \cdot \vec{V}\| = \|\vec{S} \cdot \vec{V}\|.$$

Through the approach described, which in another embodiment, for example, may be applied to larger numbers of categories or classes, as previously mentioned, a greater separation between distributions may be realized, as occurred in this example. As demonstrated, in at least one embodiment, second order statistics may be employed to perform calculations providing information regarding distribution separation, although at a cost of greater computational complexity. However, as this is primarily a cost to be incurred during creation of libraries for supervised learning, the cost incurred generally speaking may be incurred offline and may likewise provide a countervailing benefit in reducing probability of misclassification.

A situation in which one specific category is of primary interest, as mentioned previously, may represent a simpler situation in comparison with the situation illustrated immediately above, which uses information from pair wise distribution calculations of associated scale factors. As alluded to above, complexity may grow with n, the number of categories. For an embodiment and a given situation, it may be prudent to weigh computational costs against benefits of greater separation of distributions.

Likewise, parallelization may be applied in at least one embodiment since initial rotation transformations may be associated with individual distributions and whereas subsequent scaling may occur between distribution pairs. During a real time sampling phase, associated shear operations may be carried out, as described, although with a sequence of scores assigned to obtain an associated n-dimensional score vector. Computational costs may therefore be reduced for some situations in that rotation angles and scale factors may be stored in conjunctions with created libraries.

As discussed previously, alternate embodiments may include affine transformations augmenting linear shear transformations, extensions to non-linear methods by use of genetic processes or application of support vector machine processing, for example.

Information theoretic estimates may provide a limit on number of categories for an embodiment. To get a large upper bound, one may assume, for a given situation, for example there is no noise and there are p independent measurements with a measurement having k bits/dimension. Thus, kp bits may be available, which comprises the entropy. Now let there be j<k noisy bits. Then (k−j) comprise the equivocation so there may be (k−j)p information states for the particular situation.

In practice, not all measurement dimensions are necessarily independent. If the number of independent variables may be identified for a particular situation, e.g. a full Treelet decomposition, one may assume in the situation the number independent variables is q<p. An upper bound on the number of classes in the situation may therefore be (k−j)q. As an example, assume there are 14 bits per channel with 4 bits of noise per channel. If there are 8 measurements, but 3 independent variables, then there may be a maximum of 30 classes, capable of being unambiguously defined.

In general, for an embodiment, time and effort may be invested to create useful training sample distributions. Computational complexity for an embodiment, such as may be associated with processes such as those previously discussed, may be managed by off line processing. If desirable, for an embodiment, sample distributions may be enhanced by increasing resolution, e.g., reducing pixel size to potentially reduce category mixing within a pixel. Of course, a lower limit to this procedure may exist as empty pixels eventually may result with noise, in effect, swamping signal.

In operation, in at least one embodiment, a defined set of score distributions, with associated scaling and rotation parameters, and spectral characteristics $I_A(\lambda_m)$ may be stored in an application library. For example, in an embodiment, one may be stored for a category, e.g. for a cell type or intracellular component. During operation, a system embodiment may be employed to detect spectra over a sample and generate a frame of signal sample values, which may be transmitted to a computing device or computing platform, such as, in one embodiment, a host computer.

A computer or computing platform, therefore, in at least one embodiment, may coordinate processing of incoming frames via application layer processes being executed as well as coordinating storage of unprocessed frames of captured signal samples and coordinating storage of categories associated with selected image field pixels, for example. Pixels of an image field may be associated with intensity vectors measuring collected intensity as a function of wavelength, for example. Captured frame signal sample values and categorized image field pixels may then be stored for later use or processing. To the extent that incoming frames of signal sample values may be processed in real time, in at least one embodiment, through design or system architecture for at least one embodiment, no significant impact to overall system throughput should result.

In at least one embodiment, for an image field pixel, for example, a process being executed may assign a category along with a probability of belonging to the category. Incoming pixels may be scored based at least in part on category libraries and application of coordinate transformations, such as those previously discussed, for example, to aid in improved scoring performance. An incoming image field pixel, for example, may have an associated vector of measurements obtained from m-frames of captured signal sample values $$[x_1^{(0)}, \ldots, x_m^{(0)}] = |x^{(0)}\rangle = [\hat{I}(\lambda_1), \ldots \hat{I}(\lambda_m)].$$

In at least one embodiment, a measured pixel-vector may be compared with one or more category libraries, such as those discussed previously in connection with execution of a training phase. A measured vector obtained during real time sampling may, for example, be transformed in a manner similar to transformations discussed previously in connection with a training phase, for example. For example, in at least one embodiment, a single signal sample value or datum per pixel may be captured, which may be transformed, scored, and a probability of membership assigned. In at least one embodiment, as in a training phase, a sample pixel signal value may be operated on, such as by particular shear or shear-type operations, such as those previously discussed, which, in at least one embodiment, may be selected to increase distribution separation and thereby reduce risk of category misclassification, for example.

Here, a specific example is provided for illustration purposes, although claimed subject matter is not limited in scope in this respect. Assume N-classes have been established during a training phase. Therefore, in at least one embodiment, a library of trained distributions, class-pair scaled factors, and rotations per class $\{A_j; \lambda_{j,k}; \theta_j\}$ may be stored and available for use in signal processing. Unprocessed signal sample values may arrive, during operation of a system embodiment, as a vector $\vec{x} = [x_1^{(0)}, \ldots, x_p^{(0)}] = |x^{(0)}\rangle$ with p-dimensions.

In at least one embodiment, if no rotations are applied, a scale factor may be applied to unprocessed signal sample values to create a per pixel score for a class or category pair $A_j, A_k$, for example:

$$X(\lambda(j,k)) = \overrightarrow{(\lambda(A_j, A_k))} \cdot \vec{x}_{sample}.$$

An incoming pixel-vector may thus be transformed and receive a score, associated with one or more categories of interest. In at least one embodiment, scores may be based at least in part on a Fisher distance $F_{AB}$ calculated, for example, for two classes A and B. If, however, for example, rotations are first applied prior to deriving a class pair scale factor, $(\lambda(A_j, A_k))$, two scores may be generated per pixel sample value or datum, in at least one embodiment:

$$X(\theta_k, \lambda_{jk}); X(\theta_j, \lambda_{jk})$$

In at least one embodiment, if rotations are employed on a per class basis, various rules to assign class probabilities may be applied. Consider first, for example, that distributions may be disjoint, e.g. $A \cap B = \emptyset$, where $\emptyset$ comprises the empty set.

As an example, consider a case or situation in which no rotations are applied for an embodiment. If a sampled pixel vector score falls within a distribution of A or B, then a sample may be assigned to a corresponding class. Without loss of generality let $\langle X \rangle_j \ll \langle X \rangle_k$. In an embodiment, for example, a rule may comprise the following conditions. One might choose a rule that a sampled pixel vector is to be assigned to A if it's score X<a maximum score, where A<B, for example:

If $X(\lambda(j,k)) \leq X(A_j)\max$; then $p_j=\text{prob}(X\epsilon\{A_j\})=1$ Therefore, in this example embodiment, a value of 1 may be assigned to a sample signal value as being a member of class $A_j$ since its score falls less than or within a range of training scores for class $A_j$. A corresponding rule for class $A_k$ may therefore, in an embodiment, comprise:

If $X(\lambda(j,k)) \leq X(A_k)\min$; then $p_k=\text{prob}(X\epsilon\{A_k\})=1$ Otherwise, for an embodiment, if a signal sample value score falls in between values of scores for disjoint classes $A_j$ and $A_k$, the following probabilities may be assigned for being associated with respective categories:

$p_j=\text{prob}(X\epsilon\{A_j\})=[A_k(\min)-X]/([A_k(\min)-A_j(\max)]$ $p_k=\text{prob}(X\epsilon\{A_k\})=[X-A_j(\max)]/([A_k(\min)-A_j(\max)]$ Note that $p_j+p_k=1$.

For other embodiments, other probabilities may likewise be applied to situations where a score X falls between scores of A and B, but is not contained within a training distribution and it is desired to assign a probability to X of being in A and a probability of X being in B. For example, this may occur if a sample X comprises a mixture of A and B or other categories, e.g. an image pixel may include both A and B spectra. Likewise, in an embodiment, to associate another probability with a class, for example, one could create another probability assignment rule by replacing $A_k(\min)$ with $<X>_k$ and $A_j(max)$ with $<X>_j$.

This latter rule can also be used in situations in which distributions overlap, e.g., $A_k \cap A_j \neq \emptyset$. Furthermore, "closeness" metrics may be devised and employed, e.g. distance of a sample score to a median. As an example, let $x_A=X-<A>$ be distance of a sample to a mean of A and $x_B=X-<B>$ be distance of a sample to a mean of B. In an embodiment, a probability of X being a member of A may therefore be assigned $\text{Prob}_A(X)=x_A/D_{AB}$ and a probability of X being a member of B may be assigned $\text{Prob}_B(X)=x_B/D_{AB}$. Typically, chances of this situation arising may be reduced by various approaches, such as, for example, those described previously in connection with training, including applying retraining in response to one or more false positives or false negatives. However, again, it may be that in some situations, A and B distributions remain overlapped. This could occur in various situations. For example, a user may wish to model a finite-member set created during training by one of any of a host of continuous distributions or by one of any of a host of infinite member discrete distributions, which might imply some probability of overlap regardless of sample score.

In at least one embodiment, a modification of the above probabilities $p_j$ may be made if rotational transforms are applied prior to scaling. For example, in an embodiment, X may be replaced by $$X = \frac{1}{2}[X(\theta_k, \lambda_{jk}) + x(\theta_j, \lambda_{jk})]$$

Otherwise assignment to a class may remain as previously described, for example, in an embodiment.

In at least one embodiment, another rule may be applied such that exclusive membership may be employed for A or B. This may, for example, dispense with assigning partial probabilities to both classes or categories. In this situation, a sample may be assigned a class using a score intended to measure proximity or "closeness." Of course, depending on a variety of factors, in an embodiment, for example, closeness may be measured in terms of means, medians, or Fisher distance in which A and B are separated by a halfway point in accordance with a difference of their means. Other scoring comparison methods may also be used based at last in part on various metrics between deterministic functions for respective categories and captured signal sample values, e.g. mean square error. In at least one embodiment, therefore, a category label, and possibly a probability, may be attached to a signal sample vector and stored for later use.

It may also, in an embodiment, be of interest to obtain further information about cell type, intracellular component, or other entity. A second examination of a selected sample field at higher resolution of spectra or spatial images may be useful or desirable. An example without limitation comprises trophoblast identification. A second pass examination of rare cells may be used to determine additional information, such as number of chromosomes. In the case of rare blood cells, a second pass might correspond to examining 1~10 fields in total out of roughly 48,000 image fields corresponding to a case of imaging a 300 mm diameter substrate using a 1.45 mm² CCD image field.

In an embodiment, a second pass may involve directing optics to particular image or sample fields of interest. For example, in an embodiment, x-y coordinates may be stored with an image frame of signal sample values. Sample location information, for example, may originate from mechanical stage position coordinates provided by encoders or interferometers. Fiducial marks may also exist on a substrate to capture a position relationship between a stage and substrate coordinates.

Second pass, higher resolution spectral detection or spatial imaging may employ increased magnification. Magnification may be adjusted, in an embodiment, for example, by some combination of changing zoom or objective lens strength or sample to lens working distance. A 60× objective with NA=0.9 in air may improve spatial resolution to 0.3 µm, for example. Spatial resolution may be evaluated in accordance with the Rayleigh formula R=0.6 lambda/NA with axial tolerance or depth of focus (DOF)=0.5·lambda/NA².

In at least one embodiment, dual ray optics may decouple illumination and sample-sensor image branches and may provide variable magnification control. Light flux of a sample and magnification of a sample object-field onto a sensor pixel array may be varied independently using separate illumination and zoom lenses. In an embodiment, for example, it may be desirable to avoid, if possible, use of an objective lens, which may affect both legs of the optics. Effective pixel size at a sample object-field may be varied using a zoom lens, for example. In an embodiment, an adjustment to sample light flux may be independently made by adjusting illumination lens 22 of FIG. 5.

In an embodiment, a wavelength dependent point spread, contrast or modulation transfer may measure image contrast or resolution. In cases where spatial image processing involves having improved resolution, a single wavelength may be selected to reduce chromatic effects from broadband illumination in at least one embodiment, for example.

Figure 12:
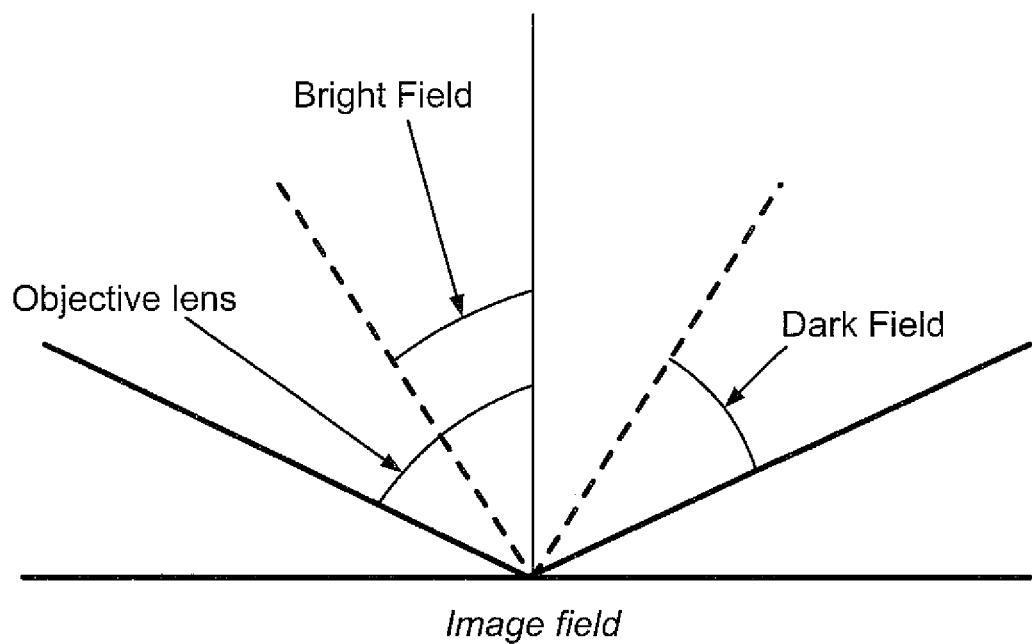
FIG. 12 is a schematic diagram illustrating different acceptance semi-angles for various optics collection modes or embodiments.

Further image enhancements may accrue via spatial filtering interposed in collection optics. Fourier filtering, for example, may be placed or implemented within an object-field to camera transfer optic, e.g. within zoom lens 17. Low angle scattering and source specular reflection off of a sample may generate a bright field (BF) image, while dark field (DF) images may occur by blocking BF collection angles, as shown, for example, in FIG. 12. Bright field (BF) and dark field (DF) light collection are somewhat analogous to flow cytometry forward- (FS) and side-scattered (SS) detection. It has been recognized that sub-Rayleigh resolution entities, e.g. fluorophore or fluorescent tags, may have sufficient scattering cross sections to create detectable events.

Coherent imaging may enhance diffraction effects and degrade a modulation transfer function. Coherent illumination may have a relatively small impact on resolution. Coherence effects, in an embodiment, may be further reduced by keeping illumination angles large compared to imaging collection angles. In an embodiment, spatial images may be accessible from digitized images produced by a sensor array or indirectly from spectrally categorized frame signal sample values.

Figure 13:
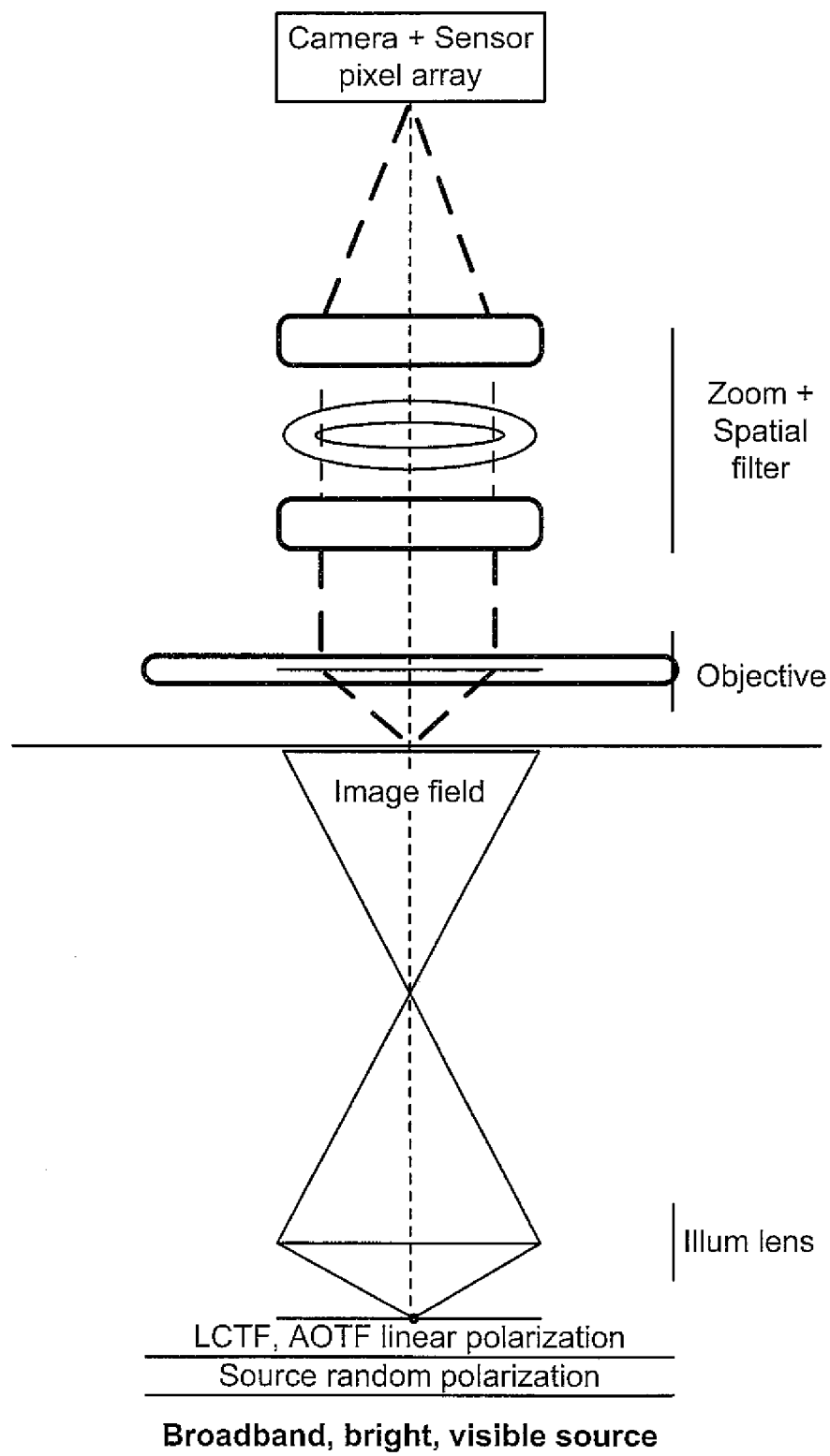
FIG. 13 is a schematic diagram of another possible embodiment of a system, such as a system for image rendering or spectral recognition, in accordance with claimed subject matter.

An alternate embodiment may be to use a transmission optic to illuminate a sample, as shown in FIG. 13. A benefit of this approach may be that a beam splitter may be omitted, which may double transmission efficiency.

A tradeoff may be that transmission properties of a substrate may become a factor in optics efficiency. A thin quartz substrate could be used in an embodiment. Substrate transmission efficiency may be greater than 50% for this to be an advantage. A stage assembly may be employed to hold a sample substrate on a periphery to reduce or avoid interference with light illumination and collection.

A measured random variable intensity $\hat{I}$ may be described in terms of related distributions and density functions as an approach to compare methods or embodiments. A flow cytometer may illuminate a sample fluid flowing through a detection volume and may detect a time series of events via a photomultiplier tube (PMT) intensity I at wavelength $\lambda_j$ $$\hat{I}(\lambda_j, t).$$

In an embodiment, simultaneous or nearly simultaneous detection of low angle, forward elastic scatter (FS) and high angle, 90 degree, side scatter (SS) may be achieved with two photomultipliers. These scattering modes may be correlated to cell size and granularity changes. In an embodiment, corresponding histograms and cryptograms may respectively be created from $$f(\hat{I}_{FS}(\lambda_j)) = \int_0^T f(\hat{I}_{FS}(\lambda_j), t) dt$$

and from joint densities $$f(\hat{I}_{FS}(\lambda_j), \hat{I}_{SS}(\lambda_k)).$$

In spite of hydrodynamic effects of sheath fluid, in an embodiment, useful structural information may be inferred about detected cell types by measuring joint distributions of FS and SS. In an embodiment, Rayleigh scattering may dominate SS detection; while overall cell sizes, which may typically be larger than incident wavelength, may dominate FS.

Beam propagation in a weakly absorbing medium (case with no exogenous tags) is governed by Beer's law, which for a constant absorption coefficient $\alpha$ may be described as:

$$\log(I_1/I_2) = -\alpha l = -k_0 n \kappa$$

where $k_0 = \omega/c$ comprises a free-space wave number, $l$ is the sample size, $n$ the index of refraction, and $\kappa$ attenuation index of the medium. Relative importance of weak absorption may be a factor affecting desirability of employing such embodiments.

For an embodiment in accordance with claimed subject matter, for example, bright field images may correspond roughly to a FS flow cytometer mode. A dark field may be associated with SS. One may desire to choose exclusively either DF or BF imaging. So, for an embodiment, to derive corresponding cell type may involve recourse to determining size distributions from spectral information. For elastic scattering, wow well flow cytometer distributions compare with distributions for an embodiment, for example, may influence whether or which particular embodiments may be desirably employed.

Illumination and collected intensities may differ in wavelength if, for an embodiment, fluorophores are used as sample tags. But as previously described, a histogram of time-integrated density may be commonly used as a starting point for processing of a cell population $$f(\hat{I}(\lambda_j)) = \frac{1}{N} \int_0^T f(\hat{I}(\lambda_j), t) dt$$

and N is a normalization constant. A measured probability density function of intensity at a given detected wavelength for a population detected over a time interval T may be employed for example in an embodiment. In an embodiment, events recorded by a PMT may be associated with presence of a cell, or tagged entity in a detection volume. In an embodiment, flow-cytometer fluid flow may be limited so that a detection event may be associated with a single cell or tagged entity.

In an embodiment, two or more PMT detectors may simultaneously or nearly so measure intensities at various wavelengths. A cytogram refers to joint density of two wavelengths $$f(\hat{I}(\lambda_j), \hat{I}(\lambda_k))$$

which may be used to further differentiate the population. In an embodiment, multiple cytograms may be formed from other joint distributions limited by number of detected wavelengths accessible in a flow-cytometer.

Side scattered light may be further complicated by inelastic interaction of fluorophores, if present, for an embodiment. It is conceivable, for an embodiment, that spectra of an individual event $$I(\lambda, t)$$

might be measured by synchronizing PMT detection electronics. Likewise, an embodiment in accordance with claimed subject matter, for example, may measure single particle and intra-cellular spectra with submicron resolution.

In an embodiment, flow cytometer event detection using side scattered light emanating from tagged fluorophores may provide sub-micron detection resolution. This is analogous to dark field microscopy, which may detect particles smaller than the Rayleigh spatial resolution limit.

An embodiment in accordance with claimed subject matter, for example, may detect a two dimensional spatial array of information for a wavelength $$\hat{I}(x_{jm}, y_{km}; \lambda_i).$$

A double index on spatial variables x, y is for summation within an image field m and for image fields across a sample. Spectral and spatial information may therefore potentially be captured on a per pixel basis for an embodiment.

An intensity histogram analogous to those used previously is $$f(\hat{I}(\lambda_p)) = \frac{1}{N} \sum_m^{image\ fields} \sum_{jk}^{datacube\ m} \hat{I}(x_{jm}, y_{km}; \lambda_p)$$

with an entire sample, for example, being measured at a given wavelength in an embodiment. Joint distributions are similarly formed.

Cell sorting is another capability provided by some flow-cytometers, which may be achieved by electrostatic deflection of cells as they pass downstream from a detection volume. For an embodiment in accordance with claimed subject matter, for example, cell sorting may occur via an ability to revisit sites of interest. Like types may be identified by a categorization process, which may contain associated spatial information about location via stage and frame coordinates.

Flow-cytometer comprises a time-domain event counter. An embodiment may therefore generate distributions, histograms, or cytograms as provided by a flow cytometer. In addition, an embodiment may access additional spatial-spectral information at a range of length scales and may provide a broader operating range including cases where exogenous labels cannot be used.

Embodiments of a method or system for rendering images or for spectral detection have been described. For example, one or more embodiments may be employed in measuring large populations of cells, intracellular components or other entities. As described previously an embodiment system may digitally render images and categorize them by spectral recognition processes, for example. A sample dispersed as a thin film on a flat substrate may be examined with broadband light optics in an embodiment system. Likewise, pixelized spectra may be generated from a digital camera. As described previously, for an embodiment, category recognition methods may process digitized spectral images through comparison with stored spectra generated offline. Signal cube operations for an embodiment may be enhanced by parallel computation using multiple scalable units. For an embodiment, a host computer or other computing device or computing platform may control sample motion or signal acquisition. Likewise, samples may be measured in an embodiment without use of exogenous tags, or in combination with fluorophores or various enrichment approaches using magnetic particles or quantum dots. Thus, rare cell recognition may become more practical if, for example, larger sample populations may be measured with greater accuracy in a given time compared to flow or laser scanning cytometry.

Method or apparatus embodiments provided may have several advantages, although claimed subject matter is not limited in scope to embodiments have these particular advantages:

1. Advance noninvasive diagnostic methods via peripheral blood tests by detecting rare cells may be possible. Potential applications may include:
    early detection of cancer by recognizing circulating tumor cells.
    prenatal diagnoses via fetal nucleated red blood cells in a mother's blood circulation
    disease monitoring of residual disease and response to cancer therapy
2. Fast and automated spectral-spatial detection and recognition with intracellular sensitivity and resolution may be possible.
3. Expanding areas of cytometry research may take place using fluorescence excitation of exogenous tags by providing a wider array of excitation channels and higher signal acquisition rates.
4. Extending cytometry use to processes and procedures where exogenous tags cannot be used may be possible.
5. Advance cytometry research may be possible by extending capabilities one to two orders of magnitude in speed of signal sample value acquisition. Expanded range of cell population distribution studies may be possible compared to state of the art flow cytometry, laser cytometry and microscopy.
6. Use of visible light radiation and thereby avoiding or reducing destructive interactions with cells or cell components may be possible. Avoiding or reduction of chromatographic damage of cells or loss of genetic material introduced by fluorescent tags or magnetic particles may be possible.
7. Integrated spectral and spatial imaging may be possible from rendered signal sample values more efficiently using unified detection, categorization and recognition methods.

Previously, several possible approaches in which signal processing may be effectively applied to process signals to enhance distinguishing or enhance separation of associated distributions that may be in different categories or classifications, for example, were discussed. For example, discussion was made regarding spectra being classified and components being measured. It is desirable to continue discussing signal processing that may accomplish this or similar goals.

Of course, accurate classification of populations or identification of rare events within large distributions is of interest in a variety fields ranging, for example, from medicine and land remote sensing to materials science. It is not intended that claimed subject matter necessarily be limited in scope to any particular field or application. As is well-known, spectra, signals, signal samples, signal sample values or other similar physical states may exhibit a variety or myriad of stochastic processes. For example, a real-valued N-by-p signal sample value matrix $\underline{\mathbf{x}} = \hat{\mathbf{x}} = [\hat{x}_1, \ldots, \hat{x}_p]$ may provide a processing framework for N signal sample values, measured, for example, over p-dimensions, -channels, or -time intervals. A category of interest may associate random vector components $\hat{x}_j = \hat{I}(\lambda_j)$ with a number of counts or intensity per wavelength or other mass-energy equivalent channel collected in the presence of noise, e.g. from Raman, fluorescence, or light scattering spectra, although, it is intended to be clear that claimed subject matter is specifically not limited in scope to these particular physical phenomena. These are mentioned simply as illustrative examples. Rather, a host of potential physical phenomena may be evaluated in a similar manner, including, for example, frequency, wavelength, phase, energy, mass, wave number, etc. It is intended that claimed subject matter cover a host of different possibilities, including these examples. For example, in some applications, more complex structures involving signal sample values may be included, e.g. spectral images that generate frame arrays where class attributes may be assigned on a per pixel basis to be sorted or aggregated for enhanced analysis, visualization or compression. Nonetheless, to an extent, for any physical phenomenon (or phenomena) that may produce signals, signal samples, signal samples values, or other physical states capable of being measured or counted, such as via a detector or similar device, it is expected that an evaluation of measurements made or counts recorded may benefit from subject matter described herein. Likewise, therefore, it is intended to be included within the scope of claimed subject matter.

As alluded to, previously various dimensional reduction techniques to assist in accurate quantitative classification has been discussed in connection with a variety of embodiments. Proper or effective dimensional reduction approaches have the potential to impact accurate quantitative classification, particularly if, for example, a matrix of signal sample values has N-samples<p-measurement dimensions. Table I shows various possible linear transformations available to decompose signal sample values, such as discussed, for example, in connection with other embodiments, and related methods that might be used to achieve or enhance class separation.

As yet another set of possible approaches or embodiments, use of dimensional reduction in combination with linear discrimination is illustrated as another tool in an arsenal of techniques to affect or enhance quantitative classification. For example, singular value decomposition (SVD) may be an effective technique to apply in some situations, and it is one possible approach mentioned earlier However, in some situations, it may not be sufficient alone to provide a desired score accuracy so that an appropriate level of discrimination for classification purposes, for example, results.

A unique approach for investigation involves a covariance stability condition. This condition is new and unlike stability conditions for feedback control systems. However, for a context involving linear discriminants, for example, matrix inversion may at times be applied. Therefore, a stability condition may be beneficially applied so that computationally matrix inversion is reasonably tractable and may also yield accurate scores.

Analysis of similarity and rotational transforms may be employed, as previously, for example, to evaluate whether further class separation may result. Therefore, possible utility of scale, rotation or non-commutative shear combinations may be evaluated as possible approaches for particular embodiments.

TABLE 1

Sample Matrix Decomposition

| | Linear Transform $\mathbb{R}$ | Rotation $\mathbb{R}$ | Scale $\mathbb{L}$ | Shear $\mathbb{L}\mathbb{R}/\mathbb{R}\mathbb{L}$ | Translation T |
|---|---|---|---|---|---|
| Dimensional reduction | SVD, PCA, Treelet; | Covariance stability, | Discussed infra. | | Common mean variation; |
| Class Separation | PCA | Linear discriminant sections 2, 5 | Discussed infra. | | In-class and common mean variation, |

Computationally, one may consider dimensional reduction as associated with singular value decomposition (SVD) of a matrix of signal sample values, as discussed previously, $\mathbb{X} = \hat{x} = [\hat{x}_1, \ldots, \hat{x}_p]$ and its variation $\mathbb{A} = \overline{\delta x} = [\overline{\delta x}_1, \ldots, \overline{\delta x}_p]$. One may view SVD as functionally or mathematically equivalent to diagonalization, as previously discussed. For example, SVD for a matrix may be expressed as $\mathbb{A} = \mathbb{U}\Sigma\mathbb{V}^T$, where $\mathbb{U}=[u_1,\ldots,u_N]\in\mathbb{R}^{N\times N}$ and $\mathbb{V}=[v_1,\ldots,v_p]\in\mathbb{R}^{p\times p}$ may comprise orthogonal matrices; $u_i$ and $v_i$ may comprise $i^{th}$ left and right singular vectors, and a diagonal N-by-p matrix may be expressed as $\Sigma=\text{diag}(\sigma_1, \ldots, \sigma_m)$ with singular values $\sigma_1 \geq \ldots \geq \sigma_r > \sigma_{r+1} = \ldots \sigma_m = 0$, See GOLUB, G. and Van Loan, C. (1996). *Matrix Computations*. 3$^{rd}$ ed. Johns Hopkins Univ. Press.

An equivalent expression may be employed to decompose a covariance matrix as follows:

$$\mathbb{C} = [C_{jk}] = [<\delta x_j \cdot \delta x_k>] = </\delta x_1 \ldots \delta x_p]^T*/\delta x_1 \ldots \delta x_p>$$

where column vectors are denoted by superscripted transpose, this relationship may be expressed more simply as:

$$\mathbb{C} = \mathbb{W}\Sigma^2\mathbb{W}^T$$

with $\mathbb{W}$ comprising an $\mathcal{m}$-by-$\mathcal{m}$ square orthogonal matrix, its transpose being $\mathbb{W}^T$ and the diagonal matrix of singular values, $\Sigma=\text{diag}(\sigma_1, \ldots \sigma_m)$ from above, is squared.

There are several ways to calculate an average value $<\delta x_j \cdot \delta x_k>$ and claimed subject matter is not limited in scope to a particular approach. As illustrative examples, a $j^{th}$ component variation $\overline{\delta x}_j = \hat{x}_j - <x_j>_{cm}$ may be calculated as a common mean taken over a union of two or more classes and a covariance average may be summed over members of the union. This path may be taken as part of a PCA dimensional reduction approach. A second method may be effective if class separation is a desired objective and typically may be used in pairwise linear discrimination. In this example, a $j^{th}$ component variation $\overline{\delta x}_j = \hat{x}_j - <x_j>_A$ may be calculated for a class and a covariance matrix element average may be comprised of two sums for classes A and B. For convenience, a pooled in-class covariance approach may be used herein, although claimed subject matter is not limited in scope in this respect. Again, many approaches may be employed and claimed subject matter is not intended to be limited to a particular one. Later, a common mean approach is also illustrated.

A SVD space decomposition may be characterized as: Rank(A)+Nullity(A)=max{p,N}, where nullity(A)=nullspace dimension. We note that A may be considered rank deficient if r=rank of $\mathbb{A} = \dim(\text{range}(A)) < \mathcal{m} = \min\{p,N\}$. Theoretical determination of rank deficiency may be complicated, but a tolerance $\delta > 0$ may be employed such that a numerical rank may be determined from a spectrum of principal values contained in $\Sigma = \text{diag}(\sigma_1, \ldots \sigma_m)$ such that $\sigma_1 \geq \ldots, \geq \sigma_r > \delta > \sigma_{r+1} = \ldots \sigma_m = 0$. Machine precision, such as in connection with computing devices, may conventionally affect a lower bound on tolerance $\delta$. Choice of an upper bound may vary with a host of possible factors including, for example, desired dependence on case-specific accuracy.

PCA, and Treelets in general may apply rotational transforms to reveal covariance structure by diagonalization, choice of basis, and spectral analysis. Principal component analysis (PCA) may evaluate values, such as larger signal sample values, in a spectrum with reduction criteria, including sometimes based at least in part on ease of visualization where two or three dimensions are chosen.

However, in at least some instances, class separation may be better achieved by evaluating a signal sample value matrix scale transformation $\mathbb{L}\mathbb{X} = \mathbb{L}\hat{x} = [\lambda_1 \hat{x}_1, \ldots, \lambda_p \hat{x}_p]$. One possible goal in some situations may include retaining as much dimensionality associated with the particular set of signal samples as is feasible, while also yielding the greatest class separation consistent with scaling accuracy and metric criteria.

A reciprocal scale vector $\lambda_{AB} = [\lambda_1 \ldots \lambda_p]_{AB}$ may be sought, to effectively discriminate random vectors $\hat{x}_A = [\hat{x}_1, \ldots, \hat{x}_p]_A$ from $\hat{x}_B = [\hat{x}_1, \ldots, \hat{x}_p]_B$ in terms of their first and second order statistics. A scalar score $S_{AB}$ of $\hat{x}$ generated by a discriminant scale vector $\lambda_{AB}$ may as one example comprise an image of a linear functional $$S_{AB}(\hat{x}) = \lambda_{AB} \cdot \hat{x} = \Sigma_{j=1}^p \lambda_{(AB)j} \hat{x}_j \qquad (1)$$

in which, for this example, $S_{AB}(\hat{x}) \in F$ a real-valued field, random vector $\hat{x} \in V$ a vector space, and dual space $V^* - f(V \rightarrow F)$ comprising an inner product. A difference in mean scores for measurements from two classes A, B may be computed as:

$$D_{AB} = \lambda_{AB} \cdot <\hat{x}_A - \hat{x}_B> = \lambda_{AB} \cdot <d> = S_{AB}(\hat{x}_A) - S_{AB}(\hat{x}_B)$$

and a mean difference per component may be computed as $<d_j> = <x_j>_A - <x_j>_B$. A scale operator $O(\lambda)<x> = [\lambda_1 <\hat{x}_1>, \ldots \lambda_p <\hat{x}_p>]$ may be applied to scale covariance averaged over a pooled set of populations A and B using within-class variations, such as the following:

$$\mathbb{C}_{(\lambda_{AB})} = [C(\lambda_{AB})_{jk}] = [\lambda_j \lambda_k (<\delta x_j \delta x_k>_A + <\delta x_j \delta x_k>_B)].$$

A sum over scaled covariance matrix elements may be computed as $$Q_{AB} = \Sigma_{j,k=1}{}^{p} C(\lambda_{AB})_{jk} = Q_A + Q_B \text{ and}$$

$$Q_X = \Sigma_{j,k=1}{}^{p} \lambda_j \lambda_k \langle \delta x_j \delta x_k \rangle_X \text{ for class } X.$$

In one possible approach, described previously, linear discriminants may be found by employing calculus to maximize a ratio of half of a mean score separation $D_{AB}$ to a within class standard deviation in the following manner, for example:

$$F_{AB} \equiv (D_{AB}/2)/Q_{AB}{}^{1/2} \qquad (2)$$

As described previously, by solving for $\partial F/\partial \lambda_j = 0$ yields $\delta \ln S/\delta\lambda = \partial \ln D^2/\partial \lambda$. So, for one possible approach, a linear discriminant may be derived from a nonlinear relationship using S/D=constant, yielding $[C_{jk}] \cdot \lambda = \langle d \rangle$. Linear discriminants $\lambda_j$ may be found by solving $$\lambda = [C_{jk}]^{-1} \langle d \rangle \qquad (3)$$

an approach previously explained in FISHER, R. (1936). The use of multiple measurements in taxonomic problems. *Annals of Eugenics* 7, 179-188.

However, it may be worth observing that scores may result from a dual space mapping which may be induced by a linear discriminant vector $\lambda$ associated with covariance inverse $[C_{jk}]^{-1}$. For example, a set of relations is described above in Relation (3). SVD may address matrix singularity, which has been shown to be beneficial, of course. However, SVD does not speak at all to whether or not a covariance matrix of signal sample values and its inverse are ill-conditioned. If these matrices are ill-conditioned, a risk exists that resulting scores may not be sufficiently accurate.

In one possible approach, to address the insight discussed above, we may employ, for example, a condition number computed in the following manner:

$$\kappa(\mathbb{C}) \equiv \|\mathbb{C}\| \|\mathbb{C}^{-1}\| \geq \|\mathbb{C}^{-1}\| = 1 \qquad (4)$$

using a matrix norm, which satisfies the sub-multiplicative property $\|AB\| \leq \|A\| \|B\|$. If $\kappa(\mathbb{C})$ is sufficiently large, then c in this context, may be viewed as ill-conditioned.

It is a principle of matrix computation that there is little correlation between size of det $\mathbb{C}$ and a measure of ill-conditioning. Therefore, applying a matrix translation in this context may not produce much beneficial improvement in terms of addressing a risk of being ill-conditioned. Instead, a new covariance stability condition is introduced beyond employing a condition number, for example. As will be seen below, this criterion may be applied in a manner to be norm-independent, if desired, and computationally convenient, both potentially desirable properties. Likewise, the criterion is able to operate as a bound for both a covariance matrix and its inverse, additionally desirable features.

Consider first the identity $\mathbb{C} * \mathbb{C}^{-1} = 1$. Computationally, a product will have on the order of ½ the arithmetic precision of the matrix elements. Rigorous error estimates for inverting matrices of high order and floating point accuracy may be found in Knuth, *The Art of Computing*, (1998) and elsewhere. Although claimed subject matter is not limited in scope in this respect, for purposes solely of illustration, a tolerance of $\epsilon_c \sim 5$ decimal digits, for example, is believed sufficient, for example, using software such as C++ and Boost libraries implementation of uBLAS. This illustrative example assumes a 64 bit computing device of similar platform operating in double precision mode. BLAS is a C++ template class library that provides BLAS level 1, 2, 3 functionality for dense, packed and sparse matrices. Likewise, Gauss-Jordan elimination and SVD use Numerical recipes and MATLAB code, although, of course, these are, again, merely non-limiting examples provided for illustration only. Claimed subject matter is not limited in scope to any particular tolerance with respect to covariance stability; however, typically some tolerance may be desirable in connection with establishing fixed or floating point accuracy in any particular situation.

In at least some embodiments, a covariance stability condition may be computed in the following manner:

$$\det \mathbb{C} * \det \mathbb{C}^{-1} = 1 \pm \epsilon_c \qquad (5)$$

with tolerance $\epsilon_{IEEE} \ll \epsilon_c \ll 1$. For example, in an embodiment, a tolerance $\epsilon_c$ may be set above floating point precision to reduce or even avoid numerical noise from computations on a digital device. Although claimed subject matter is not limited in scope in this respect, as an illustrative example, a lower bound $\epsilon_{IEEE}$ may have 15 decimal digit precision and +−380 base10 exponents set by the IEEE 754-2008 floating point specification for 64 bit binary double precision. As shall be demonstrated, for at least some situations, a stability criterion may be more sensitive than rank deficiency using SVD. For example, a covariance matrix and its inverse may be jointly evaluated, rather than a single matrix, which may result in a lower upper bound on dimension compared to SVD. In situations, therefore, an embodiment employing a stability criterion may provide a more sensitive measure of being near a singularity. Scale factors, therefore, may be found to have desired accuracy.

In cases with multiple training classes, for example, construction of a score vector space may provide benefits such as consolidating available information which may be employed usefully for dimensional analysis, quantitative calibration, or to augment polychotomous classification. Illustrative examples are provided infra.

For K-classes$\{C_j\}$, j=1,K, $({}_2{}^K)$=K(K−1)/2 pairwise combinations may be formed with associated linear discriminant scale vectors $\lambda_{ij}$ with i=1, K−1 and j=i+1, K. For notational convenience, we re-index $\lambda_{ij} = \lambda_n$ with n=1 to $d_K$=K(K−1)/2.

The distance between two score distributions W,Z is given by expanding Relation (2).

$$F_j(W,Z) = [\langle S_j(W) \rangle - \langle S_j(Z) \rangle]/2[\sigma_j(W)^2 + \sigma_j(Z)^2]^{1/2} \qquad (6)$$

where $S_j(W) = (\lambda_j \cdot W)$ and $$\sigma_j(W) \equiv \frac{1}{(n_W - 1)} \sum_{i=1}^{n_W} [\lambda_j \cdot (\delta \hat{W})_i]$$

comprises a scaled standard deviation with $n_W$ the number of samples in W.

An extension of Relation (6) may yield a distance between an unknown sample score $\hat{x}$ and a training distribution $$F_j(\hat{x}, C_k) = (S_j(\hat{x}) - \langle S_j(C_k) \rangle)/2\sigma_j(C_k). \qquad (7)$$

Scale vectors may generate a $d_K$-dimensional score vector $$S(C_j) = (S_1(C_j)/2\sigma_1(C_j), \ldots, S_{d_K}(C_j)/2\sigma_{d_K}(C_j)) \qquad (8)$$

Figure 14:
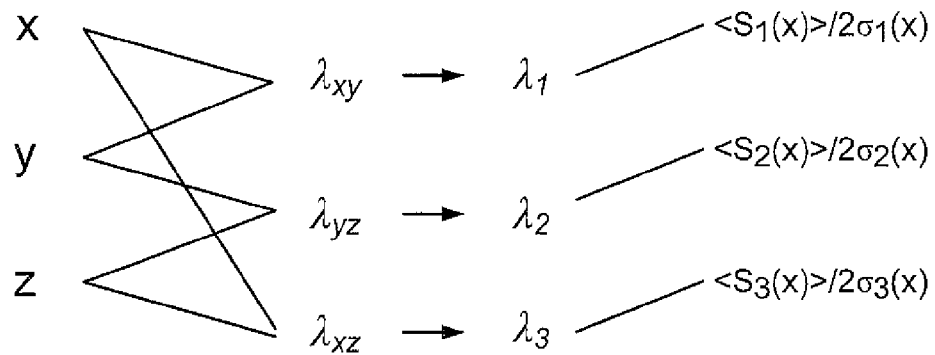
FIG. 14 is a schematic drawing depicting an example embodiment in which three training sets and their associated scale vectors may be used to construct a three-dimensional score space in accordance with claimed subject matter.

Referring to FIG. 14, an example of three training sets x, y, and z generating re-indexed dual space scale maps $\lambda_j$ is provided with score vector components $S_j(x)/2\sigma_j(x)$ for set x. Thus, relations among three training sets x,y,z, and their scale vectors $\lambda_{xy}, \lambda_{yz}, \lambda_{xz}$ used to construct a 3-dimensional score space are shown in FIG. 14.

A norm for a score vector of distribution $C_j$ may be computed as $$\|S(C_j)\|^2 = \Sigma_{i=1}{}^{d_K} [\langle S_i(C_j) \rangle / 2\sigma_i(C_j)]^2. \qquad (9)$$

Thus, an illustrative score vector space, for example, may be comprised of a set of vectors $V^S = \{S(C_j), j=1,k\}$ and an Abelian group $\{V^S, +\}$ over the real number field.

For further illustration, two definitions of addition may be considered. For example, between training distributions one approach might be as follows:

associate an additive inverse with a metric component given by Relation (6) in the following manner, for example $$-\equiv d_i(C_j, C_k) = F_i(C_j, C_k). \tag{10}$$

A distance between set pairs x,z may be characterized in terms of a metric, such as d, which may, for example, if desired, comprise mapping from set pairs to real numbers $d: V^S, V^S \to \mathbb{R}$ that satisfies the following relational properties:

$$d(x,z) \leq d(x,y) + d(y,z) \text{ triangle inequality} \tag{11a}$$

$$d(x,y) = d(y,x) \text{ symmetry} \tag{11b}$$

$$d(x,z) \geq 0 \text{ non-negativity} \tag{11c}$$

$$d(x,y) \leq \epsilon_m \text{ if } fx = y \text{ pseudo-identity}. \tag{11d}$$

Distribution pseudo-equality, so to speak, may be determined in accordance with a metric resolution $\epsilon_m$ in combination with Relations (6), (10), and (11d) where if $\epsilon_m \approx 1$ then $$<S(x) - S(y)> \leq 2[\sigma(x)^2 + \sigma(y)^2]^{1/2} \tag{12}$$

may comprise a relation to be applied to determine equality of score distributions S(x) and S(y).

Of course, claimed subject matter is not limited in scope to a metric such as described immediately above or to any other particular metric. Various metrics may be defined. An illustrative metric, as an example, generated instead from, for example:

Relations (9) and (10), in which distance between two classes $C_j$ and $C_k$ may be computed as $$d(C_j, C_k)^2 = \|d_i(C_j, C_k)\|^2 = \|S_i(C_j) - S_i(C_k)\|^2 = \Sigma_{i=1}^{dK} F_i(C_j, C_k)^2 \tag{13}$$

and distance from an unknown sample $\hat{x}$ to a training class $C_k$ may be computed as $$d(\hat{x}, C_k)^2 = \|S(\hat{x}) - S(C_k)\|^2 = \Sigma_{i=1}^{dK} [(S_i(\hat{x}) - <S_i(C_k)>)/2\sigma_i(C_k)]^2. \tag{14}$$

A higher level algebraic comparison may be possible, and desirable, if an inner product may be associated with a metric and a normed vector space. It has been shown that if, in a normed space, a parallelogram relation holds, then there is an inner product. See, for example, Blanchard and Brüning *Mathematical Methods in Physics*. (2003) A parallelogram relation may be characterized as:

$$\|S(C_j) + S(C_k)\|^2 + \|S(C_j) - S(C_k)\|^2 = 2\|S(C_j)\|^2 + 2\|S(C_k)\|^2 \tag{15}$$

Not every norm satisfies Relation (15), including the metric associated with Relation(13), as an example. While it appears that a normed score space $V^S = \{V, +\}$ cannot be extended to an algebra having an inner product, this is not meant to necessarily imply that it would not provide a suitable metric space. Suitability of a metric space may depend at least in part on a host of issues or factors, usually particular to the application at hand.

As yet another illustrative example, another candidate metric may be characterized for a score vector space $\{V, \oplus\}$ where the additive inverse may be computed as $$-\oplus \equiv d_i^*(C_j, C_k) = <S_i(C_j)>/2\sigma_i(C_j) - <S_i(C_k)>/2\sigma_i(C_k). \tag{16}$$

Relation 16 may be compared with Relation (10) to illustrate a second type of addition. A norm associated with Relation (16) may be shown to satisfy relation (15). A normed distance between vectors may be computed as follows:

$$d^*(C_j, C_k)^2 = \|S(C_j) - \oplus S(C_k)\|^2 = \Sigma_{i=1}^{dK} d_i^*(C_j, C_k)^2 \tag{17}$$

It may be convenient to apply a metric condition, such as from Relation (17), with a pairwise comparison of vectors and an equivalent version of Relation (11a), which may be referred to as an inverse triangle inequality and determined as follows:

$$\|\|S(C_j)\| - \oplus \|S(C_k)\|\| \leq \|S(C_j) - \oplus S(C_k)\|, \tag{18}$$

Relation (16) may be employed to produce an inner product using, for example, the polarization identity $$S(x) \cdot S(y) = \frac{1}{4}(\|S(x) \oplus S(y)\|^2 - \|S(x) - \bigoplus S(y)\|^2).$$

Combining Relations (16) and (19) therefore provides an inner product relation (20) as follows:

$$S(x) \cdot S(y) = \Sigma_{i=1}^{dK} <S_i(x)><S_i(xy)>/4\sigma_i(x)\sigma_i(y). \tag{20}$$

Figure 15:
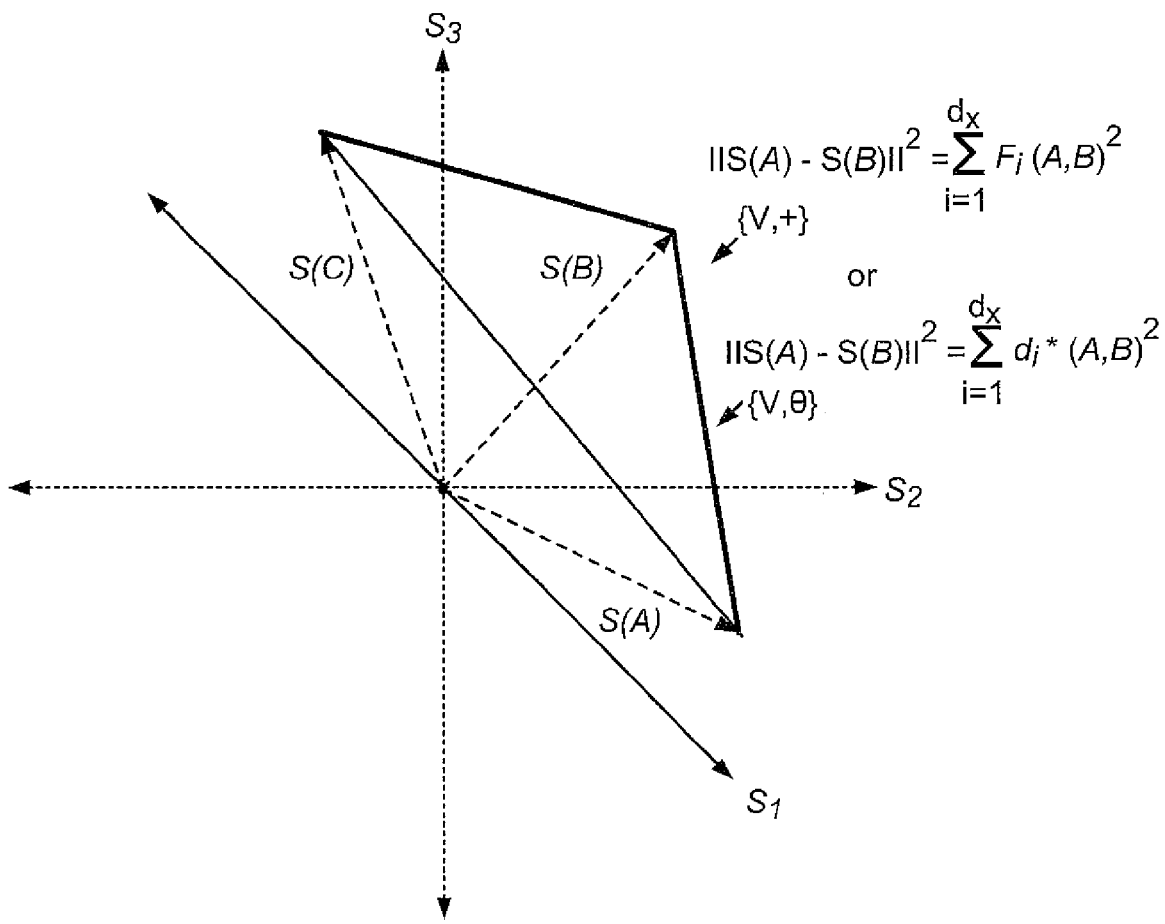
FIG. 15 is a sample plot demonstrating two example score vector spaces having different properties.

FIG. 15 depicts relationships discussed in some above examples, which are summarized as follows. Two versions of a normed score vector space $S(x) \in V_S$ were illustrated. The two spaces $\{V, +\}$ and $\{V, \oplus\}$ respectively have their Abelian group addition respectively characterized by $d_i$ Relation (10) and $d_i^*$ by Relation (16). In both cases, although the same norm of a vector is employed $\|S(x)\|$; still, the distance between vectors is different: Relation (13) for $\{V, +\}$ and Relation (17) for $\{V, \oplus\}$.

As suggested previously, useful properties of metrics may vary so that different metrics might be preferred in different situations since different issues may likely be addressed. While in theory at least, the space $\{V, \oplus\}$ generates an inner product that provides an algebraic structure it does not appear to have a an easily constructed extension for comparing unknown samples to distributions. In contrast, demonstrated previously, space $\{V, +\}$ allows comparison of an unknown sample to a distribution since the norm given by Relation (14) is similar in some respects to Relation (13).

Although claimed subject matter is not limited in scope in this respect, in some contexts, as indicated previously, preserving as much dimensionality for a set of signal samples as may be feasible is potentially desirable at times. Metrics may be handy at times by providing desirable properties IL for example, one may be comparing scores. A potential disadvantage, however, of employing metrics may be that metrics computationally may tend to reduce available dimensionality for a set of signal samples, especially metrics that may be quite complex. Therefore, as shown in more detail below, space $\{V, +\}$, in addition to allowing comparison of an unknown sample to a distribution, may reduce dimensionality to a lesser extent than some alternatives.

Application of rotational transforms to a signal sample value matrix, before or after scaling, has been considered as another strategy to seek increased class separation. By applying rotation operators to a common-mean (SVD and PCA) or class-centered (Fisher scaling) matrix; in effect, an improved structure is sought in a real symmetric covariance matrix representing a vector space containing the signal sample values which may be transformed. One may view SVD as generating a spectrum $\lambda(A)$ of numbers, which reveal this structure. Likewise, one may view principal components employed in PCA as an ordered set of covariance eigenvalues $\{\sigma_y^2\}$ and eigenvectors. There are well-known differences in the matrix factorization by eigen-decomposition compared to SVD. However, these differences disappear if a square, symmetric covariance matrix is used. See PRESS, W., TEUKOLSKY, S., VETTERLING, S., and FLANNERY, B. (2004 Section 11.0.6, pp 569-570, *Numerical Recipes: The Art of Scientific Computing*. 3$^{rd}$ ed. Cambridge Univ. Press.

For a general polynomial for degree m≥5 there is no known algebraic solution for the characteristic polynomial. Therefore, computing eigen-values of a general m$^{th}$ order matrix typically comprises an iterative process. For example, a Jacobi sequence comprises a classic iterative process for deriving eigen-values by progressive diagonalization of a covariance matrix via a sequence of orthogonal similarity transformations.

$$\mathbb{C}^{(1)} = \mathbb{J}_{pq}^T \mathbb{C}^{(0)} \mathbb{J}_{pq} = \mathbb{J}_{pq}^T \cdot \delta x^{(a)^T} \cdot \delta x^{(a)} \cdot \mathbb{J}_{pq} = \delta x^{(1)^T} \cdot \delta x$$

Pairwise $x_p, x_q$ variable transformations via Jacobi rotations are in general intended to reduce or eliminate corresponding off-diagonal covariance matrix elements $C_{pq} = \langle \delta x_p \cdot \delta x_q \rangle$. A superscripted $x_j^{(l)}$ will represent the l$^{th}$ transformation.

A Jacobi rotation matrix $$\mathbb{J}_{pq} = \begin{matrix} 1 & & & & & 0 & & 0 \\ & 1 & & & & 0 & & 0 \\ & & \begin{bmatrix} c & \cdots & s \\ \vdots & 1 & \vdots \\ -s & \cdots & c \end{bmatrix} & & & 0 & & 0 \\ & & & & & 0 & & 0 \\ & & & & & 0 & & 1 \\ & & & & & 0 & & 1 \end{matrix}$$

with $c = \cos \phi_{pq}$ and $s = \sin \phi_{pq}$ appearing in the p$^{th}$ and q$^{th}$ rows and columns and whose argument $$\phi_{pq} + k\pi = \frac{1}{2} \tan^{-1} \frac{2 C_{pq}}{(C_{qq} - C_{pp})}$$

may be derived from covariance matrix elements. Conventionally, k=0, which restricts $-\pi/4 \leq \phi_{pq} \leq \pi/4$. Components of a covariance matrix may be computed as:

$$C^{(1)}_{rp} = c \cdot C^{(0)}_{rp} - s \cdot C^{(0)}_{rq}$$

$$C^{(1)}_{rq} = c \cdot C^{(0)}_{rq} + s \cdot C^{(0)}_{rp}$$

The above holds for r≠p, r≠q, otherwise $$C^{(1)}_{pp} = c^2 \cdot C^{(0)}_{pp} + s^2 \cdot C^{(0)}_{qq} - 2 \cdot s \cdot c \cdot C^{(0)}_{pq}$$

$$C^{(1)}_{qq} = s^2 \cdot C^{(0)}_{pp} + c^2 \cdot C^{(0)}_{qq} + 2 \cdot s \cdot c \cdot C^{(0)}_{pq}$$

$$C^{(1)}_{qq} = (c^2 - s^2) C^{(0)}_{pq} + sc(C^{(0)}_{pp} - C^{(0)}_{qq})$$

Other matrix elements remain unchanged.

A transformation may be explicitly seen as a rotation in the $x_p, x_q$ plane and as a change of basis by writing out $$\delta x^{(0)} \cdot \mathbb{J}_{pq} = [\delta x_1; \ldots; \delta x_{p-1}; (c \cdot \delta x_p - s \cdot \delta x_q); \delta x_{p+1}; \ldots$$
$$\delta x_{q-1}; (s \cdot \delta x_p + c \cdot \delta x_q); \delta x_{q+1}; \ldots \delta x_n] = \delta x^{(0)} \cdot \mathbb{R}_0.$$
$$\mathbb{J}_{pq} = \delta x^{(0)} \cdot \mathbb{R}_1 = \delta x^{(1)}$$

$\mathbb{B}_0$ is the identity matrix, $\mathbb{B}_{l-1} \cdot \mathbb{J}_{k(l)j(l)} = \mathbb{B}_l$ is a change of basis with new coordinates $\delta x^{(1)}$. A subsequent iteration is intended to produce a new basis vector with a new pair of axes k(l),j(l) chosen from the correlation coefficient $$C^{(l)} = \mathbb{J}^T C^{(l-1)} \mathbb{J} = \mathbb{J}^T \cdot \delta x^{(l-1)^T} \cdot \delta x^{(l-1)} \cdot \mathbb{J}.$$

Faster strategies for finding eigen-pairs of real symmetric matrices may reduce a matrix to some simpler form before applying iterations.

A finite operation method for diagonalizing a covariance matrix should introduce some additional error; yet such an approach has improved upon PCA feature selection in some cases by using Treelets. Treelet and PCA methods both involve similarity transformations but differ in how space reduction occurs.

A Treelet approach uses similarity transformations operating on a covariance matrix as a Jacobi sequence. Order of transformation is also determined by respective correlation coefficients in a Treelet approach. Highly correlated elements are handled first. For example, the largest off diagonal covariance element $C_{ij}$ is selected, which is related to the smallest distance $d_{ij} = (1 - r_{ij})/2$. A Treelet process terminates after d-1 rotations, where d is the dimension. A procedure of terminating a Jacobi sequence after d-1 rotations therefore may be used to simplify computations, as is illustrated infra. Residual errors from finite terminations appear to be negligible.

A Treelet process derives its name from a hierarchical method of axes transformation in which successive cross correlations among samples are reduced. A training signal is represented as an expansion of basis functions $\delta x^{(0)} = \Sigma_j s_j^{(0)} \phi_j^{(0)}$ with $\{\phi_j^{(0)}\}$ initialized as columns of an identity matrix $B_0 = 1$. As correlated signal sample values have a Jacobi rotation applied respective off diagonal elements become zeroed out; two on-diagonal elements are represented as a sum and difference variable:

$$x^{(l)} = \Sigma_{j=1}^{p-1} s_j^{(l)} \phi_j^{(l)} + \Sigma_{j=1}^{l} d_j^{(l)} \psi_j^{(l)}.$$

A pair wise transformation of the basis set results with scale and wavelet coefficients. Unlike Jacobi's method, for a Treelet approach difference variables are stored whereas sum variables are processed. A similarity (or correlation) matrix is calculated using new coordinates and $s_j^{(l)}$ but not residual noise terms $d_j^{(l)}$. These reduce off diagonal elements of the correlation matrix and may result in a sparse basis set. This latter representation offers another method to reduce dimensionality and is analogous to lossy compression.

However, various use cases, discussed later, suggest class discrimination may be more effectively achieved by preserving dimensionality, using information generated by scale vectors. These examples therefore suggest, as discussed later, that rotational transformations may provide little performance benefit in this context.

A related, but separate, issue is handling of an unknown sample to categorize it after training sets have been scaled, scored and measured. We note this in the context of an embodiment of an overall system, as has been described. However, it is likewise noted that this aspect may also be handled independent of the previous discussion related to separation of distributions since, as noted previously, a desire to separate distributions in a set of signal sample values may arise in a host of different contexts apart from an overall system embodiment with respect to spectral recognition. Nonetheless, within a context of an overall system embodiment, for example, a second phase of classification may uses a decision rule to assign samples to outcome states. For polychotomous classification, an additional challenge may include assigning a class label or a joint conditional probability for an outcome based at least in part on K(K-1)/2 pairwise potential decisions.

In one approach, a collection of rules may be employed to implement a decision logic structure, which may also have a benefit of assisting in setting classification error bounds. Possible error sources may be potentially identified from lack of training set discrimination or insufficient specification of pairwise or joint output states, for example. Sensitivity or specificity of a classification policy may be otherwise determined at least in part by subsequent examination or other model evaluation of training or unknown sample distributions. As unknown sample classification errors may be detected, these may be reclassified as part of an iterative training process which may result in overall improvement of a classification process.

Decision rules using conditional probability estimates to assign a class label and provide joint probability estimates based at least in part on pairwise coupling have been studied and developed. See, for example, FRIEDMAN, J. H. (1996). Another Approach to Polychotomous Classification. *Stanford Technical Report*; HASTIE, T. and TIBSHIRANI, R. (1998). Classification by Pairwise Coupling. *Annals of Statistics*, Vol. 26, no. 2, 451-471; and WU, T.-F., LIN, J.-C., WENG, R. (2004). Probability estimates for multi-class classification by pairwise coupling. *J. Machine Learning Research* 5, 975-1005. Although an embodiment may employ conditional probably distributions, in an alternative embodiment, assignment may be based at least in part on score space partitioning rather than conditional probabilities, as discussed below for an illustrative example. Polychotomous classification may in some embodiments result from joint pairwise decisions determined by voting or by using norms of score vectors, which may be associated with a d-dimensional joint distribution. To simplify notation, a set A may be represented by the "cover of the domain of its score set," e.g., A may, for example, characterized as the interval A=[score min, score max].

Given two training sets A and B, a decision rule of course potentially affects error estimation, which may depend, for example, at least in part on the number of possible output states to which unknown samples may be assigned. If A and B intersect, so that $A \cap B \neq \{\emptyset\}$ in general an upper bound would be expected to exist on classifier accuracy. Estimates for a possible embodiment may be calculated using Bayes rule with error expressed in terms of conditional probabilities assuming equal a priori probabilities. See HUGHES, G. (1968). On the Mean Accuracy of Statistical Pattern Recognizers. *IEEE Trans. Information Theory*, vol. IT-14, No. 1, January. pp. 55-63. Alternate embodiments may employ a likelihood ratio and different thresholds with cost functions or Neyman-Pearson tests to emphasize relative importance of type I (false positive) or type II (false negative) errors, for example. These are meant to be illustrative possibilities only. A host of approaches are possible and claimed subject matter is not intended to be limited in scope to a particular approach or technique.

In an embodiment in which a binary decision classifier may be used unknown samples may be assigned one of two possible outcomes A and B. If an unknown sample score $S_{AB}(x) = \lambda_{AB} \cdot \langle x \rangle$ were to have a value so as to not be clearly indicative of A or B, a classification rule may in one embodiment be applied to determine to which set it belongs. An example membership policy as an illustrative example may include the following. In the case of disjoint sets $A \cap B = \{\emptyset\}$ and assuming $\langle X \rangle_A \ll \langle X \rangle_B$ then let $X \in A$ if $(X < \max X_A)$ $X \in B$ if $(X > \min X_B)$ else $X \in A$ if $(X - \max X_A) < (\min X_B - X)$, otherwise $X \in B$. And if $A \cap B \neq \{\emptyset\}$, define $p_A(X) = [(\langle X_A \rangle | \sigma_A) X] / [(\langle X_A \rangle + \sigma_A) - (\langle X_B \rangle - \sigma_B)]$ Then $X \in A$ if $p_A(X) \geq p_B(X)$ and $p_A(X) + p_B(X) = 1$, else $X \in B$.

While adept choice of binary decision classifier(s), membership policy(ies), and threshold(s) may vary sensitivity or specificity, errors remain possible even if sets are disjoint, as an example. One should expect ranges of score space available that do not clearly indicate assignment to one category or another despite efforts to avoid such a situation. Another issue to consider in an embodiment that also may arise includes a sample being contaminated with an unknown entity while one expects there to be two assigned classes (rather than three). A score may result outside a range determined by a training process, for example. In an embodiment, an approach to address such an unexpected possibility, a set of possible outcomes may be extended to include another member $O = \overline{AB}$ where $\overline{A}$ is the complement of A, $A \cup \overline{A} = \mathbb{R}$ may comprise the space of all possible events, e.g., the real-valued score range. If an unknown sample score $S_{AB}(x)$ lies outside a score indicative of A or B then it may be assigned to class O. See FIG. 16, for example, in which an illustrative examples of a manner in which a score space may be partitioned by training sets A, B, and O=(not A and not B) is shown, assuming case $A \cap B = \{\emptyset\}$, in this example. To capture and potentially reduce intrinsic training score errors four outcomes $A_O = A \cap \overline{B}$, $B_O = \overline{A} \cap B$, $A \cap B$, and O are used. However, a nonzero intrinsic error may be associated with a score interval $A \cap B$, rather than with score intervals for O, for example, in an embodiment.

Classification of unknown samples if there are $K \geq 3$ classes may become more complex and may involve construction of joint distributions. Two approaches for construction of joint distributions will be described, although these are merely illustrative and claimed subject matter is not limited in scope to these approaches. Again, a host of possible approaches to perform construction of joint distributions are possible and claimed subject matter is not intended to be limited to a particular approach.

One method for polychotomous classification in an embodiment may involve use of a combination rule based at least in part on the number of pair-wise wins. See Friedman, J. H. (1996). Another Approach to Polychotomous Classification. *Stanford Technical Report*. That work has been extended to combine pairwise probability estimates into a joint probability for all K-classes. See HASTIE, T. and TIBSHIRANI, R. (1998). Classification by Pairwise Coupling. *Annals of Statistics*. Vol. 26, no. 2, 451-471. Other pairwise coupling approaches have been described. See WU, T.-F., LIN, J.-C., WENG, R. (2004). Probability estimates for multi-class classification by pairwise coupling. *J. Machine Learning Research* 5, 975-1005.

Figures 16, 17, 18:
FIG. 16 is a schematic diagram illustrating one example embodiment of partitioning a score space by training sets.
FIG. 17 is a table showing an example embodiment of an approach to handling joint outcomes from applying pair-wise "wins."
FIG. 18 is a table showing another example embodiment, more complex than the embodiment of FIG. 17, of an approach to handling joint outcomes.

A second method that may be employed in an embodiment may associate a joint distribution with a $d_K$-dimensional norm, such as, for example, described previously. Elements of an example are illustrated for K=3 and may be extended inductively to describe a more general case. FIG. 17 illustrates joint outcomes applying pair-wise wins. It is noted that $T = A \cap B \cap C$ is a tie. There are $N_p = 3$ pairs of discriminant vectors for K=3 training classes A, B, C. If a binary decision is to be assigned to either A or B then there are four possible outcomes A, B, C, and T to which an unknown sample may be assigned, as shown in FIG. 17. A tie state T may be a result of a voting rule where joint outcomes reflect at least in part number of wins, e.g., number of pairwise assignments of a binary decision classifier. Number of possible states may be computed as $N_B = (Z)^{K(K-1)/2}$ where number of possible pairwise outcomes Z={2 or 3} depending at least in part, for example, on whether one chooses to include the O=other option. In this example; $N_s = 2^3 = 8$. For this illustrative example, a joint outcome state space is partitioned into equal probabilities $\frac{1}{4}$=P(A)=P(B)=P(T), although claimed subject matter is of course not so limited.

If three outcomes (X, Y, O=$\overline{XY}$) are allowed for a X, Y scale vector $\lambda_{XY}$ then $N_S=3^3=27$ and FIG. 18 results. FIG. 18 shows a state space if three outcomes are allowed for a scale vector pair. In this example, there are four joint outcome states A,B,C,T,O. In this example, state O wins all ties. AB output A$\Rightarrow\overline{C}$ and AC output C$\Rightarrow\overline{A}$ and BC output O$\Rightarrow\overline{BC}$. Therefore a joint outcome is $\overline{CAB}$=O. Applying these results to this example, a joint outcome state space now yields P(A)=P(B)=P(C)=3/27; P(T)=2/27; P(O)=16/27.

For an embodiment, as K increases; rules on handling ties may be expected to increase, e.g. if K=4 there are 6 pairwise classifiers, which leads to outcomes where 2 of the 4 pairwise output states, e.g. A and C of A,B,C,D occur twice. A new tie state $T_1$=A∩C may be employed to account for this in an embodiment. Complexity may also occur in the number of possible output states, e.g. if K=256, then there are 32,640 pair classifiers and 1.4E122 possible states for 3 allowed pairwise outcomes.

One possible approach in an embodiment to address growing complexity may be to reduce a polychotomous problem to a dichotomous case by using a "1 against many" approach. A similar notion had been alluded to previously. For example, a training set A may be compared with a union of others B∪C∪ .... In some cases, this may be a more tractable approach, but may suffer from two possible aspects. One may be that individual pairwise scale factors may not be used. A second may be that use of a common mean or other joint classification of unions may lead to lower separation of classes.

Another approach in an embodiment may be to construct a joint distribution from a [K(K−1)/2]-dimensional score space with normed metric, as discussed previously. A benefit includes use of available training information from pair wise scaling; likewise, a score vector may be yielded for an unknown sample, which may be compared to its proximity to K training classes thereby enabling a possible decision as to its assigned output state.

For example, in an embodiment, joint outcome assignment criteria may be based at least in part on ordering distances of a random sample vector $\hat{x}$ to training sets $\{C_k\}$ using Relation (14)

$$\|x-C_j\|\leq\|x-C_w\|\leq \ldots \leq\|x-C_z\|. \quad (21)$$

Then assign $\hat{x}$ to $C_j$. A tighter bound on membership may be used in an embodiment, if desired, by replacing training class standard deviations with the cover of their support, a previously introduced concept.

Three separate cases of Raman spectra are now examined as illustrative embodiments in accordance with claimed subject matter. However, it is intended to be clear that claimed subject matter is not intended to be limited to these illustrative examples. These example embodiments are provided solely for purposes of illustration and are not intended to limit the scope of claimed subject matter in any way. As one simple example, and has been made clear previously, claimed subject matter is not limited to Raman spectra.

In an embodiment, one may consider that p-measurement channels characterize an initial dimension of a matrix of signal sample values. SVD yields dim(range(A))≤m=min{p,N}=N as p>N in these example cases. In these examples, a procedure is applied to select and sort the top N (wavenumber, intensity) pairs using measured intensity. In this procedure, dimensionality may be reduced until a covariance stability condition, as described above, is found to exist. Score distributions for various classes or samples may be calculated from linear discriminants after stability has been found to occur. A statistically normalized score difference approach may be used as a measure to investigate particular aspects of these example cases.

A first example comprises five component Raman spectra. This case study evaluates measure resolution, protein score calibration, and signal to noise. Sample Raman spectra were synthesized by a sum of five known components: carbohydrate, DNA, lipid, "other", and protein, see FIG. 19. The "other" category sampled an intracellular region not associated with the other four components of known composition. See Uzunbajakava, N., Lenferink, A., Kraan, Y., Willekens, B., Vrensen, G., Greve, J. and Otto, C. (2004 Nonresonant Raman imaging of protein distribution in single human cells, *Biopolymers* 72 1, 1-9. Individual component spectra were obtained from separate experimental measurements. Sample spectrum were normalized to $1\times10^6$ counts, to address potential apparatus-specific bias. Average integrated component Raman intensities are shown in Table 2 below.

Figure 19:
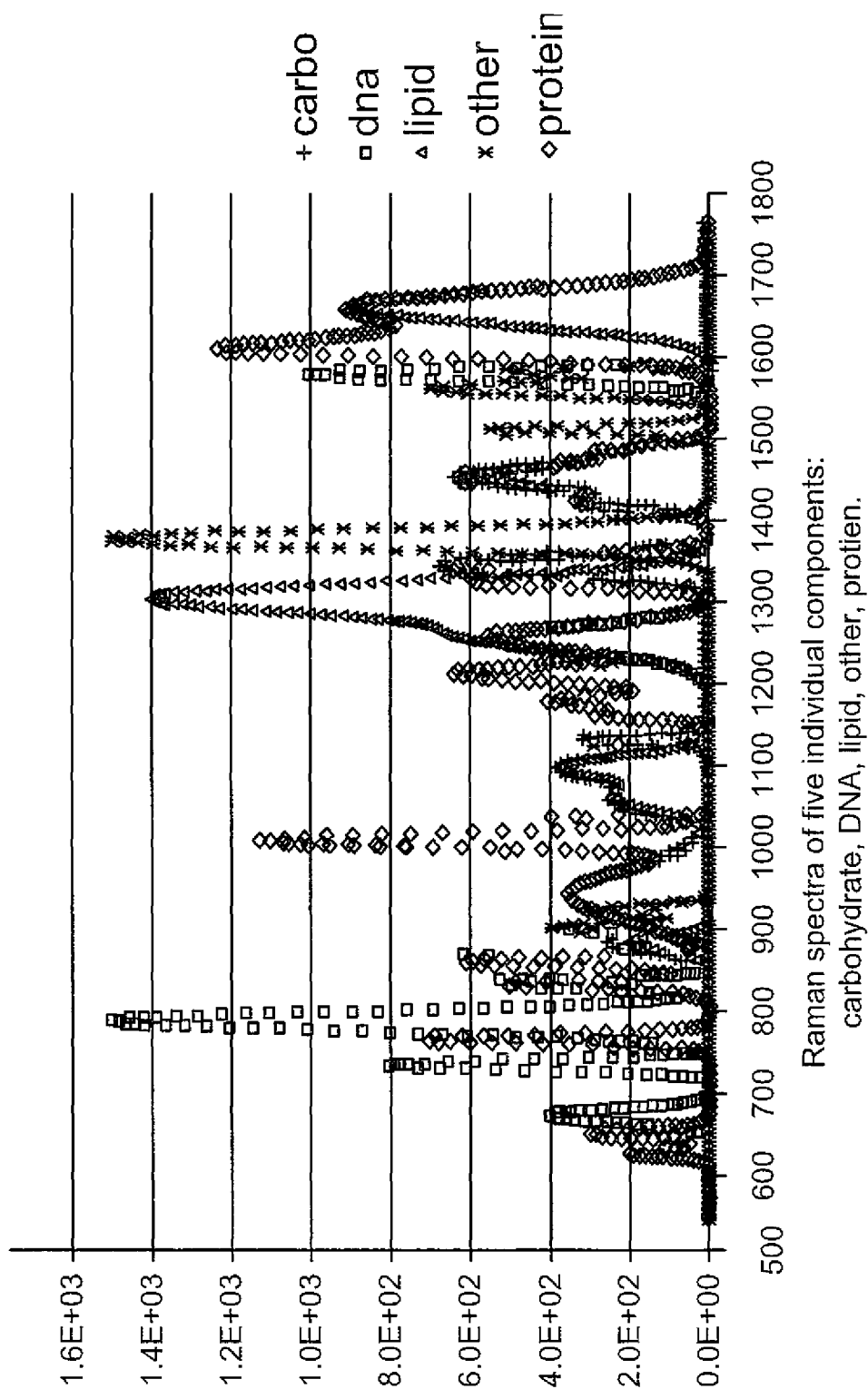
FIG. 19 is a sample plot illustrating an example of a five component Raman spectra.

In FIG. 19, for example, intensity of a component per channel is varied with a normal distribution to simulate chemical noise. For calibrating scores to protein concentration, a ratio of standard deviation to mean value was set at $\sigma_{Normal}/<I(\lambda_j)>=10\%$. Subsequent noise sensitivity estimates vary the ratio up to 50%. Poisson noise was independently added to a channel to simulate extraneous measurement effects. Thus, total variance per channel $\lambda_j$ is the sum of zero-mean Gaussian and Poisson contributions $$\sigma_{Tot}^2=<I(\lambda_j)>+\sigma_{Normal}^2. \quad (22)$$

TABLE 2

Five components of Raman spectra with protein concentration varied from the baseline.

|  | Baseline | | 1.1x Protein | | 1.25x Protein | | 2.0x Protein | |
| --- | --- | --- | --- | --- | --- | --- | --- | --- |
|  | Counts | % | Counts | % | Counts | % | Counts | % |
| carbo | 1.25E+05 | 12% | 1.2E+05 | 12% | 1.2E+05 | 12% | 9.4E+04 | 9% |
| dna | 2.26E+05 | 23% | 2.2E+05 | 22% | 2.1E+05 | 21% | 1.7E+05 | 17% |
| lipid | 2.29E+05 | 23% | 2.2E+05 | 22% | 2.1E+05 | 21% | 1.7E+05 | 17% |
| other | 9.65E+04 | 10% | 9.3E+04 | 9% | 8.9E+04 | 9% | 7.3E+04 | 7% |
| protein | 3.25E+05 | 32% | 3.5E+05 | 35% | 3.8E+05 | 38% | 4.9E+05 | 49% |
| Total | 1.0E+06 | 100% | 1.0E+06 | 100% | 1.0E+06 | 100% | 1.0E+06 | 100% |

TABLE 2-continued

Five components of Raman spectra with protein concentration varied from the baseline.

| | Baseline | | 1.1x Protein | | 1.25x Protein | | 2.0x Protein | |
|---|---|---|---|---|---|---|---|---|
| | Counts | % | Counts | % | Counts | % | Counts | % |
| carbo | 1.25E+05 | 12% | 1.2E+05 | 12% | 1.2E+05 | 12% | 9.4E+04 | 9% |
| dna | 2.26E+05 | 23% | 2.2E+05 | 22% | 2.1E+05 | 21% | 1.7E+05 | 17% |
| lipid | 2.29E+05 | 23% | 2.2E+05 | 22% | 2.1E+05 | 21% | 1.7E+05 | 17% |
| other | 9.65E+04 | 10% | 9.3E+04 | 9% | 8.9E+04 | 9% | 7.3E+04 | 7% |
| protein | 3.25E+05 | 32% | 3.5E+05 | 35% | 3.8E+05 | 38% | 4.9E+05 | 49% |
| Total | 1.0E+06 | 100% | 1.0E+06 | 100% | 1.0E+06 | 100% | 1.0E+06 | 100% |

Figure 20:
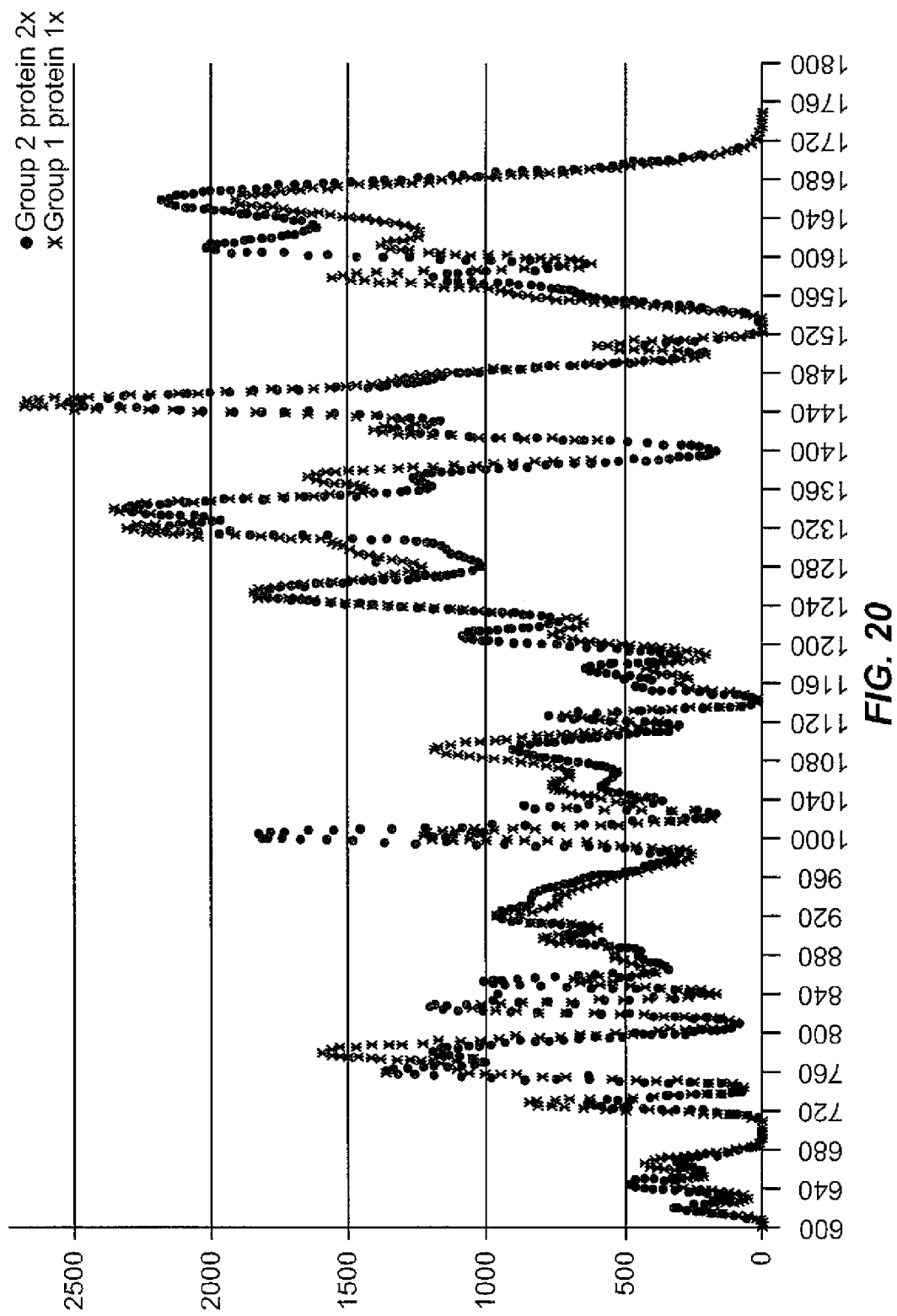
FIG. 20 is a sample plot illustrating an example of intensity-averaged Raman spectra for two groups of signal samples.

The two groups of intensity-averaged Raman spectra have p=1340 measurement channels, see FIG. 20. In FIG. 20, two groups of intensity-averaged Raman spectra derived from the Table 2 components are shown. Group 1 has 32% protein/total concentration and Group 2 has 49%. Group 2 has 2× relative protein concentration of Group 1 baseline. The example uses N=30 samples.

Figure 21:
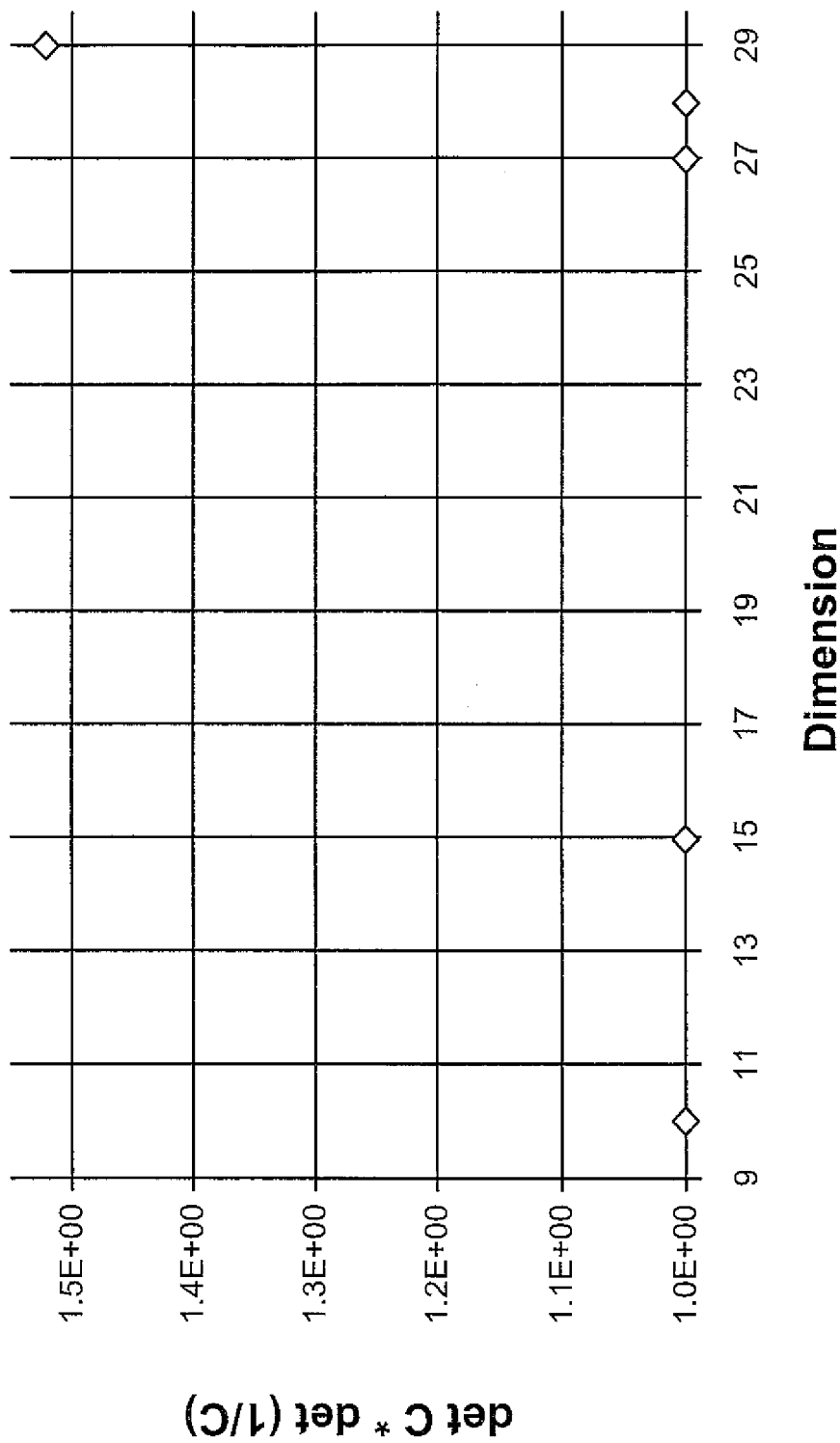
FIG. 21 is a sample plot illustrating an example of an embodiment in which covariance stability may be evaluated for a set of signal samples.

Referring to FIG. 21, a nonzero minimum singular component exists at d=30, so there is no further rank reduction. The top N peaks are selected by a rank and sort procedure, as mentioned. Using the Group 1 baseline set partition the bound on stable dimension is d≤28. Thus, FIG. 21 illustrates covariance stability of a Group 1 set partition {g1A, g2A}, which are members of the same class of five component Raman spectra having 10% Gaussian noise. The total sample number N=30. For d≤28; det $\mathbb{C}$ *det $\mathbb{C}^{-1}$<1±1×10$^{-4}$ is within a specified tolerance.

Measurement resolution may be estimated by finding a distance between two subsets selected in a single group partition. A calibration set {g1A,g1B} may be composed of N=44 samples of a baseline Group 1. A set is split into two subsets g1A and g1B, having 22 samples evenly. Subset sample scores $X_A=\lambda_{AB} \cdot X_A$ and $X_B=\lambda_{AB} \cdot X_B$ were generated by their mutual scale vector. Sample errors for this self calibration method are 10% of F(A,B), which might be refined further with a bootstrap estimate.

Figure 22:
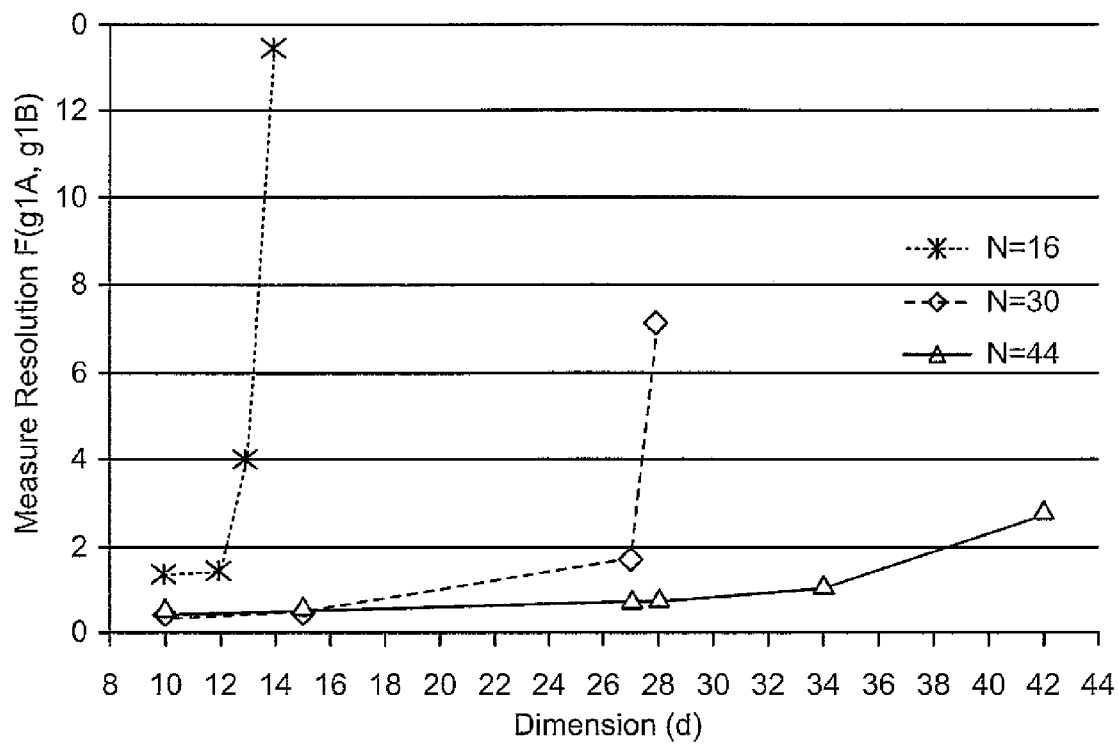
FIG. 22 is a sample plot of measured resolution graphed as a function of distance for sets of signal samples.

A resolution measure may be given by a score separation distance $F_{AB}$ (g1A, g1B; d, N). This is graphed as a function of dimension (see FIG. 22) and sample size (see FIG. 23). FIG. 22 shows score distance measure resolution. Group 1 Raman spectra are partitioned into subsets A and B with 10% Gaussian chemical noise, respectively. N=total sample size of A+B. For a given N, a monotonic increasing function may have a maximum dimension determined at least in part by a covariance stability condition. A growing separation between two sets of "equivalent" members as dimension increases is a manifestation of the so-called "curse of dimensionality", or equivalently a deteriorating contrast in the chosen primary distance metric. See HOULE, M., Kriegel H., Kroger P., Schubert E., Zimek A. (2010). Can Shared-Neighbor Distances Detect the Curse of Dimensionality? *Lecture Notes in Computer Science* 2101, vol. 6187/2010, pp 482-500.

Figure 23:
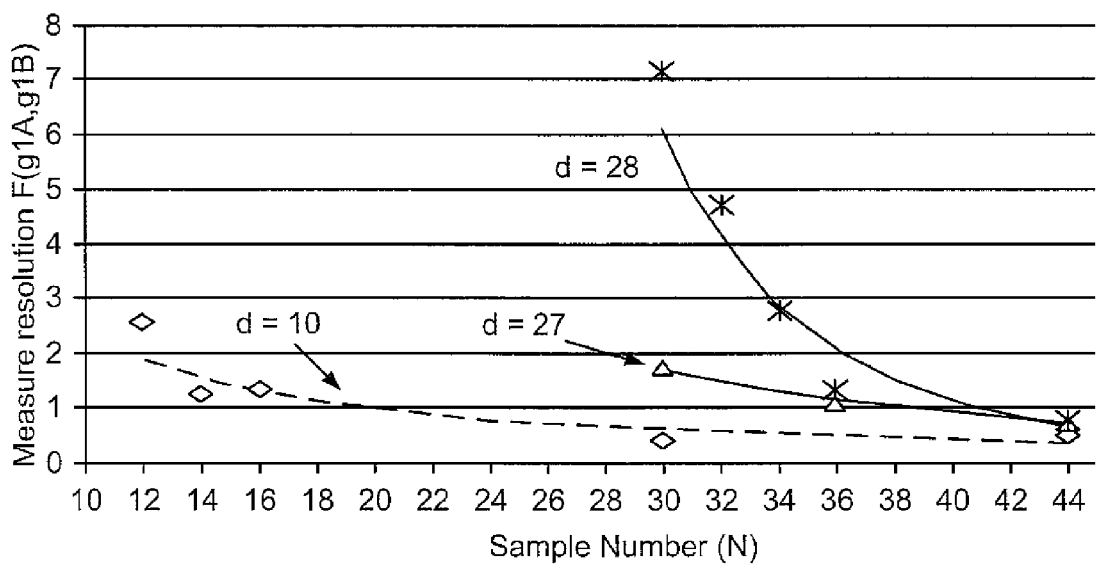
FIG. 23 is a sample plot of measured resolution graphed as a function of sample size for sets of signal samples.

FIG. 23 provides another view of $F_{AB}$(g1A, g1B; d, N). Increased sample size N yields higher measure resolution at a fixed dimension, e.g., class score separation F(g1A, g1B) is reduced. Onset of instability and loss of resolution appears to occur as dimension increases from 27 to 28 for N=30. See also FIG. 22.

For a given dimension and sample size, score separation influences class identity resolution. If another set X were compared to G1, a measure resolution F(g1A,g1b) may in effect set a lower limit on an ability to distinguish X from G1. See FIG. 23.

By varying protein concentration in known amounts, dimensional reduction criteria may, however, be refined. Conditions may be sought where a linear relationship exists between scores and subject materials, for example, having known scores, for example. A measure resolution derived previously may be used to guide adequate tradeoffs in values that may be made between dimension (d) and sample number (N). Sample sets may be generated for class of protein concentrations given in Table 2. Class separation may then be measured as a linear relationship sought between protein score and concentration, for example, in an embodiment.

Generally one seeks high measure resolution with a desire for more accurate calibration. From FIGS. 22 and 23, it appears clear that large sample sizes may be beneficial, although, of course, this may typically be limited by experimental factors. For a fixed sample size shown in FIG. 22, as demonstrated an upper limit is set in effect by covariance stability. The curves also show onset of nonlinear effects, which may also degrade resolution.

Figure 24:
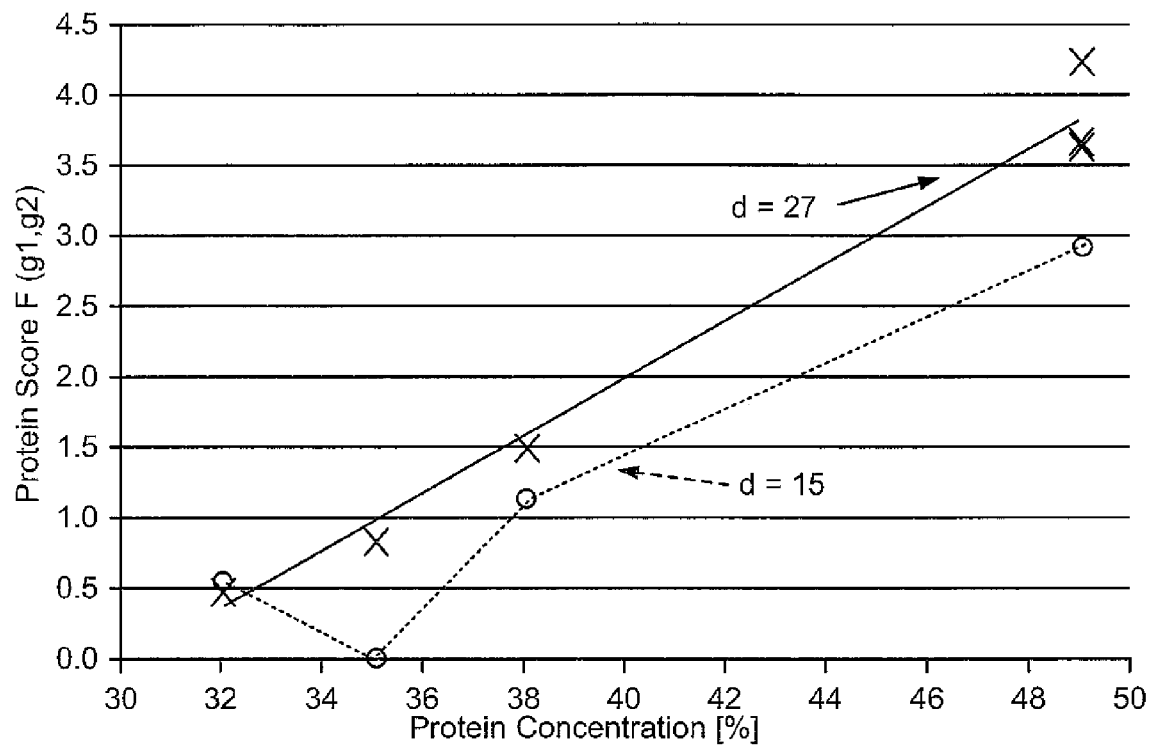
FIG. 24 is a sample plot showing for a set of signal samples protein score calibrated to concentration.

Within limits of a stable space having maximum resolution, a linear calibration relation may be found in FIG. 24. It shows a protein score and concentration with d=27 and N=44. A dashed plot at d=15 shows that too severe a dimensional reduction may result in a reduction or even loss of linearity. FIG. 24 shows protein score calibrated to concentration. Five component Raman spectra have a 10% Gaussian standard deviation/mean and Poisson noise. Total samples N=44.

A 3.5% minimum detectable change in protein concentration is obtained from a linear regression slope of 0.20 combined with a 0.7 measure resolution from FIG. 23. Increased chemical noise may reduce calibration sensitivity. Minimum changes of 14% in protein concentration may be detectable to if chemical noise increases to $\sigma_{Normal}/<I(\lambda_j)>=50\%$, which corresponds to a 1.6× increase of relative protein concentration.

Figure 25:
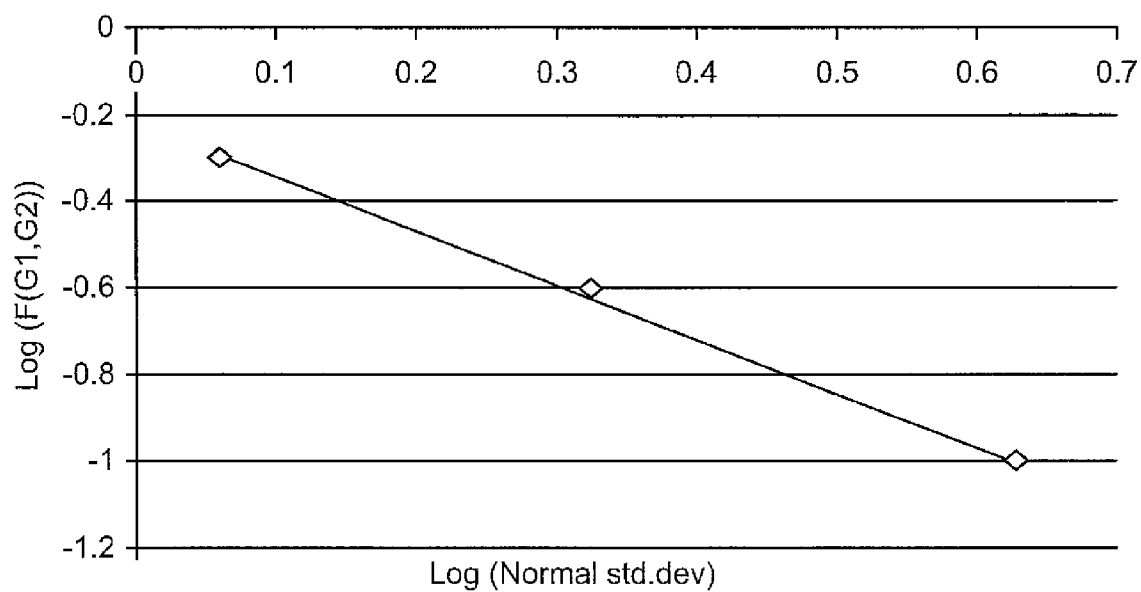
FIG. 25 is a sample plot showing protein score differences following a −1.2 power law dependence on chemical noise for a set of signal samples.

Noise sensitivity was measured by increasing relative concentration fluctuations from 10% to 25%, and 50% relative to mean intensity per channel. A resulting protein score follows an inverse 1.2 power law, as shown in FIG. 25. Using Relations (6) and (22) an expected functional relation between differences in class score and chemical fluctuations may be characterized as $$F(g1,g2)=(1+\alpha_0^2)^{-1/2}$$

where $\alpha_0=\alpha\sqrt{I_2}$, $\alpha=\sigma_{Normal}/<I(\lambda_j)>$, $I_g=I_2/I_1$, $I_1=<I_{g1}+I_{g2}>$, and $I_2=(<I_{g1}>^2+<I_{g2}>^2)$. Hence $\lim_{\alpha_0 \to \infty} F(g1,g2)=\alpha_0^{-1}$. Residual difference from the −1.2 power law may be due at least in part to a scale artifact since $O(\alpha_0) \sim 10^4 \gg 1$. FIG. 25 shows protein score differences following a −1.2 power law dependence on chemical noise. d=27 and N=44. The abscissa is the normal standard deviation per channel intensity ($\sigma/<I(\lambda_j)>$).

Another example concerns Raman spectra of activated T-lymphocytes. Here Raman spectra were obtained from a comparative study of flow cytometry with fluorescence activated cell sorting (FACS) and label-free integrated Raman and angular-scattering microscopy (IRAM) of T-cell activation, see SMITH, Z., WANG, J.-C., QUATAERT, S., and BERGER, A., (2010). Integrated Raman and angular scattering microscopy reveals chemical and morphological differences between activated and non-activated CD8+ T lymphocytes. *J. Biomedical Optics* 15(3) 036021 May/June.

A new activation rate estimate may be obtained by dimensional reduction and scaled linear discriminants derived from an IRAM Raman spectra. Relative T-cell activation rates stimulated by one of two cytotoxins, staphylococcal enterotoxin B (SEB) or phorbol myristate acetate (PMA), were compared with the light scattering index and FACS results, which counted numbers of fluorescently tagged cells expressing proteins CD69, CD137, or both from a large sample population (N~200,000~360,000).

Figure 26:
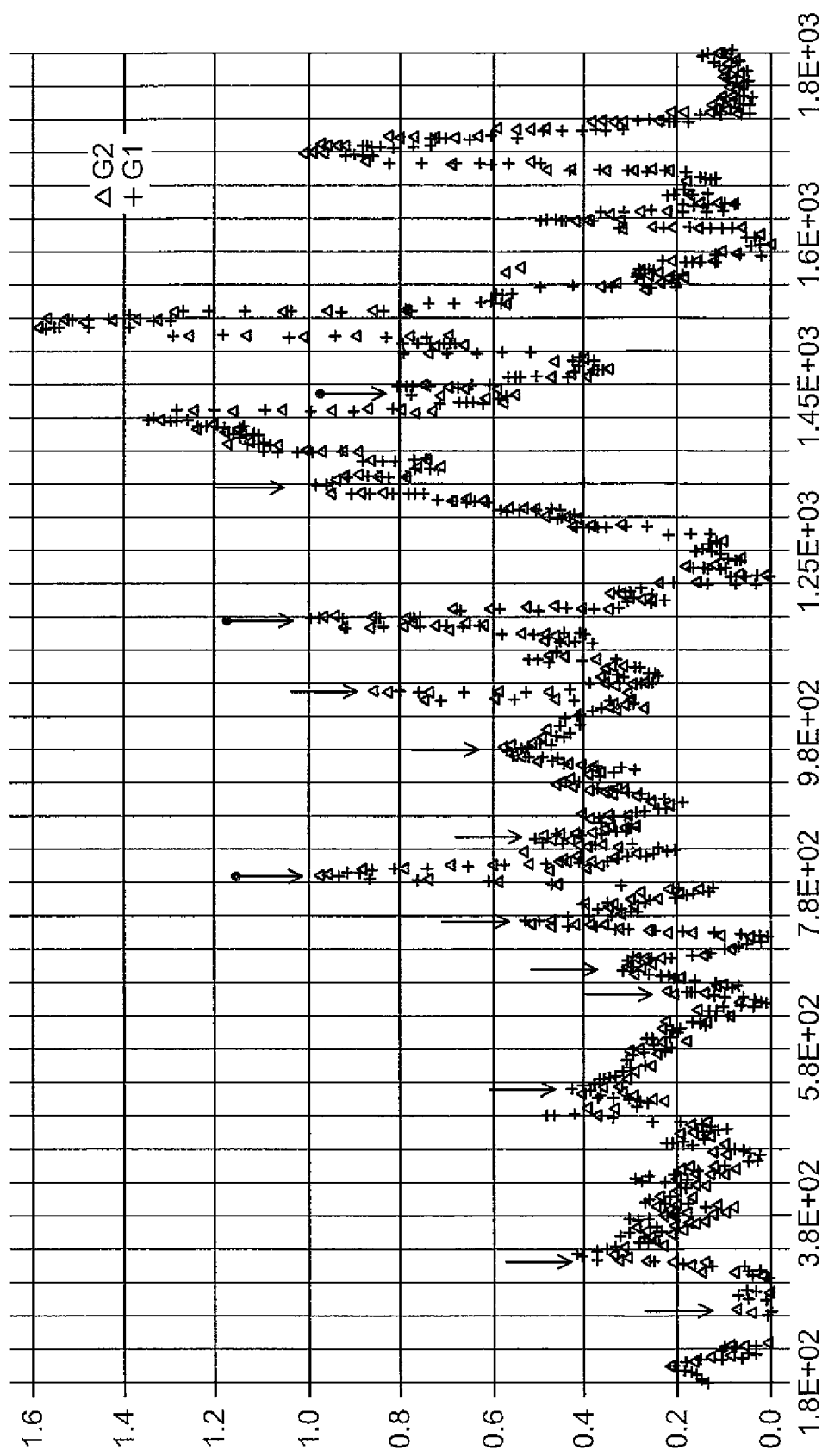
FIG. 26 is a sample plot showing Raman spectra averages for two groups of signal samples, one being a control group for the other.

The two types of CD8+ T-cell activation created different spectral responses. Activation states in each case were measured from a baseline control group. A first population was associated with response to phorbol myristate acetate (PMA), control group G1 and activated group G2, see FIG. 26. FIG. 26 shows Raman spectra averages for G1 and G2. 10 samples per average. Arrows mark peak intensities for the largest stable dimension d=17. The second treatment by staphylococcal enterotoxin B (SEB) had control group G3 and activated group G4. The IRAM study captured Raman intensities from p=1024 channels.

TABLE 3

| Scaled separation between T-cells (initial, activated). | | | | | | | | |
|---|---|---|---|---|---|---|---|---|
| Raw.GxGy-Scale | dim | F(a, b) | <a> | <b> | <a - b> | $s_a$ "N-1" | $s_b$ "N-1" | $(s_a^2 + s_b^2)^{.5}$ |
| G1G2 | 17 | 6.4 | −0.92 | −0.64 | 2.8E−01 | 0.0151 | 0.0158 | 2.2E−02 |
| G3G4 | 17 | 2.1 | 3.15 | 2.77 | 3.8E−01 | 0.0716 | 0.0585 | 9.2E−02 | a = G1 or G3, b = G2 or G4). G2 and G4 are respectively activated by SEB and PMA.

FIG. 26 spectra are ordered by peak height to rank sort wave numbers used to reduce dimension and find a stable space. An SVD null space=20=total number of samples in sets G1G2 or G2G3. A largest stable dimension is d=17. Four of seven peaks used by Smith et al. were identified by this method.

Class separations for each activation method to its control group were scored at d=17, N=20 and are noted in Table 3. A present score method provides an estimate of relative SEB/PMA activation intermediate to FACS and IRAM estimates, Table 4. ACS large sample, tagged population yields a lowest relative activation estimate with a highest confidence. An IRAM index was derived from a small/large class size gauge.

TABLE 4

| Relative SEB/PMA activation by method. | | | |
|---|---|---|---|
| | SEB activated % | PMA activated % | SEB/PMA |
| FACS | 26.38% | 97.66% | 27% |
| F(G3, G4) | 2.1 | | |

TABLE 4-continued

| Relative SEB/PMA activation by method. | | | |
|---|---|---|---|
| | SEB activated % | PMA activated % | SEB/PMA |
| F(G2, G1) | | 6.4 | 33% |
| IRAM index | 4 | 10 | 40% |

Temporal effects of antibiotic dosing on experimentally measured *E. Coli* Raman spectra is a third example provided. This case analyzes time dependent spectra. A stable space is found and an alternate measure resolution is estimated from raw unscaled signal sample as the small sample size made use of a partitioning method problematic and bootstrap estimates were unavailable. Three dimensional normed score vectors are used for polychotomous classification and metric analysis. Class separability is compared with PCA.

Raman spectra were taken from a study of antibiotic (Penicillin G/Streptomycin) dosing of *E. Coli*. See MORITZ, T., POLAGE, C., TAYLOR, D., Krol, D., Lane, S., and Chan, J. (2010). Evaluation of *Escherichia Coli* cell response to antibiotic treatment using laser tweezers Raman spectroscopy. *J. Clin. Microbiol.* November; 48(11), 4287-90.

Figure 27:
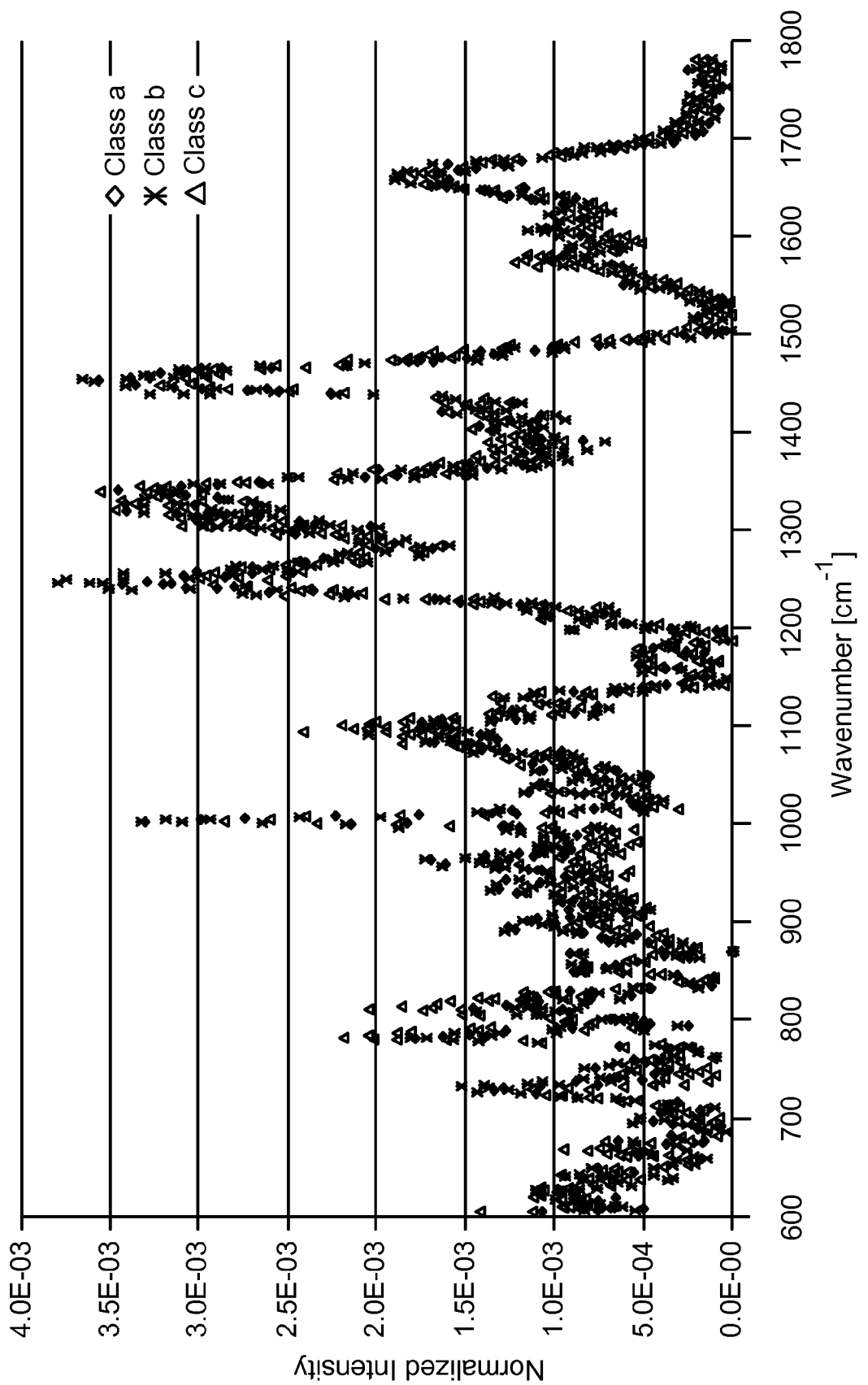
FIG. 27 is a sample plot showing averages of Raman spectra measured temporal effects on *E. Coli*. Fomr three sets of signal samples.

The apparatus had p=863 channels (wavenumbers). Class a represents initial measurements at t=0 ($N_a$=14 samples). Class b measurements were taken at t=1 hr ($N_b$=13 samples). Class c was measured at t=6 hr ($N_b$=15 samples). Averaged values are shown in FIG. 27. Therefore, FIG. 27 shows averages of Raman spectra measure antibiotic temporal effect on *E. Coli*. Class a (t=0), class b (t=1 hr), class c (t=6 hr).

Figure 28:
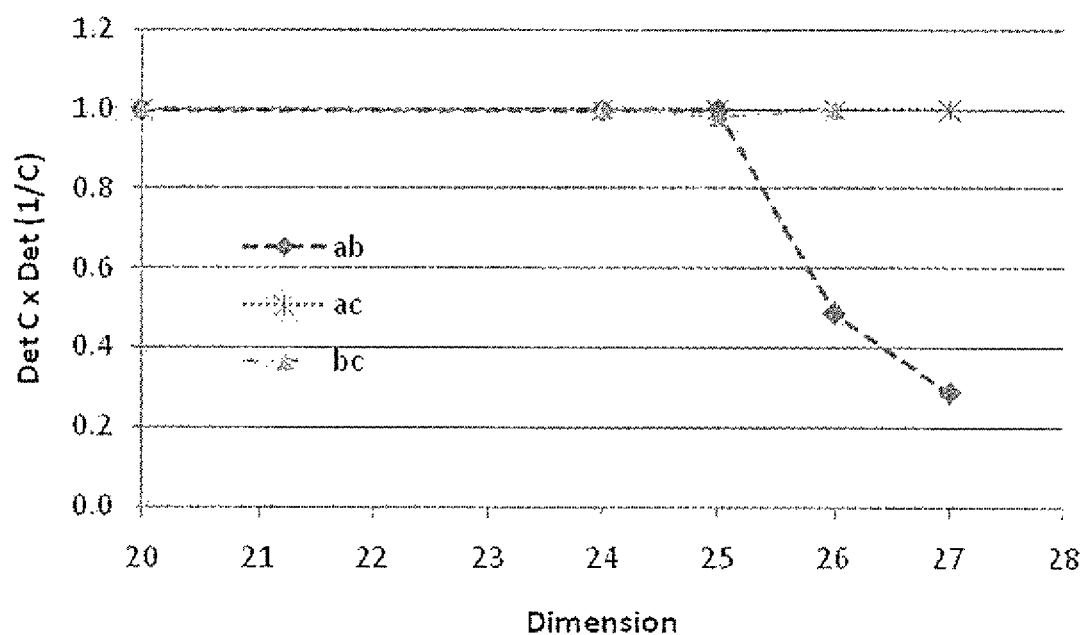
FIG. 28 is a sample plot showing an embodiment of evaluation of covariance stability for a set of signal samples.

A SVD-defined null space places upper bounds on the rank in accordance with sample sizes 27, 28, or 29 for class pairs (a,b), (b,c), and (a,c), respectively. The bound is lowered to d=25 by evaluating covariance stability as shown in FIG. 28.

Figure 29:
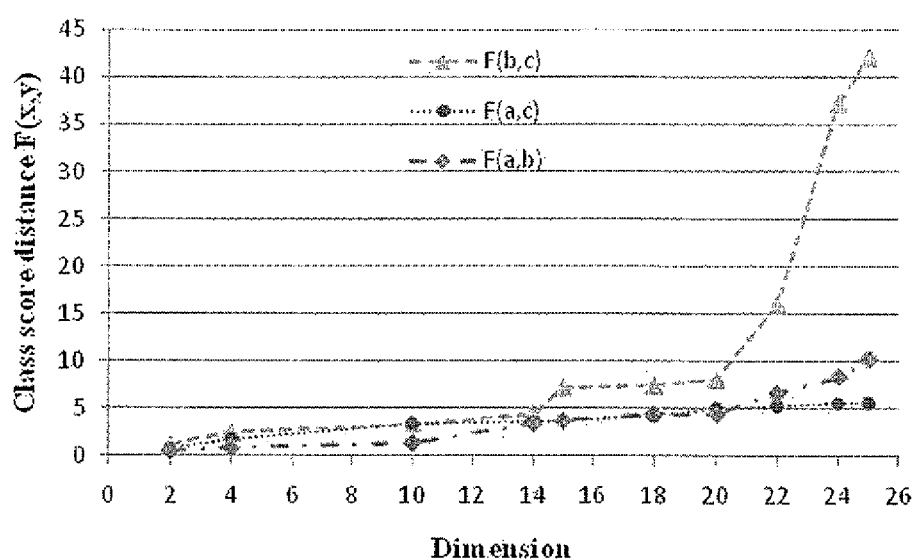
FIG. 29 is a sample plot showing score distance versus dimension for several samples of Raman spectra.

Corresponding distances between class scores for d 25 are given in FIG. 29. FIG. 29 shows score distance versus dimension for Raman spectra for classes a,b,c. Note that the triangle inequality is violated for dimensions d>20. An alternative measure resolution for the score distance F(x,y)~1.0 may be derived from calculating class separations $F_{raw}$(a,b)=0.4, $F_{raw}$(b,c)=1.0, and $F_{raw}$(a,c)=0.7 from normalized raw signal samples.

Table 5 shows results of a metric test for a score vector space {V, +} using an F-metric criteria from a triangle inequality and Relation (13). The upper dimensional bound is reduced to d=20 if the norm and F-metric condition is applied.

TABLE 5

Metric test for score vector space {v, +}.

| | $\|F(a,b)\|$ | $\|F(a,c)\|$ | $\|F(b,c)\|$ ≤ $\|F(a,b)\|$ + $\|F(a,c)\|$ $\|F(b,c)\|$ | L2-F-norm condition |
|---|---|---|---|---|
| d = 25 | 10.2 | 6.7 | 42.2 | No |
| d = 22 | 6.6 | 5.8 | 16.1 | No |
| d = 20 | 4.4 | 5.2 | 8.2 | Yes |
| d = 18 | 4.4 | 4.5 | 7.6 | Yes |
| d = 15 | 3.7 | 3.9 | 7.5 | Yes |
| d = 14 | 3.4 | 4.1 | 5.0 | Yes |
| d = 10 | 1.5 | 4.2 | 4.1 | Yes |
| d = 4 | 1.0 | 2.6 | 3.6 | Yes |

A Euclidean space $a_\angle + b_\angle + C_\angle = 180°$ is confirmed at d=20, from lengths in Table 5 where three angles: $a_\angle = 117°$, $b_\angle = 34°$, $c_\angle = 29°$ are derived from the law of cosines $$c_\triangleleft = \cos^{-1}\left[\frac{\|bc\|^2 + \|ac\|^2 - \|ab\|^2}{2 \cdot \|bc\| \cdot \|ac\|}\right].$$

TABLE 6

Metric test for score vector space {v, ⊕}.

| L2-norm | | Inverse Triangle inequality (pairwise) [$\|x\| - \|y\|$] ≤ $\|x - y\|$ | | | d* metric norm condition | | |
|---|---|---|---|---|---|---|---|
| | | d = 24 | | | | | |
| $\|a\|$ | 110 | [$\|a\| - \|b\|$] | 638 | No | $\|a - b\|$ | 181 | |
| $\|b\|$ | 748 | [$\|a\| - \|c\|$] | 666 | No | $\|a - c\|$ | 187 | |
| $\|c\|$ | 777 | [$\|b\| - \|c\|$] | 28 | No | $\|b - c\|$ | 22 | |
| | | d = 4 | | | | | |
| $\|a\|$ | 46 | [$\|a\| - \|b\|$] | 12 | No | $\|a - b\|$ | 4 | |
| $\|b\|$ | 57 | [$\|a\| - \|c\|$] | 2 | Yes | $\|a - c\|$ | 3 | |
| $\|c\|$ | 48 | [$\|b\| - \|c\|$] | 10 | No | $\|b - c\|$ | 4 | |

A candidate metric discussed previously for a score vector space {V, ⊕} was also examined. An inverse triangle inequality was used on all class pairs over a dimensional range shown in Table 6. Results show that for most inequality does not hold (listed as False). A conclusion may be that this candidate metric space may provide little or marginal benefit for a context such as this for these class distributions.

Figure 30:
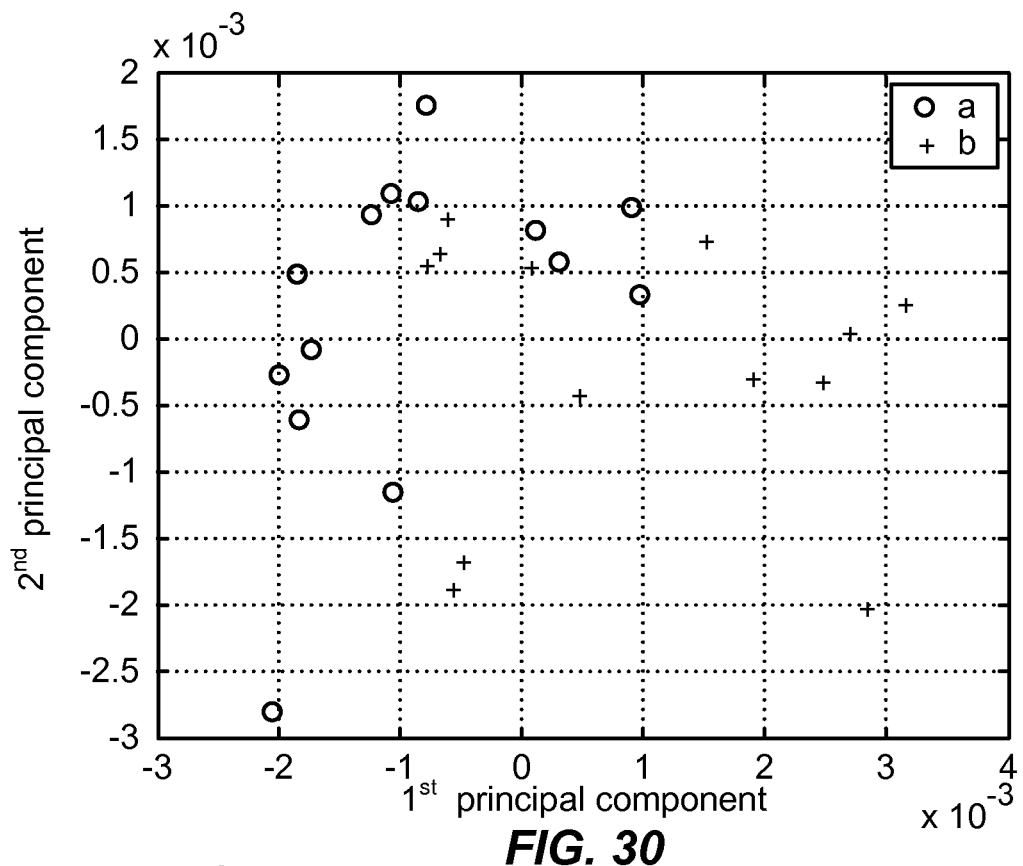
FIGS. 30 and 31 are sample plots illustrating potential impact of applying a candidate metric on several samples of Raman spectra.
Figure 31:
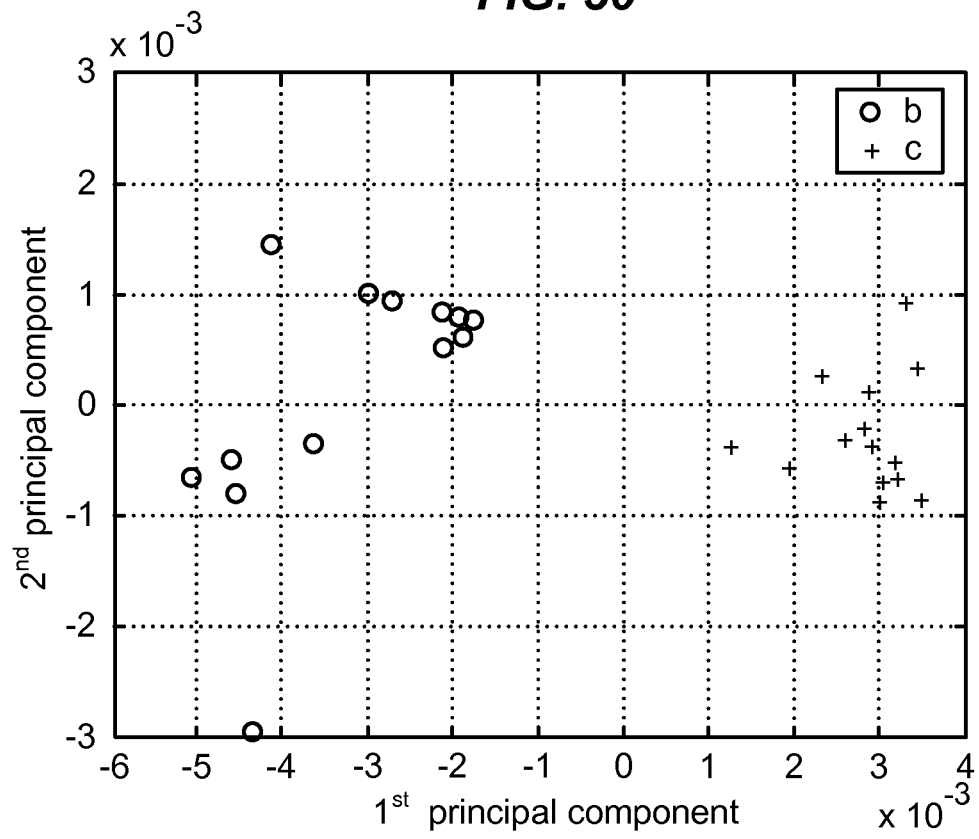

Classes a and b are statistically indistinguishable at a distance F(a,b)=0.4 (left). Classes b and c show visible separation with F(b,c)=1.6 (right). The first two principal components are plotted in FIG. 30 and consistent with scores at d=2 in FIG. 29. As class separation is a monotonic increasing function of dimension, loss of information results with too severe a reduction in dimension. Short time effects may be distinguished from the initial standard spectra by scoring the distribution in the largest dimension in a stable space.

One might consider that class separation could be increased if more principal components were selected. However PCA is a case of a rotational transformation. It appears that rotation of a matrix, either before or after scaling does not measurably improve class separation compared to scaling alone based at least in part on experimental evaluation, as discussed below.

Raman abc signal sample values were used to evaluate whether shear operations enhance class separability and a dimension d=10 was chosen as an example. These non-commutative operations are rotations applied to matrices prior to, or after, scaling. A class A induces a 3-by-(d−1) mapping $\mathbb{R}_A$ derived by a Jacobi procedure. An induced mapping may be viewed as composed of three parameters, which comprise the two axes selected by the maximum off diagonal correlation coefficient and the corresponding rotation angle.

Rotations applied to raw signal sample values for classes a, b, and c prior to scaling are first considered (ordering abbreviated as raw:rot:scaled, e.g. aRot.raw denotes $\mathbb{R}_a$ and acScaled.aRot is the rotated data matrix $\mathbb{R}_a$ subsequently scaled by the aRot-cRot classes).

While initial samples had p=863 measurement channels normalized as standard procedure to address potential instrument variations, reduction to the top 10 peaks further reduced raw means and standard deviations. Corresponding scores indicate raw class pairs are indistinguishable in accordance with a pseudo-metric Relation 11(d)

$F(a,b)=0.4, F(a,c)=0.4, F(b,c)=0.8.$

Table 7 shows results of rotating raw matrices. No measurable increase in class separation is observed. Three Fisher distances are shown for a given class rotation since the other two classes are operated on by the same rotation, e.g. $\mathbb{R}_a(b)$ denotes that the raw.b class was rotated by the a-induced rotation. Likewise F(b:a, c:a) is the class separation between $\mathbb{R}_a(b)$ and $\mathbb{R}_a(c)$.

TABLE 7

Class separations for rotated matrices without scaling. Raman a, b, c classes d = 10.

| aRot.raw | | | bRot.raw | | | cRot.raw | | |
|---|---|---|---|---|---|---|---|---|
| F(b:a, c:a) | <b:a - c:a> | $(\sigma_{b:a}^2 + \sigma_{c:a}^2)^{.5}$ | F(a:b, c:b) | <a:b-c:b> | $(\sigma_{a:b}^2 + \sigma_{c:b}^2)^{.5}$ | F(b:c, c) | <b:c-c> | $(\sigma_{b:c}^2 + \sigma_c^2)^{.5}$ |
| 0.9 | 1.3.E-03 | 7.0.E-04 | 0.2 | 2.2.E-04 | 5.6.E-04 | 0.3 | 1.1.E-03 | 6.4.E-04 |
| F(a, c:a) | <a - c:a> | $(\sigma_c^2 + \sigma_{c:a}^2)^{.5}$ | F(c:b, b) | <c:b - b> | $(\sigma_b^2 + \sigma_{c:b}^2)^{.5}$ | F(a:c, c) | <a:c-c> | $(\sigma_{a:c}^2 + \sigma_c^2)^{.5}$ |
| 0.8 | 9.3.E-04 | 6.1.E-04 | 0.7 | 7.8.E-04 | 5.7.E-04 | 0.7 | 6.8.E-04 | 5.2.E-04 |
| F(a, b:a) | <a - b:a> | $(\sigma_c^2 + \sigma_{b:a}^2)^{.5}$ | F(a:b, b) | <a:b - b> | $(\sigma_{a:b}^2 + \sigma_b^2)^{.5}$ | F(a:c, b:c) | <a:c - b:c> | $(\sigma_{a:c}^2 + \sigma_{b:c}^2)^{.5}$ |
| 0.3 | 3.6.E-04 | 6.3.E-04 | 0.5 | 5.6.E-04 | 6.0.E-04 | 0.3 | 3.9.E-04 | 5.9.E-04 |

Pair-wise scaling of previously rotated matrices $\mathcal{R}_a(a)$, $\mathcal{R}_b(b)$, $\mathcal{R}_c(c)$ produces Table 8. None of the corresponding rotated and then scaled class separations exceed F=1.6, which suggests that rotations do not appear to measurably or usefully increase class separation by referring to FIG. 23.

TABLE 8

Class separation for rotated then scaled Raman a, b, c spectra at d = 10.

| Scaled (a.rot, c.rot) | | | | Scaled (a.rot, b.rot) | | | | Scaled (b.rot, c.rot) | | |
|---|---|---|---|---|---|---|---|---|---|---|
| F(b:a, c:a) | <b:a - c:a> | $(\sigma_{b:a}^2 + \sigma_{c:a}^2)^{.5}$ | F(a:b, c:b) | <a:b - c:b> | $(\sigma_{a:b}^2 + \sigma_{c:b}^2)^{.5}$ | F(b:c, c) | <b:c -c> | $(\sigma_{b:c}^2 + \sigma_c^2)^{.5}$ |
| 0.9 | 2.8.E−03 | 1.5.E−03 | 0.0 | 1.6.E−03 | 1.8.E−02 | 0.7 | 2.6.E−03 | 2.0.E−03 |
| F(a, c:a) | <a - c:a> | $(\sigma_a^2 + \sigma_{c:a}^2)^{.5}$ | F(a:b, b) | <a:b - b> | $(\sigma_{a:b}^2 + \sigma_b^2)^{.5}$ | F(a:c, c) | <a:c - c> | $(\sigma_{a:c}^2 + \sigma_c^2)^{.5}$ |
| 1.6 | 3.6.E−03 | 1.1.E−03 | 0.2 | 5.5.E−03 | 1.4.E−02 | 1.4 | 3.5.E−03 | 1.2.E−03 |
| F(a, b:a) | <a - b:a> | $(\sigma_a^2 + \sigma_{c:a}^2)^{.5}$ | F(c:b, b) | <c:b - b> | $(\sigma c:b^2 + \sigma_b^2)^{.5}$ | F(a:c, b: c) | <a:c - b:c> | $(\sigma_{a:c}^2 + \sigma_{b:c}^2)^{.5}$ |
| 0.3 | 7.2.E−04 | 1.3.E−03 | 0.3 | 7.1.E−03 | 1.2.E−02 | 0.2 | 9.6.E−04 | 1.9.E−03 |
| F(b:c, c) | <b:c - c> | $(\sigma_{b:c}^2 + \sigma_c^2)^{.5}$ | F(b:a, c:a) | <b:a - c:a> | $(\sigma_{b:a}^2 + \sigma_{c:a}^2)^{.5}$ | F(c:b, b) | <c:b-b> | $(\sigma_{c:b}^2 + \sigma_b^2)^{.5}$ |
| 1.0 | 2.1.E−03 | 1.1.E−03 | 0.4 | 1.2.E−02 | 1.7.E−02 | 0.4 | 1.2.E−03 | 1.7.E−03 |
| F(a:c, c) | <a:c - c> | $(\sigma_{a:c}^2 + \sigma_c^2)^{.5}$ | F(b:a, a) | <b:a - a> | $(\sigma_{b:a}^2 + \sigma_a^2)^{.5}$ | F(a:b, b) | <a:b - b> | $(\sigma_{a:b}^2 + \sigma_b^2)^{.5}$ |
| 1.3 | 2.6.E−03 | 1.0.E−03 | 0.2 | 5.0.E−03 | 1.5.E−02 | 0.1 | 3.1.E−04 | 1.7.E−03 |
| F(a:c, b:c) | <a:c - b:c> | $(\sigma_{a:c}^2 + \sigma_{b:c}^2)^{.5}$ | F(c:a, a) | <c:a - a> | $(\sigma_{c:a}^2 + \sigma_a^2)^{.5}$ | F(a:b, c:b) | <a:b - c:b> | $(\sigma_{a:b}^2 + \sigma_{a:b}^2)^{.5}$ |
| 0.2 | 5.3.E−04 | 1.3.E−03 | 0.4 | 7.4.E−03 | 8.5.E−03 | 0.2 | 8.9.E−04 | 2.2.E−03 |

Rotation of previously scaled matrices results in Table 9. Again by comparison with FIG. 23 at d =10, no measurable or noticeable improvement in class separation was found by subsequent rotation of scaled signal sample values.

TABLE 9

Class separations for rotations of scaled Raman a, b, c spectra at d = 10.

| Rot.ac-Scaled.raw | | | Rot.ab-Scaled.raw | | | Rot.bc-Scaled.raw | | |
|---|---|---|---|---|---|---|---|---|
| F(a:c, c) | <a:c-c> | $(\sigma_{a:c}^2 + \sigma_c^2)^{.5}$ | F(a:b, b) | <a:b-b> | $(\sigma_{a:b}^2 + \sigma_b^2)^{.5}$ | F(b:c, c) | <b:c-c> | $(\sigma_{b:c}^2 + \sigma_c^2)^{.5}$ |
| 0.4 | 3.5.E−04 | 4.9.E−04 | 0.6 | 5.3.E−04 | 4.3.E−04 | 2.4 | 3.6.E−03 | 7.4.E−04 |
| F(b:c, c) | <b:c-c> | $(\sigma_{b:c}^2 + \sigma_c^2)^{.5}$ | F(c:b, b) | <c:b-b> | $(\sigma_{c:b}^2 + \sigma_b^2)^{.5}$ | F(a:c, c) | <a:c-c> | $(\sigma_{a:c}^2 + \sigma_c^2)^{.5}$ |
| 0.1 | 8.7.E−05 | 5.9.E−04 | 0.2 | 1.8.E−04 | 4.5.E−04 | 1.4 | 2.9.E−03 | 1.0.E−03 |
| F(c:a, a) | <c:a-a> | $(\sigma_{c:a}^2 + \sigma_a^2)^{.5}$ | F(b:a, a) | <b:a-a> | $(\sigma_{b:a}^2 + \sigma_a^2)^{.5}$ | F(c:b, b) | <c:b -b> | $(\sigma_{a:b}^2 + \sigma_b^2)^{.5}$ |
| 2.1 | 1.8.E−03 | 4.2.E−04 | 0.5 | 4.3.E−04 | 4.7.E−04 | 2.5 | 4.5.E−03 | 9.1.E−04 |
| F(b:a, a) | <b:a-a> | $(\sigma_{b:a}^2 + \sigma_a^2)^{.5}$ | F(c:a, a) | <c:a-a> | $(\sigma_{c:a}^2 + \sigma_a^2)^{.5}$ | F(a:b, b) | <a:b-b> | $(\sigma_{a:b}^2 + \sigma_b^2)^{.5}$ |
| 0.2 | 1.6.E−04 | 5.3.E−04 | 0.0 | 2.2.E−05 | 4.8.E−04 | 0.3 | 9.1.E−04 | 1.4.E−08 |

These results suggest a possible conclusion that rotations based on reducing within-class correlation coefficients do not appear to measurable improve class separability.

In the above Raman measurements apparatus-specific effects are addressed at least in part out by normalizing sample measurements. Normalization is typically an effective way of addressing apparatus-specific variations, which may otherwise induce bias. As an approach to study this effect, while excluding dimensionality and sample size effects, Iris flower measurements for three classes Setosa (Se) virginica (Vi), and Versicolor (Ve) were taken from: FISHER, R. (1936). The use of multiple measurements in taxonomic problems. *Annals of Eugenics* 7, 179-188. Four measurements dimensions and 50samples from each class Se, Vi, and Ve exist.

Fisher noted that "*Iris virginica* differs from the two other samples in not being taken from the natural colony . . . " He also suggested a method to create a compound score, which he proposed as a linear combination of the product of individual raw class mean scores times their deviation from their common mean. One may then calculate a compound covariance and find a corresponding scale factor.

TABLE 10

Fisher distances for Iris flower classes using raw or normalized measurements

| | F(Ve,Vi) | F(Ve,Se) | F(Se,Vi) |
|---|---|---|---|
| Raw data | | | |
| Compound | 1.27 | 3.45 | 4.93 |
| Pair wise | 1.33 | 3.59 | 4.94 |
| Normalized | | | |
| Compound | 1.13 | 4.38 | 5.59 |
| Pair wise | 1.23 | 4.48 | 6.07 |

If raw measurements exhibit bias, as with the Iris species; comparable class separations result by comparing multi-category scaling from the common mean to pairwise in-class scaling, see Table 10. The table also shows that measurement normalization slightly increases class separability.

Compound scaling generally tends to obscure differences between pairs of classes as well as reduce class separability. An example of this is shown in Table 11 where normalized Raman a,b,c samples at d=24 dimensions were used as an example. Thus normalizing integrated spectral intensity to factor out apparatus-dependent variations may have an added benefit of reduced probability of misclassification.

TABLE 11

Comparison of Fisher distances for Raman a, b, c classes at d = 24.

| d = 24 | F(a,c) | F(a,b) | F(b,c) |
|---|---|---|---|
| Raw | 1.4 | 0.3 | 1.5 |
| Pairwise scaled | 5.6 | 8.4 | 37.3 |
| Compound scaled | 3.0 | 0.1 | 10.2 |

Dimensionality reduction by use of a covariance stability criterion has led to accurate class discrimination in a number of evaluations using Raman spectra. Several estimates of measure resolution have been given. A normed score-vector space provides another method of polychotomous classification. Two metrics corresponding to different types of group addition in a normed space were also considered. One yielded an inner product, but limited dimensional range. The other confirmed the Euclidean property over most, but not all of a stable range. A question may exist whether imposition of metric structure on a normed space yields a further benefit if quantifying spectral components. Too severe a dimensionality reduction, as may occur with principal component analysis, might result in a loss of desired information. A desired space may be determined by covariance stability so that potentially a linear relation between derived scores and known component concentration in a noisy environment results. Nonetheless, as noted previously, these examples are intended merely to be illustrative and are not intended to limit the scope of claimed subject matter.

It will, of course, also be understood that, although particular embodiments have just been described, claimed subject matter is not limited in scope to a particular embodiment or implementation. For example, one embodiment may be in hardware, such as implemented on a device or combination of devices, as previously described, for example. Likewise, although claimed subject matter is not limited in scope in this respect, one embodiment may comprise one or more articles, such as a storage medium or storage media, for example, that may have stored thereon instructions executable by a specific or special purpose system or apparatus. As one potential example, a specific or special purpose computing platform may include one or more processing units or processors, one or more input/output devices, such as a display, a keyboard or a mouse, or one or more memories, such as static random access memory, dynamic random access memory, flash memory, or a hard drive, although, again, claimed subject matter is not limited in scope to this example.

Although embodiments have been described with reference to accompanying drawings, it is to be noted that various changes or modifications may be accomplished. Changes or modifications, whether apparent to one of ordinary skill in the art or not, are to be understood as being intended to be subject matter within the scope of the claims that follow.

The invention claimed is:

1. A system comprising:
an arrangement of components capable of being synchronized to generate images or spectra to be digitally rendered and categorized through parallel processing of illuminated regions of a thin film sample at a sufficient throughput so that on average a misclassification probability of one part per billion in 12 hours is at least met or exceeded;
said arrangement including:
an optical flat to receive one or more of said thin film samples, said one or more of said thin film samples to comprise a thinly approximately evenly spread sample, said optical flat being part of a movably controllable stage assembly so that separate regions of a particular thin film sample are capable of being illuminated during system operation over a processing period;
a light source with associated optics to be capable of illuminating said separate regions of said particular thin film sample at least over a range of wavelengths of light, said separate regions of said particular thin film sample to be illuminated in a manner so that at least some of the illuminating light is capable of being captured by an optical detector; and
a special purpose computing device coupled to said optical detector so as to receive captured pixel signal sample values over one or more of said processing periods, said captured pixel signal sample values to represent a signal characteristic of said illuminating light for said separate regions of said particular thin film sample, said special purpose computing device programmed so as to be capable of parallel processing pixel signal values from said separate regions of said particular thin film sample for spectral or high resolution spatial evaluation.

2. The system of claim 1, wherein said signal characteristic comprises at least light intensity over a range of selected wavelengths of visible light.

3. The system of claim 1, wherein said particular thin film sample to comprise an organic substance.

4. The system of claim 1, wherein said particular thin film sample is to be spin-coated on said optical flat.

5. The system of claim 1, wherein said optical detector further comprises a CCD or complementary metal oxide semiconductor (CMOS) device array.

6. The system of claim 1, wherein said light source with associated optics includes a broadband laser with a tunable filter.

7. A method of processing thin film samples for spectral or high resolution spatial evaluation comprising:
providing a sample substance with respect to an optical flat in a manner to be thinly approximately evenly spread;
illuminating separate regions of the thinly approximately evenly spread sample substance with light at selected wavelengths through relative positioning with respect to a light source;
capturing as pixel signal sample values at least some of said light that illuminated said separate regions;
parallel processing the captured pixel signal sample values for said separate regions to generate a spectra for particular signal characteristics of said light that illuminated said separate regions;
categorizing of said sample substance based at least in part on a comparison of the generated spectra with stored spectra; and
synchronizing said providing, illuminating, capturing, parallel processing and categorizing at a sufficient rate so that on average a misclassification probability of one part per billion in 12 hours is at least met or exceeded.

8. The method of claim 7, wherein said particular signal characteristics comprises at least light intensity over a range of selected wavelengths of visible light.

9. The method of claim 7, wherein said sample substance comprises an organic substance.

10. The method of claim 7, wherein providing a sample substance with respect to an optical flat in a manner to be thinly approximately evenly spread comprises spin-coating said sample substance.

11. The method of claim 7, wherein said parallel processing to generate a spectra comprises employing one or more signal transformations with respect to said captured pixel signal sample values to mimic signal transformations employed with respect to said stored spectra.

12. The method of claim 11, wherein said one or more signal transformations comprises at least one of the following: a scaling or scaling-like transformation; a rotation or rotation-like transformation; a shear or shear-like transformation; or any combination thereof.

13. The method of claim 11, wherein said applying one or more signal transformations comprises applying a shear or shear-like transformation.

14. The method of claim 7, wherein said categorizing of said sample substance comprises categorizing said sample substance with respect to a variety of classes based at least in part on a comparison of the generated spectra with stored spectra corresponding to said classes.

15. The method of claim 7, wherein said categorizing based at least in part on a comparison of the generated spectra with stored spectra comprises scoring a spectra comparison metric employed with respect to the generated and stored spectra.

16. The method of claim 7, wherein said parallel processing to generate a spectra comprises employing one or more signal transformations with respect to said captured pixel signal sample values.

17. The method of claim 16, wherein said one or more signal transformations comprises at least one of the following: a scaling or scaling-like transformation; a rotation or rotation-like transformation; a shear or shear-like transformation; or any combination thereof.

18. The method of claim 17, wherein said one or more signal transformations to be employed are determined based at least in part on satisfying a covariance stability criterion for the set of signal sample values.

* * * * *